(12) United States Patent
Ezrin et al.

(10) Patent No.: US 12,429,486 B2
(45) Date of Patent: Sep. 30, 2025

(54) USE OF TENASCIN-C AS AN EXTRACELLULAR MARKER OF TUMOR-DERIVED MICROPARTICLES

(71) Applicant: NX Pharmagen Inc., Lexington, KY (US)

(72) Inventors: Alan M. Ezrin, Sarasota, FL (US); Steven G. Griffiths, Moncton (CA)

(73) Assignee: NX PHARMAGEN INC., Lexington, KY (US)

( * ) Notice: Subject to any disclaimer, the term of this patent is extended or adjusted under 35 U.S.C. 154(b) by 0 days.

(21) Appl. No.: 18/060,455

(22) Filed: Nov. 30, 2022

(65) Prior Publication Data

US 2023/0160899 A1 May 25, 2023

Related U.S. Application Data

(63) Continuation of application No. 14/893,042, filed as application No. PCT/US2014/038615 on May 19, 2014, now abandoned.

(60) Provisional application No. 61/825,951, filed on May 21, 2013.

(51) Int. Cl.
  *G01N 33/00* (2006.01)
  *G01N 33/574* (2006.01)

(52) U.S. Cl.
  CPC . *G01N 33/57488* (2013.01); *G01N 33/57407* (2013.01); *G01N 2333/4703* (2013.01); *G01N 2333/78* (2013.01)

(58) Field of Classification Search
  CPC ....... G01N 33/57484; G01N 33/57488; G01N 33/57407; G01N 2333/4703
  See application file for complete search history.

(56) References Cited

U.S. PATENT DOCUMENTS

| | | | |
|---|---|---|---|
| 5,807,522 A | 9/1998 | Brown et al. | |
| 6,037,186 A | 3/2000 | Stimpson | |
| 6,291,170 B1 | 9/2001 | Van Gelder et al. | |
| 6,812,023 B1 | 11/2004 | Lamparski et al. | |
| 6,899,863 B1 | 5/2005 | Dhellin et al. | |
| 8,552,364 B2 | 10/2013 | Graves et al. | |
| 10,247,736 B2 | 4/2019 | Graves et al. | |
| 10,877,046 B2 | 12/2020 | Brohman et al. | |
| 10,928,402 B2 | 2/2021 | Ezrin et al. | |
| 11,513,125 B2 | 11/2022 | Ezrin | |
| 2002/0102264 A1* | 8/2002 | Cheung | C07K 16/18 530/389.1 |
| 2010/0196426 A1 | 8/2010 | Skog et al. | |
| 2010/0297003 A1 | 11/2010 | De Santis et al. | |
| 2013/0330753 A1 | 12/2013 | Ezrin | |
| 2016/0097771 A1 | 4/2016 | Ezrin et al. | |
| 2020/0124607 A1 | 4/2020 | Ezrin | |
| 2021/0231674 A1 | 7/2021 | Ezrin et al. | |
| 2021/0270840 A1 | 9/2021 | Brohman et al. | |

FOREIGN PATENT DOCUMENTS

| | | | | |
|---|---|---|---|---|
| CA | 2830772 A1 | * | 9/2012 | ......... A61K 39/0011 |
| WO | WO-9913313 A1 | | 3/1999 | |
| WO | WO-0205945 A1 | | 1/2002 | |
| WO | WO-2011109440 A1 | | 9/2011 | |
| WO | WO-2012170711 A1 | | 12/2012 | |
| WO | WO-2013184830 A1 | | 12/2013 | |
| WO | WO-2014189842 A2 | | 11/2014 | |

OTHER PUBLICATIONS

Pruss (J. Mol. Biol., vol. 98, p. 465-478, 1975) (Year: 1975).*
Arakawa et al Antibodies, 1: 215-238, 2012 (Year: 2012).*
Kudou et al.Protein Expression and Purification 75:46-54, 2011 (Year: 2011).*
Avseenko et al., "Immobilization of Proteins in Immunochemical Microarrays Fabricated by Electrospray Deposition", Anal. Chem., vol. 73, No. 24, Dec. 15, 2001, pp. 6047-6052.
Baj-Krzyworzeka et al., "Tumour-derived microvesicles carry several surface determinants and mRNA of tumour cells and transfer some of these determinants to monocytes." Cancer Immunology, Immunotherapy (2006); 55 (7): 808-818.
Bard et al., "Proteomic Analysis of Exosomes Isolated from Human Malignant Pleural Effusions", Am J Respir Cell Mol Biol. vol. 31, 2004, pp. 114-121.
Baxevanis (Expert Opinion: Drug Discovery, vol. 3, No. 4, p. 441-452, 2008) (Year: 2008).
Bourdon et al., "Human Glioma-Mesenchymal Extracellular Matrix Antigen Defined by Monoclonal Antibody", Cancer Research, vol. 43, Jun. 1983, pp. 2796-2805.
Brown, Corrie, "Antigen Retrieval Methods for Immunohistochemistry", Toxicologic Pathology, vol. 26, No. 6, 1998, pp. 830-831.
Chavez-Munoz et al., "Profile of Exosomes Related Proteins Released by Differentiated and Undifferentiated Human Keratinocytes", Journal of Cellular Physiology, vol. 221, 2009, pp. 221-231.
Cheruvanky, et al., "Rapid isolation of urinary exosomal biomarkers using a nanomembrane ultrafiltration concentrator." Am J Physiol Renal Physiol. (2007); 292: F 1657-F 1661.
Chiovaro, et al., Transcriptional regulation of tenascin genes, Cell Adhesion & Migration, Jan.-Apr. 2015, pp. 34-47, vol. 9, No. 1-2.
Choi, et al., "Proteomic Analysis of Microvesicles Derived from Human Colorectal Cancer Cells." Journal of Proteome Research (2007); 6: 4646-4655.
Chute et al., "Novel Peptide with Affinity for Canonical Heat Shock Proteins (HSPs) as a Tool For Capture and Enrichment of Extracellular Microvesicles", Available at : http://www.newenglandpeptide.com/images/ISEV-2013-lan.pdf, 2013, 1 page.

(Continued)

*Primary Examiner* — Lei Yao
(74) *Attorney, Agent, or Firm* — Cooley LLP

(57) ABSTRACT

The present disclosure provides methods for isolating tumor-derived microparticles from a subject for analysis, specifically by isolating Tenascin-C positive microparticles from a sample from the subject to obtain tumor-derived microparticles. Methods for determining the expression status of biomarkers in the tumor-derived microparticles and methods for determining additional characteristics of the tumor-derived microparticles are also provided.

7 Claims, 11 Drawing Sheets

Specification includes a Sequence Listing.

(56) References Cited

OTHER PUBLICATIONS

Cocucci et al., "Enlargeosome Traffic: Exocytosis Triggered by Various Signals Is Followed by Endocytosis, Membrane Shedding or Both", Traffic, vol. 8, 2007, pp. 742-757.
D'Asti (Frontiers in Physiology, vol. 3, Article 294, p. 1-15, Jul. 2012) (Year: 2012).
Egger et al., "Protein (Western) Blotting", Molecular Biotechnology, vol. 1, 1994, pp. 289-305.
Ekins and Chu, "Microarrays: their origins and applications", Trends in Biotechnology (1999), 17: 217-218.
Ekins et al., "Multianalyte Microspot Immunoassay-Microanalytical "Compact Disk" of the Future", Clinical Chemistry, vol. 37, No. 11, 1991, pp. 1955-1967.
Ekins, Multi-analyte immunoassay, Journal of pharmaceutical and biomedical analysis, Jan. 1989, pp. 155-168.
European Patent Office, Extended European Search Report (includes Supplementary European Search Report and Search Opinion) received for European Patent Application No. 148007529, mailed on Dec. 7, 2016, 9 pages.
Gaby et al., "Exosomal-Like Vesicles are Present in Human Blood Plasma", International Immunology, vol. 17, No. 7, 2005, pp. 879-887.
Gambim, et al., "Platelet-derived exosomes induce endothelial cell apoptosis through peroxynitrite generation: experimental evidence for a novel mechanism of septic vascular dysfunction", Crit Care 11 (5) R 107 (2007).
Gercel-Taylor, C. et al. (2012). "Nanoparticle Analysis of Circulating Cell-Derived Vesicles in Ovarian Cancer Patients," Analytical Biochemistry 428:44-53.
Gulcher, et al., An alternatively spliced region of the human hexabrachion contains a repeat of potential N-glycosylation sites, PNAS, Mar. 1, 1989, pp. 1588-1592, vol. 86, No. 5.
Hartman, et al., Molecular epidemiology and its current clinical use in cancer management, The Lancent Oncology, Apr. 2010, pp. 383-390, vol. 11, No. 4.
Hegmans et al., "Proteomic Analysis of Exosomes Secreted by Human Mesothelioma Cells", American Journal of Pathology, vol. 164, No. 5, May 2004, pp. 1807-1815.
*Homo sapiens* tenascin C (hexabrachion) {TNC}, mRNA, NCBI Reference Sequence: NM_002160.1, Jun. 26, 2007, available online at https://www.ncbi.nlm.nih.gov/nuccore/NM 002160.1, retrieved on Mar. 22, 2021, 5 pages.
*Homo sapiens* tenascin C (TNC), mRNA, NCBI Reference Sequence: NM_002160.2, Jul. 17, 2011, available online at https://www.ncbi.nlm.nih.gov/nuccore/NM_002160.2, retrieved on Mar. 22, 2021, 5 pages.
*Homo sapiens* tenascin C (TNC}, mRNA, NCBI Reference Sequence: NM_002160.3, Nov. 4, 2018, available online at https://www.ncbi.nlm.nih.gov/nuccore/NM_002160.3, retrieved on Mar. 22, 2021, 8 pages.
*Homo sapiens* tenascin C (TNC}, mRNA, NCBI Reference Sequence: NM_002160.4, Mar. 7, 2021, available online at https://www.ncbi.nlm.nih.gov/nuccore/NM_002160.4, retrieved on Mar. 22, 2021, 10 pages.
Hosseini-Beheshti et al., "Exosomes as Biomarker Enriched Microvesicles: Characterization of Exosomal Proteins a Derived from a Panel of Prostate Cell Lines With Distinct AR Phenotypes", Molecular & Cellular Proteomics, vol. 11, No. 10, 2012, pp. 863-885.
Huang et al. (2001) "Detection of multiple proteins in an antibody-based protein microarray system," Journal of Immunological Methods. 255:1-13.
International Preliminary Report on Patentability received for PCT Patent Application No. PCT/US2014/038615, mailed on Dec. 3, 2015, 8 Pages.
United States Patent and Trademark Office, International Search Report and Written Opinion received for PCT Patent Application No. PCT/US2014/038615, mailed on Oct. 22, 2014, 11 pages.

Ji et al., "Proteome Profiling of Exosomes Derived from Human Primary and Metastatic Colorectal Cancer Cells Reveal Differential Expression of Key Metastatic Factors and Signal Transduction Components", Proteomics, vol. 13, 2013, pp. 1672-1686.
Joester, et al., Evidence for combinatorial variability of Tenascin-C Isoforms and developmental regulation in the mouse central nervous system, The Journal of Biological Chemistry, Jun. 11, 1999, pp. 17144-17151, vol. 274, No. 24.
Kudou (Protein Expression and Purification, vol. 75, p. 46-54, 2011) (Year: 2011).
Laemmli, "Cleavage of structural proteins during the assembly of the head of bacteriophage T4." Nature (1970); 227: 680-685.
Latysheva et al., Syntenin-1 Is a new Component of Tetraspanin-Enriched Microdomains: Mechanisms and Consequences of the Interaction of Syntenin-1 with CD63, Molecular and Cellular Biology, Oct. 2006, pp. 7707-7718.
MacBeath et al. (2000) "Printing proteins as microarrays for high-throughput function determination," Science, 289:1760-1763.
Malabanan et al., "Platelet-Derived Growth Factor-BB Mediates Cell Migration through Induction of Activating Transcription Factor 4 and Tenascin-C", The American Journal of Pathology, vol. 180, No. 6, Jun. 2012, pp. 2590-2597.
Mears et al., "Proteomic Analysis of Melanoma-Derived Exosomes by Two-Dimensional Polyacrylamide Gel Electrophoresis and Mass Spectrometry", Proteomics, vol. 4, 2004, pp. 4019-4031.
Nagrath et al. Isolation of rare circulating tumour cells in cancer patients by microchip technology, Nature 450 (7173): 1235-1239 (Dec. 2007).
Nies, et al., The complete cDNA sequence of human hexabrachion (Tenascin): A multidomain protein containing unique epidermal growth factor repeats, The Journal of Biological Chemistry, Feb. 15, 1991, pp. 2818-2823, vol. 266, No. 5.
Onorato et al., "Immunohistochemical and ELISA Assays for Biomarkers of Oxidative Stress in Aging and Disease", Annals New York Academy of Sciences, vol. 854, Nov. 1998, pp. 277-290.
Raposo et al., "B Lymphocytes Secrete Antigen-presenting Vesicles," J Exp Med, Mar. 1996, 183(3): 1161-1172.
Reardon et al., "A Pilot Study: 131 I-Antitenascin Monoclonal Antibody 81c6 to Deliver a 44-Gy Resection Cavity Boost", Neuro-Oncology, vol. 10, Apr. 2008, pp. 182-189.
Rudikoff, S. et al., "Single amino acid substitution altering antigen-binding specificity," Proceedings of the National Academy of Sciences, USA, Mar. 1982, 79(6), pp. 1979-1983.
Santa Cruz Biotechnology Inc., "Tenascin-C (300-3): sc-13578", Available Online at https://datasheets.scbt.com/sc-13578.pdf, retrieved on Jan. 25, 2020, 1 page.
Santa Cruz Biotechnology Inc., "Tenascin-C (BC-24): sc-59884", Available Online at https://datasheets.scbt.com/sc-59884.pdf, retrieved on Jan. 25, 2020, 1 page.
Schena et al., "Parallel Human Genome Analysis: Microarray-based Expression Monitoring of 1000 Genes", Proceedings of the National Academy of Sciences, vol. 93, Oct. 1996, pp. 10614-10619.
Schweitzer et al., "Measuring proteins on Microarrays", Current Opinion in Biotechnology, vol. 13, 2002, pp. 14-19.
Sigma-Aldrich, "Sepharose® 2B 60-200 µm Bead Diameter", Available Online at https://www.sigmaaldrich.com/catalog/producUsial/2b300?lang=en®ion=IN, 2019, pp. 1-3.
Sigma-Aldrich, "Tween® 20 Viscous Liquid", Available Online at https://www.sigmaaldrich.com/catalog/producUsial/p1379?lang=en®ion=IN, 2019, pp. 1-4.
Simpson, et al. "Proteomic profiling of exosomes: current perspectives." Proteomics, Oct. 2008, pp. 4083-4099.
Siri, et al., Human tenascin: primary structure, pre-mRNA splicing patterns and localization of the epitopes recognized by two monoclonal antibodies, Nucleic Acids Research, Feb. 11, 1991, pp. 525-531, vol. 19, No. 3.
Taylor and Gercel-Taylor, "MicroRNA signatures of tumor-derived exosomes as diagnostic biomarkers of ovarian cancer." Gynecol Oncol. (2008); 110: 13-21.
Tenascin C (hexabrachion) [*Homo sapiens*], NCBI Reference Sequence: NP_002151.1, Jun. 26, 2007, available online at https://www.ncbi.nlm.nih.gov/protein/NP_002151.1, retrieved on Mar. 22, 2021, 3 paces.

(56) References Cited

OTHER PUBLICATIONS

Tenascin precursor [*Homo sapiens*], NCBI Reference Sequence: NP_002151.2, Mar. 7, 2021, available online at https://www.ncbi.nlm.nih.gov/protein/NP_002151.2, retrieved on Mar. 22, 2021, 7 paces.
Tsumoto (Journal of Chromatography A, vol. 1154, p. 81-86, 2007) (Year: 2007).
Valadi, et al., "Exosome-mediated transfer of mRNAs and microRNAs is a novel mechanism of genetic exchange between cells." Nature Cell Biology (2007); 9: 654-659.
Webber et al., "How Pure are your Vesicles?", Journal of Extracellular Vesicles, vol. 2, No. 19861, 2013, pp. 1-6.
Wubbolts et al., "Proteomic and Biochemical Analyses of Human B Cell-Derived Exosomes. Potential Implications for their Function and Multivesicular Body Formation", Journal of Biological Chemistry, vol. 278, No. 13, Mar. 28, 2003, pp. 10963-10972.
Caby et al., "Exosomal-Like Vesicles are Present in Human Blood Plasma", International Immunology, vol. 17, No. 7, 2005, pp. 879-887.

\* cited by examiner

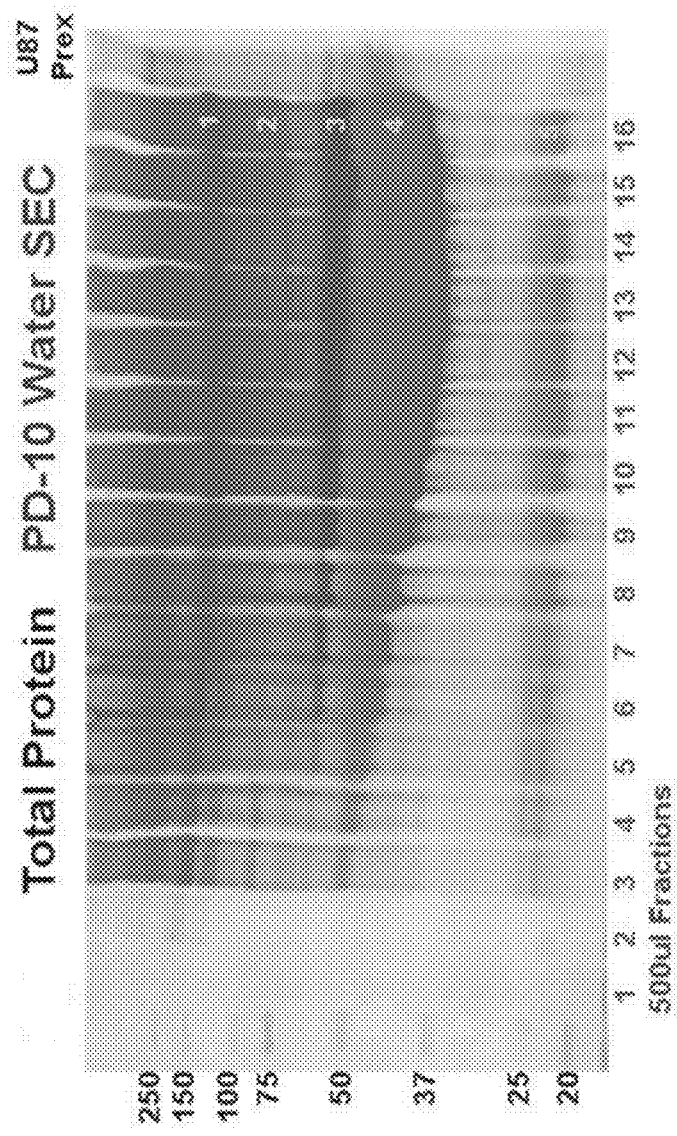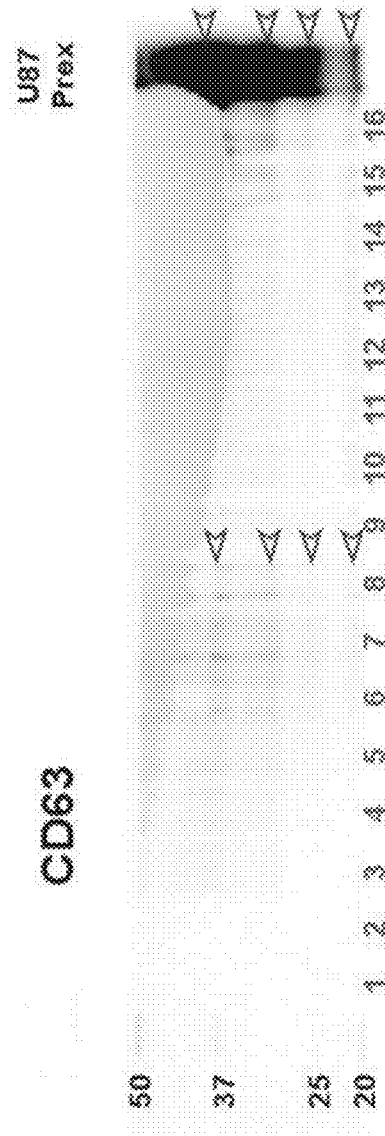
FIG. 4A
FIG. 4B

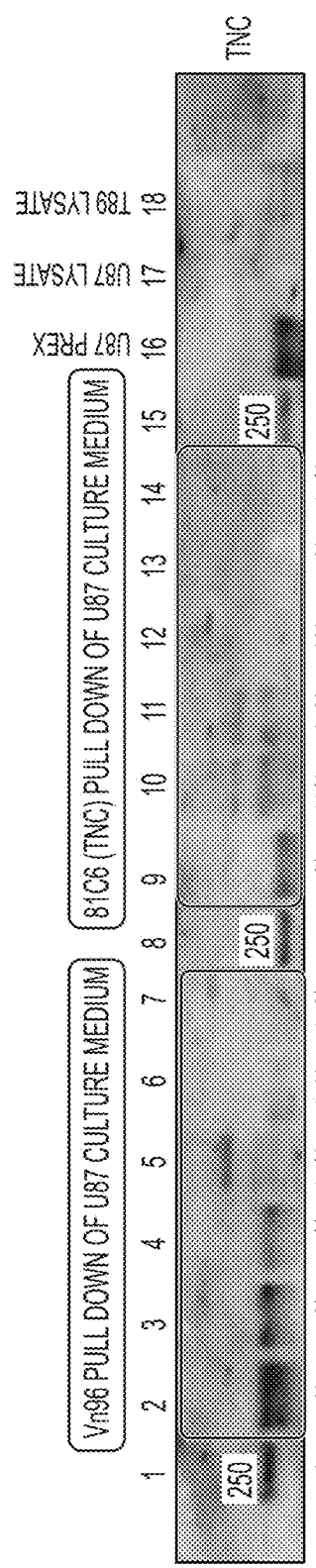
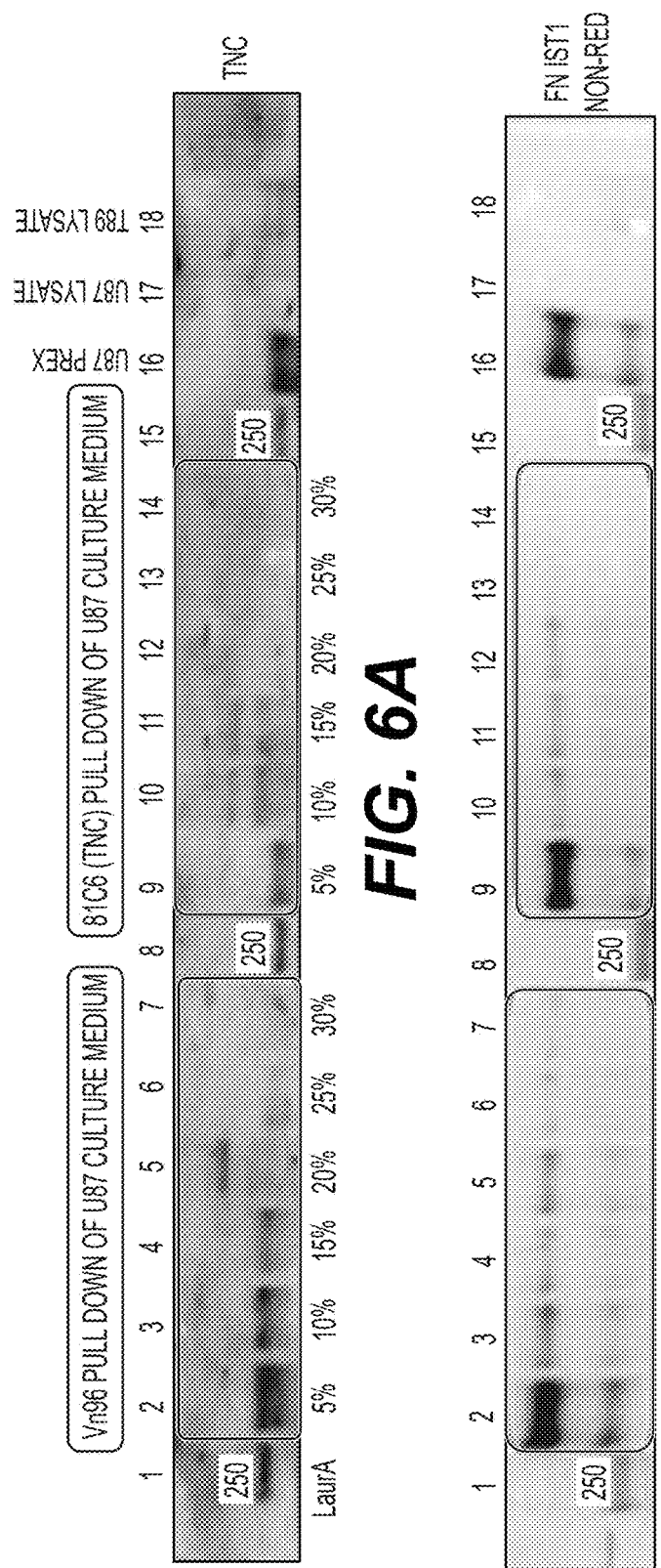
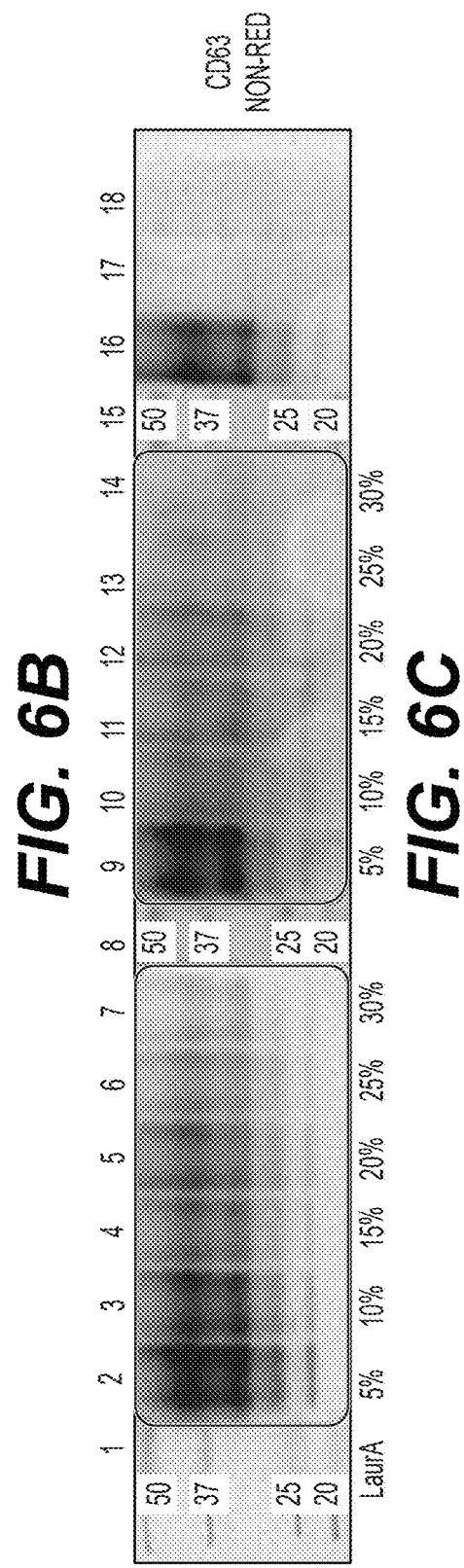
FIG. 6A
FIG. 6B
FIG. 6C

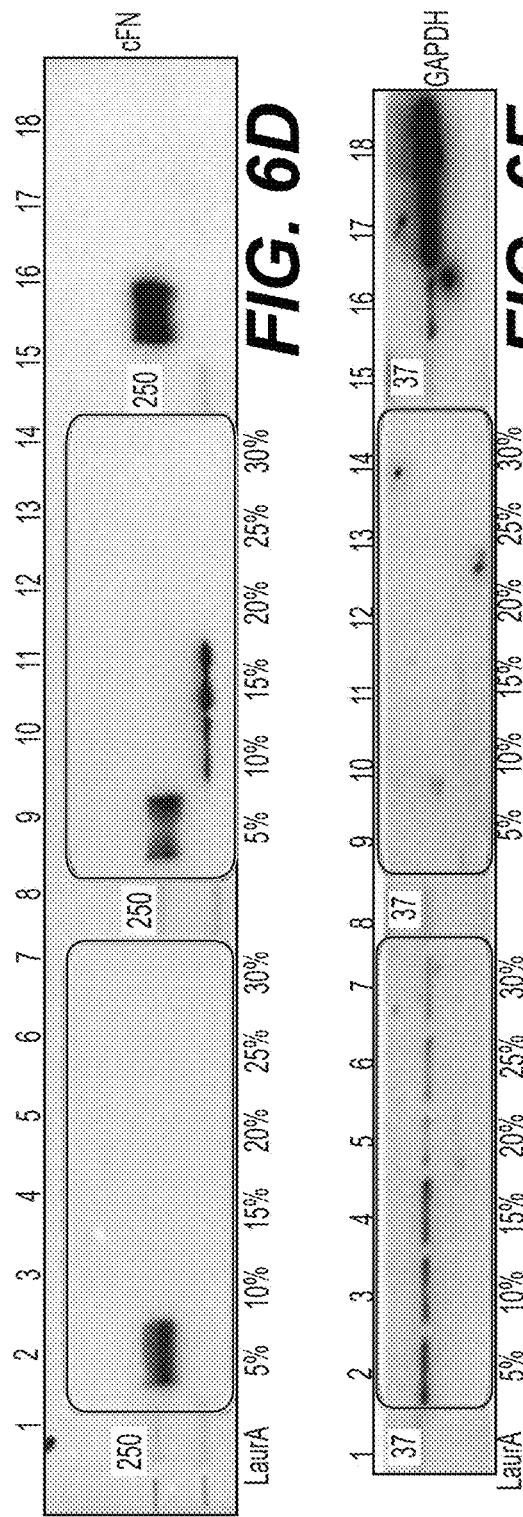
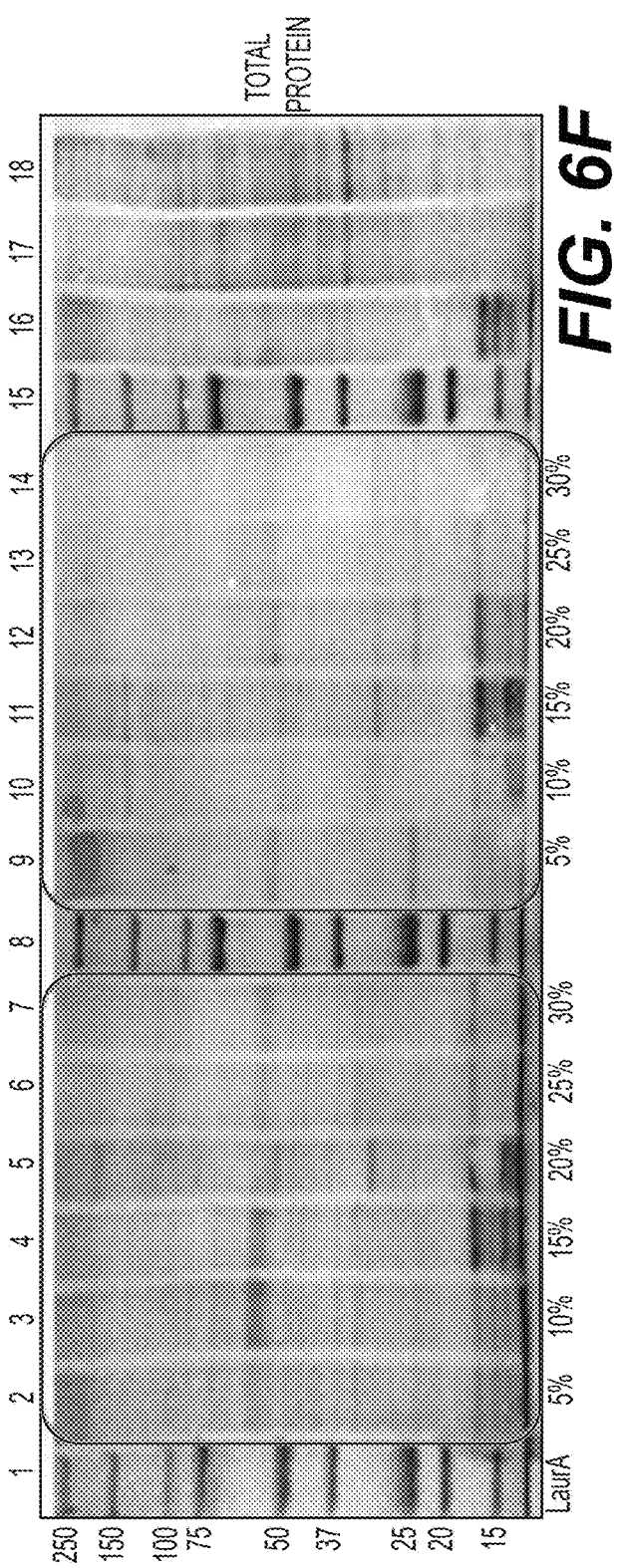

USE OF TENASCIN-C AS AN EXTRACELLULAR MARKER OF TUMOR-DERIVED MICROPARTICLES

CROSS-REFERENCE TO RELATED APPLICATION(S)

This application is a continuation of U.S. patent application Ser. No. 14/893,042 filed Nov. 20, 2015, which is a U.S. National Stage Application under 35 U.S.C. § 371 of International Patent Application No. PCT/US2014/038615 filed May 19, 2014, which claims the benefit of U.S. Provisional Application No. 61/825,951 filed May 21, 2013, the contents of each of which is are incorporated herein by reference in its entirety.

REFERENCE TO AN ELECTRONIC SEQUENCE LISTING

The contents of the electronic sequence listing (NXON_012_02US_SeqList_ST26.xml; Size: 2,003 bytes; and Date of Creation: Oct. 16, 2023) are herein incorporated by reference in its entirety.

FIELD

The present disclosure relates generally to the isolation and analysis of microparticles, and more specifically to the isolation and analysis of tumor-derived microparticles.

BACKGROUND

Cancer is a leading cause of death worldwide. In 2004, it accounted for 7.4 million deaths (around 13% of all deaths). Deaths from cancer are expected to continue to rise, with a predicted 12 million deaths in 2030 (WHO, February 2009). Early detection of cancer and monitoring of the progression of cancer are critical to reducing the worldwide cancer burden, yet the development of robust methods and tools for early detection and monitoring remain major challenges in the field. Furthermore, a large proportion of patients with cancer are over-treated, resulting in wasted time and expense and unnecessary exposure of patients to unpleasant and dangerous side effects (Hartmann et al., *Lancet* 2010, 11:383-390).

For many types of cancers, the current means of diagnosis and monitoring of cancer in the patient involve histopathology of a tissue sample or imaging studies, which involve painful and invasive biopsies or risks associated with imaging such as exposure to radiation. These processes are often expensive and inaccurate due to subjective interpretation by different technicians and clinicians. For example, in diagnosis and classification of gliomas, which account for 80% of all malignant brain/CNS tumors, histopathology and tissue characterization are used. Classification and diagnosis do not, however, lead to successful treatment since typically only 25-50% of patients derive benefit from any given drug therapy.

Thus, an unmet need exists for better experimental tools for the isolation and identification of tumor-derived microparticles, leading to improved methods of detecting and classifying tumors for more accurate and robust diagnosis, prognosis, monitoring of disease progression, and prediction of response to treatment.

BRIEF SUMMARY

In one aspect, the present disclosure provides methods of isolating tumor-derived microparticles from a subject for analysis, including: providing a sample including bodily fluid from a subject; isolating one or more microparticles from the sample; and isolating one or more Tenascin-C positive microparticles from the one or more microparticles in the sample to obtain tumor-derived microparticles. In some embodiments, the tumor-derived microparticles are analyzed to determine the expression status of one or more biomarkers. In some embodiments, the tumor-derived microparticles are analyzed to determine the status of one or more tumor-derived microparticles. In some embodiments, one or more of the tumor-derived microparticles are derived from a tumor arising from a cancer selected from brain cancer, breast cancer, ovarian cancer, lung cancer, and gastrointestinal cancer.

In another aspect, the present disclosure provides methods of identifying tumor-derived microparticles from a subject for analysis, including: providing a sample including bodily fluid from a subject; identifying one or more microparticles from the sample; and identifying one or more Tenascin-C positive microparticles from the one or more microparticles in the sample to identify tumor-derived microparticles. In some embodiments, the tumor-derived microparticles are analyzed to determine the expression status of one or more biomarkers. In some embodiments, the tumor-derived microparticles are analyzed to determine the status of one or more tumor-derived microparticles. In some embodiments, one or more of the tumor-derived microparticles are derived from a tumor arising from a cancer selected from brain cancer, breast cancer, ovarian cancer, lung cancer, and gastrointestinal cancer.

In another aspect, the present disclosure provides methods of isolating brain tumor-derived microparticles from a subject for analysis, including: providing a sample including bodily fluid from a subject; isolating one or more microparticles from the sample; and isolating one or more Tenascin-C positive microparticles from the one or more microparticles in the sample via immunopurification to obtain brain tumor-derived microparticles. In some embodiments, the brain tumor-derived microparticles are analyzed to determine the expression status of one or more biomarkers selected from EGFRvIII, 14-3-3, H2AX, PPIX, and glycoporin A, where the presence of EGFRvIII, the presence of 14-3-3, the presence of H2AX, the presence of PPIX, and the absence of glycoporin A are indicative of brain-tumor derived microparticles.

In another aspect, the present disclosure provides methods of diagnosing brain cancer in a subject, including: providing a sample including bodily fluid from a subject; isolating one or more microparticles from the sample; isolating one or more Tenascin-C positive microparticles from the one or more microparticles in the sample to obtain tumor-derived microparticles; determining the expression status of one or more biomarkers in the tumor-derived microparticles; and diagnosing brain cancer in the subject based on the expression status of the one or more biomarkers. In some embodiments, the expression status of the one or more biomarkers is selected from EGFRvIII, 14-3-3, H2AX, PPIX, and glycoporin A, where the presence of EGFRvIII, the presence of 14-3-3, the presence of H2AX, the presence of PPIX, and the absence of glycoporin A are indicative of brain tumor-derived microparticles.

In some embodiments that may be combined with any of the preceding embodiments, the bodily fluid is selected from blood, serum, plasma, urine, saliva, and cerebrospinal fluid. In some embodiments that may be combined with any of the preceding embodiments, the microparticles are isolated using a solid support. In some embodiments, the solid support is a column. In some embodiments, the column is a Sepharose™ 2B column. In some embodiments that may be combined with any of the preceding embodiments, a mobile phase is added to the solid support. In some embodiments that may be combined with any of the preceding embodiments, the mobile phase is water. In some embodiments that may be combined with any of the preceding embodiments, the mobile phase includes an amino acid. In some embodiments, the mobile phase includes arginine. In some embodiments that may be combined with any of the preceding embodiments, the solid support includes a HDN peptide. In some embodiments that may be combined with any of the preceding embodiments, the solid support includes a Vn96 peptide. In some embodiments that may be combined with any of the preceding embodiments, the Tenascin-C positive microparticles are isolated using a solid support. In some embodiments that may be combined with any of the preceding embodiments, the solid support includes an anti-Tenascin-C antibody. In some embodiments that may be combined with any of the preceding embodiments, the biomarkers are selected from EGFRvIII, HER-2, MET, K-ras, c-myc, PI3K, Akt, BRCA, PTEN, and VEGFR. In some embodiments that may be combined with any of the preceding embodiments, the expression status of the biomarkers is determined by Western blot or mass spectrometry. In some embodiments that may be combined with any of the preceding embodiments, the microparticle characteristics are the number of Tenascin-C positive microparticles relative to the total microparticles isolated or the concentration of Ten-C positive microparticles. In some embodiments that may be combined with any of the preceding embodiments, analyzing the tumor-derived microparticles is used to diagnose cancer, prognose cancer, and/or monitor the progression or recurrence of cancer. In some embodiments that may be combined with any of the preceding embodiments, the Tenascin-C positive microparticles are isolated by direct affinity pulldown. In some embodiments, the Tenascin-C positive microparticles are contacted with an anti-Tenascin-C antibody. In some embodiments, the anti-Tenascin-C antibody is 81C6. In some embodiments that may be combined with any of the preceding embodiments, one or more microparticles isolated from the sample are incubated with a solution including LaurA. In some embodiments, the solution includes about 5% LaurA. In some embodiments that may be combined with any of the preceding embodiments, one or more microparticles isolated from the sample are contacted with a solution including arginine and glutamine. In some embodiments, the arginine and glutamine are present in the solution at substantially equal concentrations. In some embodiments, the concentration of arginine and glutamine is 1 M. In some embodiments that may be combined with any of the preceding embodiments, one or more microparticles isolated from the sample are contacted with a solution comprising arginine and ethanol. In some embodiments that may be combined with any of the preceding embodiments, one or more microparticles isolated from the sample are contacted with a solution comprising 1 M arginine buffer.

DESCRIPTION OF THE FIGURES

FIG. 4A illustrates a gel blot analysis of serum-derived total protein isolated from sequential 500 μl fraction eluates (labeled 1-14) from an SEC column using water as the mobile phase. FIG. 4B illustrates a Western blot analysis of CD63 protein present in the sequential fractions from the same numbered fractions shown in FIG. 4A.

FIG. 6A illustrates a blot analysis of Tenascin-C (TNC) protein isolated from Vn96 or 81C6 pulled down microparticle samples. FIG. 6B illustrates a blot analysis of total fibronectin protein isolated from Vn96 or 81C6 pulled down microparticle samples. FIG. 6C illustrates a blot analysis of CD63 (CD63 Tetraspanin LAMP3) protein isolated from Vn96 or 81C6 pulled down microparticle samples. FIG. 6D illustrates a blot analysis of oncofetal fibronectin protein isolated from Vn96 or 81C6 pulled down microparticle samples. FIG. 6E illustrates a blot analysis of glyceraldehyde phosphate dehydrogenase (GADPH) isolated from Vn96 or 81C6 pulled down microparticle samples. FIG. 6F illustrates a blot analysis of total protein isolated from Vn96 or 81C6 pulled down microparticle samples.

DETAILED DESCRIPTION

Figure 1A:
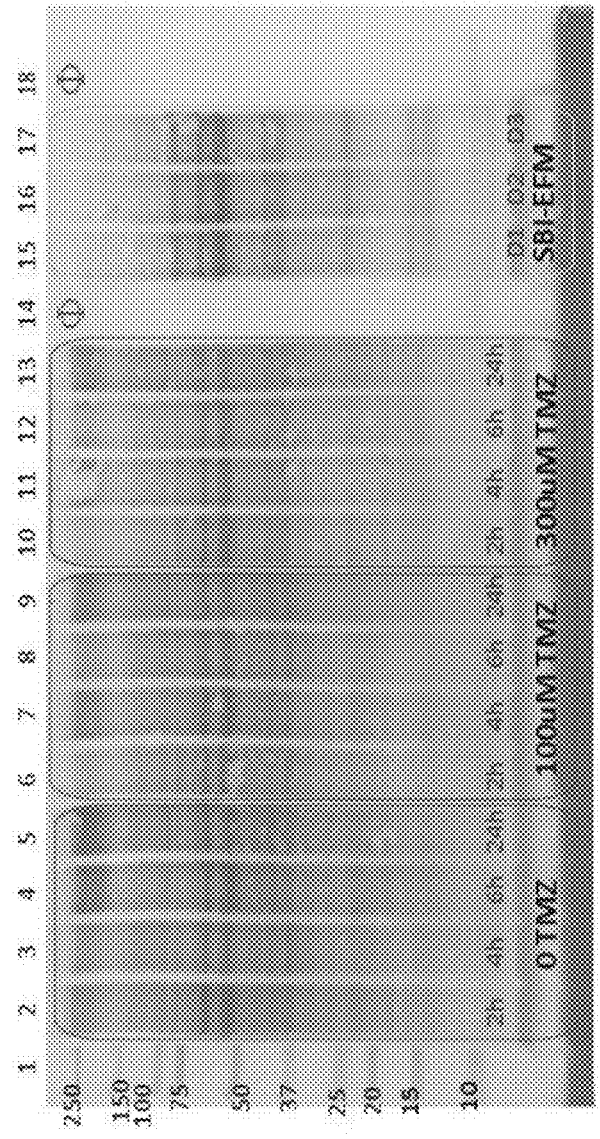
FIG. 1A illustrates a gel blot analysis of total protein content isolated from microparticles derived from U87 brain tumor cells that were grown in a nutrient-rich media (SBI-EFM) (Flask A). The total protein content from the various microparticle samples is shown as a function of time or exposure to the chemotherapeutic agent temozolomide (TMZ).

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The present disclosure relates to methods of isolating tumor-derived microparticles from a subject for analysis, such as by isolating Tenascin-C positive microparticles from a sample from the subject.

In particular, the present disclosure is based, at least in part, on Applicants' discovery that Tenascin-C protein is robustly associated with microparticles shed from U87 cells, which are a model for glioma (brain cancer). Applicants have demonstrated that Tenascin-C protein abundance in tumor-derived microparticles is remarkably stable, even in the presence of proteolytically challenging environments. Further, tumor cells exposed to genotoxins and grown in nutrient-deprived media continued to shed microparticles that robustly accumulate Tenascin-C. These observations suggest Tenascin-C may be used as a stable marker for tumor-derived microparticles even in challenging environments that may impact the availability and use of other markers.

Accordingly, Applicants disclose herein methods of isolating tumor-derived microparticles by isolating Tenascin-C-containing (Tenascin-C positive) microparticles to thus obtain the tumor-derived microparticles. Tumor-derived microparticles may be subject to subsequent analysis such as, for example, determining the expression status of biomarkers in the tumor-derived microparticles and/or determining additional characteristics of the tumor-derived microparticles. Such analysis of the isolated tumor-derived microparticles may be informative with regard to various clinical approaches such as, for example, tumor diagnosis, classification, monitoring, and assessment of therapeutic efficacy.

Definitions

In order to facilitate an understanding of the disclosure, selected terms used in the application will be discussed below.

"Diagnosis" as used herein may refer to the identification of a disease or likelihood of a disease in a test subject. In particular, "diagnosing cancer" as used herein may refer to the identification of cancer in a test subject not previously known to have cancer or to the determination of whether a test subject has an increased likelihood or probability of having cancer. "Diagnosing cancer" may refer to the identification or prediction of increased likelihood of a specific type of cancer in a test subject and may be based on information from multiple biomarkers, such as the expression levels of the protein biomarkers disclosed herein, cancer stage, tumor grade, age, physical symptoms, and medical history.

"Monitoring" as used herein may refer to the act of observing. Monitoring may include, for example, observing the expression level of a protein in a microparticle. Monitoring may also refer to the observation of a physical characteristic such as, for example, the number of microparticles in a sample.

"Microparticle" as used herein may refer to any small vesicle released from any cell type. Microparticles include, for example, endosome-derived exosomes, plasma membrane-derived shedding vesicles, apoptotic bodies, prostasomes, P2 and P4 particles, and outer membrane vesicles (OMVs). Microparticles may also be referred to as ectosomes, shedding bodies, exovesicles, or secretory vesicles.

A "microparticle-associated protein" as used herein may refer to any protein that has been contained within or located on the surface of a microparticle. "Microparticle-associated protein" may refer to such a protein while the protein is still associated with a microparticle or after the protein is no longer associated with a microparticle. A "microparticle-associated protein" may refer to a protein associated with a microparticle irrespective of the origin of the microparticle and may include, for example, a protein associated with a tumor-derived microparticle. An exemplary microparticle-associated protein may include, for example, Tenascin-C.

"Prognosis" as used herein may refer to the likely outcome of an illness. A prognosis may include, for example, the expected survival time and description of the course of the illness over time.

"Tenascin-C" as used herein may refer to the protein encoded by the TNC (Tenascin-C) gene in humans involved in extracellular matrix protein-mediated signaling. "Tenascin-C" may also refer to all variants or derivatives, such as, for example, splice variants and post-translational modifications, homologs, orthologs, and paralogs of Tenascin-C.

Methods of Isolating Tumor-Derived Microparticles

The present disclosure provides methods for isolating tumor-derived microparticles. Isolation of tumor-derived microparticles involves contacting microparticles in a general microparticle population isolated from a sample with a tumor-derived microparticle-specific reagent. In some preferred embodiments, the tumor-derived microparticle-specific reagent is a reagent which specifically isolates microparticles containing Tenascin-C. Isolation of Tenascin-C positive microparticles thus results in obtaining tumor-derived microparticles. Tumor-derived microparticles may be further analyzed to gain additional information about the tumor cell from which the tumor-derived microparticle originated.

Samples Containing a Bodily Fluid

The methods of the disclosure involve providing a sample containing a bodily fluid from a subject. The bodily fluid can be used as a source of microparticles to obtain tumor-derived microparticles.

Various samples containing a bodily fluid from a subject will be apparent to one of skill in the art and may be used in the methods disclosed herein. A bodily fluid may refer to, for example, a sample of fluid isolated from anywhere in the body of the subject, preferably a peripheral location, including but not limited to, for example, blood, plasma, serum, urine, sputum, spinal fluid, pleural fluid, nipple aspirates, lymph fluid, respiratory droplets, intestinal, and genitourinary tracts, tears, saliva, breast milk, fluid from the lymphatic system, semen, cerebrospinal fluid, intra-organ system fluid, ascitic fluid, tumor cyst fluid, synovial fluid, amniotic fluid, ocular fluid, ascites, bronchoalveolar lavage, and combinations thereof. In some preferred embodiments, the sample is blood. If the sample is blood, is it preferably centrifuged to remove cellular material and debris such that a plasma or serum fraction is generated.

Subjects

The sample containing a bodily fluid as described herein is obtained from a subject. A subject of the present disclosure may be, for example, a cancer patient. Other subjects may include, for example, an individual suspected of having cancer or a subject to be screened with the goal of obtaining a cancer diagnosis. Additional subjects may include, for example, a cancer patient in need of monitoring of the progression of the cancer or in need of determination of the efficacy of cancer treatment. Various subjects that are applicable to the methods of the present disclosure will be readily apparent to one of skill in the art.

Isolation of Microparticles from the Sample

The methods of the present disclosure involve isolating microparticles from a sample. In some embodiments, isolation of microparticles from the sample involves the preliminary isolation of the entire population of microparticles from the sample. In other embodiments, various different populations of microparticles may be isolated from the sample. For example, a specific sub-population of microparticles from the sample may be isolated. The sub-population may include tumor-derived microparticles as well as non-tumor-derived microparticles.

Total Microparticle Population

The entire population of microparticles may be isolated from the sample according to any methods known to one of skill in the art (see, for example, Cocucci et al., *Traffic* 8, 2007:742-757; Simpson et al., *Proteomics* 8, 2008:4083-4099). In certain embodiments, isolating microparticles involves centrifugation. For example, serial centrifugation may be used to remove cells and debris, and microparticles may be pelleted using sedimentation at 60-100,000×g for 1 hour or longer. Additional methods of differential centrifugation are described in Raposo et al., *J Exp Med* 183, 1996:1161-72. In other embodiments, techniques such as filtration, sucrose density gradients, organelle electrophoresis, anion exchange and/or gel permeation chromatography, magnetic activated cell sorting (MACS), nanomembrane ultrafiltration concentration, and microchips with microfluidic technology may be used to isolate microparticles from the sample. For example, large cell debris may be removed by filtration with a 0.22 µm or a 0.1 µm filter. Microparticles may be isolated by passing the sample through a filter having an average pore diameter of between 0.01 µm and about 0.15 µm. Linear sucrose gradients (2.0-0.25 M sucrose), or a combination of ultrafiltration (500 K membrane) and ultracentrifugation into a 30% sucrose/deuterium oxide (98%) cushion (density, 1.210 g/cm$^3$) may also be used. Various methods for the isolation of microparticles can be found, for example, in U.S. Pat. Nos. 6,899,863, 6,812,023, Taylor and Gercel-Taylor, *Gynecol Oncol* 110, 2008:13-21, Cheruvanky et al., *Am J Physiol Renal Physiol* 292, 2007: F1657-61, and Nagrath et al., *Nature* 450, 2007:1235-9.

Microparticles may also be isolated from a sample using affinity capture methods. Preferably, these affinity methods are immunoaffinity methods, but in certain embodiments, such methods employ other reagents which bind specifically to proteins.

The entire population of microparticles may be isolated by contacting samples containing microparticles with a reagent specific to a protein commonly found on the surface of all microparticles regardless of origin (i.e., microparticle-specific reagents). In certain embodiments, the reagents are specific to the following proteins: membrane adhesion proteins (integrins), membrane transport/trafficking proteins (annexins and Rab proteins, such as Rab guanosine triphosphatase), cytoskeletal components (actin, tubulin, ERM proteins, lysosomal markers, and tetraspanin proteins, such as CD9, CD63, CD81, and CD82), antigen presenting proteins (HLA class I and II), death receptors, cytokines and cognate receptors (TNF, TNFR1, and TGF-β), iron transport proteins, enzymes (enolase), cytosolic proteins (Hsc73 and Hsc90), subunits of trimeric G proteins, Tsg101, milk-fat globule (MFG)-E8, lactadherin, MHC class I molecules, heat shock proteins (Hsp70 and Hsp90), drug transporter proteins, or signal transduction proteins. Reagents specific for lipids on the surface of microparticles may also be used. For example, in some embodiments, the immunoaffinity capture includes use of an anti-phosphatidylserine antibody which binds to microparticles having phosphatidylserine molecules with the polar side of the molecule exposed on its outer surface. The antibody is preferably monoclonal, but can also be polyclonal. In certain preferred embodiments, the microparticle-specific reagent used to isolate microparticles from the sample is a Heladonin (Hdn) peptide or a Vn96 peptide. A Vn96 peptide has the reverse peptide sequence of an Hdn peptide.

Microparticle Sub-Populations

In certain embodiments, reagents are specific to markers of sub-populations of microparticles from specific cell types. Examples include class II MHC and co-stimulatory molecules (CD86) from antigen-presenting cells, von Willebrand factor or CD41a (GPIIb) from platelets, TCR from T-cells, or perforin or granzyme from cytotoxic T cells (Caby et al., *Inter Immunol* 17 (7); 879-887; 2005). In other embodiments, a specific sub-population of microparticles may include, for example, those microparticles derived from endosomes or those derived from plasma membrane.

The microparticles, either in isolated form or found in the sample, can be contacted with a tissue-specific reagent to isolate microparticles derived from a specific tissue. Exemplary tissues of interest may include, for example, brain, adrenal gland, endocrine gland, pituitary, hypothalamus, parathyroid, uterus, heart, blood vessel, stomach, trachea, pharynx, gums, hair, scalp, subcutaneous tissue, Fallopian tube, reproductive tract, urethra, skin, bone, stem cell, umbilical cord, placenta, lymphocyte, monocyte, macrophage, formed blood cell, smooth muscle, skeletal muscle, connective tissue, spinal cord, kidney, bladder, anus, bone, breast, prostate, lung, cervix, colon, rectum, uterus, esophagus, skin, liver, pharynx, mouth, neck, ovary, pancreas, lung, eye, intestine, mouth, thyroid, GI tract, and endometrium.

In certain embodiments, microparticles may be isolated from the sample with an organelle-specific reagent to isolate the microparticles derived from organelles of cells in a specific tissue. Particular organelles of interest may include, for example, plasma membrane, peroxisome, smooth ER, rough ER, lysosome, mitochondria, and nucleus. In some embodiments, each step is performed using multiple microparticle-specific reagents.

In some embodiments, the entire population of microparticles from the sample is contacted with a reagent which binds to microparticles derived from multiple tissue types rather than one that binds microparticles derived from a specific tissue.

In preferred methods for isolating microparticles derived from specific tissue(s), the method includes contacting a sample with a reagent specific for microparticles, preferably a reagent specific for phosphatidylserine, where the sample includes microparticles and the reagent binds to microparticles; contacting the microparticles with a tissue-specific reagent and then isolating the microparticles derived from the tissue(s).

Isolation of Tumor-Derived Microparticles

The methods of the present disclosure involve the isolation of tumor-derived microparticles. Once a population of microparticles has been isolated from a sample, these isolated microparticles are subjected to further selection steps to isolate only the tumor-derived microparticles from the more general microparticle population isolated from the sample.

Methods of isolating tumor-derived microparticles as described herein involve contacting microparticles isolated from a sample with other reagents that bind specifically to microparticles which are derived from a tumor cell (i.e., tumor-derived microparticle-specific reagents). For example, Tenascin-C, as disclosed herein, is a marker of tumor-derived microparticles and therefore isolation of Tenascin-C positive microparticles from the general microparticle population results in obtaining tumor-derived microparticles from the sample.

Isolation of Tenascin-C positive microparticles from a microparticle population may be achieved using various techniques known to one of skill in the art and as described herein. For example, a reagent that binds specifically to microparticles containing Tenascin-C (i.e. a Tenascin-C specific reagent) may be used. A Tenascin-C specific reagent may include, for example, an anti-Tenascin-C antibody. Exemplary anti-Tenascin-C antibodies that may be used in the methods disclosed herein may include, for example, Tenascin-C (E-9) (Catalog number: sc-25328), Tenascin-C (H-300) (Catalog number: sc-20932), Tenascin-C (N-19) (Catalog number: sc-9871), Tenascin-C (F-17) (Catalog number: sc-9872), Tenascin-C (300-3) (Catalog number: sc-13578), and Tenascin-C (BC-24) (Catalog number: sc-59884); all of which are commercially available from Santa Cruz Biotechnology (Santa Cruz, CA). In some preferred embodiments, the Tenascin-C specific reagent used to isolate Tenascin-C positive microparticles is the 81C6 anti-Tenascin-C antibody (see Example 1).

In some embodiments, methods for isolating Tenascin-C positive microparticles derived from a blood sample include the steps of providing blood; providing plasma by centrifuging the blood; contacting plasma with a microparticle-specific reagent such as an Hdn peptide, where the microparticle-specific reagent binds to microparticles; isolating microparticles bound by the microparticle specific reagent to obtain isolated microparticles; contacting the isolated microparticles with an anti-Tenascin-C antibody such as 81C6; and isolating the Tenascin-C positive microparticles to obtain tumor-derived microparticles from the blood sample.

In some embodiments, methods of isolating Tenascin-C positive microparticles may involve direct affinity pulldown of the Tenascin-C positive microparticles from a sample. Direct affinity pulldown may be performed without the need for beads, resins, or other support reagents. Direct affinity pulldown may involve direct centrifugation of a sample after such sample has been contacted with, for example, an anti-Tenascin-C antibody to isolate Tenascin-C positive microparticles. Direct affinity pulldown may also involve contacting a sample with a microparticle-specific reagent, such as the Hdn or Vn96 peptide, to isolate microparticles, which may then be contacted with an anti-Tenascin-C antibody to isolate Tenascin-C positive microparticles from the total microparticle population.

While a Tenascin-C-specific reagent is preferably used to isolate tumor-derived microparticles from a microparticle population, other reagents that can isolate tumor-derived microparticles may also be used. Exemplary tumor-derived microparticle-specific reagents include antibodies specific to tumor cell surface proteins or tumor antigen proteins. In certain embodiments, these proteins include tumor surface antigens, tumor invasion-related proteins, angiogenesis proteins, immune-suppressing cytokines, integrin proteins, and proteases. Several studies have identified proteins specific to microparticles derived from various tumor types (see, for example, Bard, M P et al., *Am J Respir Cell Mol Biol.* 2004 31 (1): 114-21; Hegmans, J P et al., *Am J Pathol.* 2004; 164 (5): 1807-15; Mears, R et al., *Proteomics.* 2004; 4 (12): 4019-31; and Choi, D S et al., *J Proteome Res.* 2007; 6 (12): 4646-55). These antibodies are preferably monoclonal, but can also be polyclonal. In some embodiments, the tumor-derived microparticle-specific reagent is a reagent specific certain proteins such as, for example, IDH1, PDGFRalpha, or $\alpha_V/\beta_{III}$ integrin.

In some embodiments, other tumor-derived microparticle-specific reagents may be used to isolate tumor-derived microparticles. Such reagents may include antibodies which can specifically bind to a tumor-associated protein. Such proteins may include, for example, EGFRvIII, EGFR, HER-2, HER-3, HER-4, MET, cKit, PDGFR, Wnt, beta-catenin, K-ras, H-ras, N-ras, Raf, N-myc, c-myc, IGFR, PI3K, Akt, BRCA1, BRCA2, PTEN, FGFR3, EphB2, ROR1, EphA2, EphA4, VEGFR-2, VEGFR-1, Tie-2, TEM-1 and CD276, ErbB3, ErbB4, FGFR1, FGFR4, InsulinR, IGF-1R, Dtk, Mer, MSPR, c-Ret, ROR1, ROR2, Tie-1, Tie-2, TrkA, TrkB, VEGFR3, EphA1, EphA7, EphB2, and EphB4.

In other embodiments, the tumor-derived microparticle-specific reagent only binds to tumor-derived microparticles derived from certain tissue types. In this case, the tumor-derived microparticle-specific reagent is also a tissue-specific reagent.

Affinity Purification of General Microparticles and Tumor-Derived Microparticles When microparticles described in the present disclosure are isolated from a sample, such isolation may involve subjecting the microparticles to affinity purification. Reagents which bind specifically to microparticles and/or which bind specifically to tumor-derived microparticles allow for capture of these microparticles and subsequent affinity purification.

Contacting the sample containing microparticles or the isolated microparticles with affinity purification reagents occurs for a suitable incubation time which optimizes the efficiency of the microparticle: reagent interaction. It is well within the competence of one of ordinary skill in the art to determine the particular conditions based on the disclosure herein. Typically, the sample containing the microparticles or the isolated microparticles are incubated with the affinity purification reagents together in a suitable buffer at physiological pH at a suitable temperature (e.g., about 4-37° C.), for a suitable time period (e.g., about 60 minutes to overnight) to allow the binding to occur.

Once bound by reagent, microparticles are isolated using standard methods known to those of skill in the art. For example, if the microparticles are bound to an immunoaffinity resin, the resin is washed with physiological buffers, such as Tris-Acetate pH 7.6 to remove other unbound components of the sample and then eluted by changing the ionic strength of the buffer for the resin, for example, by gradually increasing the concentration of a salt, such as NaCl, $CaCl_2$), KCl, $MgCl_2$, or similar salts that cause the reagent to release the bound microparticles.

The reagents are typically coupled to solid supports. A solid support, for purposes of the present disclosure, may be any material that is an insoluble matrix and can have a rigid or semi-rigid surface to a reagent can be linked or attached. Exemplary solid supports include, for example, substrates such as nitrocellulose, polyvinylchloride; polypropylene, polystyrene, latex, polycarbonate, nylon, dextran, chitin, sand, silica, pumice, agarose, cellulose, glass, metal, polyacrylamide, silicon, rubber, polysaccharides, polyvinyl fluoride, diazotized paper, activated beads, magnetically responsive beads, and any materials commonly used for solid phase synthesis, affinity separations, purifications, hybridization reactions, immunoassays and other such applications. The support may be particulate or may be in the form of a continuous surface and includes membranes, mesh, plates, pellets, slides, disks, capillaries, hollow fibers, needles, pins, chips, solid fibers, gels (e.g. silica gels) and beads, (e.g., pore-glass beads, silica gels, polystyrene beads optionally cross-linked with divinylbenzene, grafted co-poly beads, polyacrylamide beads, latex beads, dimethylacrylamide beads optionally crosslinked with N—N'-bis-acryloylethylenediamine, iron oxide magnetic beads, and glass particles coated with a hydrophobic polymer.

Typically, the solid support is a bead or resin in a column configuration. In some immunoaffinity capture methods for isolating microparticles of interest, the method includes providing a column, applying a sample suspected of containing one or more of the microparticles of interest to bind to resins in the column, washing the column, eluting the resins and analyzing the eluant for the presence of the microparticles of interest. More specifically, such methods may include loading the column with a predetermined amount of a sample suspected of containing the microparticles of interest in either blood plasma or a physiological buffer; binding the microparticles to the reagent on the column; loading the column with a wash solution, suspending the resin in the wash solution; removing the wash solution from the column; eluting the microparticles in eluant; and analyzing the eluant for the presence of the microparticles.

In certain embodiments, it is preferred that that the column configuration used in such methods allows for suspension of the resin beads, such as a mobile bead column or other resin during washing. It has been discovered that such a column configuration results in significantly lower levels of background and hence more sensitive levels of quantitation and overall yield of the desired target.

In certain embodiments, the column used in such methods includes a lower end including an outflow opening; a lower porous support; a layer of resin on the lower porous support, the resin having specific affinity for all microparticles or tumor-derived microparticles; an upper porous support; and an upper end including an inflow opening; wherein the resin between the lower porous support and the upper porous support is structured and arranged to permit removal of the upper porous support from the column without substantial removal of resin.

In other embodiments, the resin is fixed between two semi-porous frits such that the resin beads may be suspended and such that the upper frit may be removed during washing of the resin to remove background compounds.

The volume of the resin in the column may vary but is typically less than the total packed volume of the column between the lower porous support and the upper porous support. Preferably, the volume of the resin in the column is no greater than 50%, more preferably no greater than 40%, even more preferably no greater than 30%, still more preferably no greater than 25%, and still more preferably no greater than 20% of the total packed volume of the column between the lower porous support and the upper porous support.

In some embodiments, a sample containing microparticles may be subjected to treatment with a LaurA solution prior to isolation of the microparticles. "LaurA" is a protein solubilizing buffer and is composed of lauroyl glutamate and arginine. In some embodiments, the LaurA solution is composed of 1% v/v lauroyl glutamate and 0.8M arginine. LaurA solutions may be mixed with a microparticle sample to give a final percentage concentration of LaurA in the sample. The percentage of LaurA solution present in a sample may include, for example, about 5%, about 10%, about 15%, about 20%, or about 25% or more LaurA solution present in the sample.

Samples containing microparticles may also be contacted with a variety of arginine-containing solutions. In some embodiments, a sample containing microparticles is incubated with a solution that includes arginine and glutamine. In some embodiments, the solution that includes arginine and glutamine includes equal concentrations of arginine and glutamine. For example, the solution may include 1M arginine and glutamine. In some embodiments, a sample containing microparticles is incubated with a solution that includes arginine an ethanol. In some embodiments, the sample that includes arginine and ethanol includes equal concentrations of arginine and ethanol. In some embodiments, a sample containing microparticles is incubated with a solution that includes an arginine buffer. In some embodiments, the sample is incubated with 1 M arginine buffer. The sample containing microparticles that is contacted with an arginine-containing solution may contain substantially isolated microparticles (e.g. a sample of microparticles following recovery with a microparticle recovery peptide, such as Vn96, or with an anti Tenascin-C antibody).

In some preferred embodiments, a two-step purification for the enrichment of microparticles from a sample may be performed. In some preferred embodiments, purification of the microparticles involves the use of a Sepharose™ column, either large or small, such as a Sepharose™ 2B column, for the purpose of using size exclusion chromatography techniques to isolate microparticles from a sample. In some embodiments, the column contains an agarose slurry.

In a first purification step, water may be used as a first mobile phase. In one embodiment, a microparticle-containing sample such as serum, for example, is added to the column and water is used as the mobile phase. Microparticles may remain associated with the column, while other components of the sample are eluted from the column through a series of washing and elution steps. In embodiments where the sample contains serum, the water washes may be configured such that high abundance serum proteins are eluted from the column while microparticles remain associated with the column.

In a second purification step, a solution containing an amino acid may be used as the mobile phase. In one embodiment, following the first series of elutions using water as the mobile phase, a solution containing an amino acid is added to the column. Amino acids are well-known in the art and will be apparent to one skilled in the art. In some preferred embodiments, the solution contains the amino acid arginine (an arginine-containing solution). Addition of a solution containing an amino acid to the column such as, for example, an arginine-containing solution, may promote elution of the microparticles from the column to obtain microparticle-containing fractions.

Various modifications to the described two-step purification protocol will be readily apparent to one skilled in the art in view of the present disclosure. For example, the number of elution steps may be modified or adjusted to meet specific purposes. The column may be decorated with reagents that assist in microparticle capture, such as an Hdn peptide or a Vn96 peptide. In some embodiments, both the first step and the second step use a solution containing an amino acid as the mobile phase on the column. In some embodiments, both the first step and the second step use an arginine-containing solution as the mobile phase on the column. The concentration of arginine in the arginine-containing solution may be modified to meet specific purposes.

The two-step process as described above may allow for microparticle enrichment that is easily accessible for downstream microparticle analysis. This purification process may serve to remove excess background protein and lipid from serum, plasma, and other microparticle-containing samples. The purification is non-denaturing and yields an enriched sample of microparticles, without inhibitors or resins. The enriched microparticle fraction may be further analysed for elements of specific origin without the general problem of steric inhibition by lipids and high abundance proteins. Further, the purification allows for bench top methods such as ELISA and magnetic beads, in addition to more sophisticated but high throughput technologies such as protein mass spectrometry and profiling by nuclear magnetic resonance (NMR).

In an exemplary embodiment, a serum sample from a subject is subjected to a two-step purification process to isolate the microparticle population from the serum. The serum is loaded onto a Sepharose 2B™ column containing an agarose slurry. Water is added as a first mobile phase to elute predominant serum proteins. An arginine-containing solution is subsequently added to the column to elute microparticles present in the serum. The eluted sample containing serum-derived microparticles may then be subject to affinity purification by contacting the isolated microparticle-containing sample with a Tenascin-C specific reagent, such as the 81C6 anti-Tenascin-C antibody. Purification of this sample yields isolated tumor-derived microparticles. These tumor-derived microparticles may then be subject to various analyses as described herein.

Methods of Identifying Tumor-Derived Microparticles

The present disclosure further provides methods for identifying tumor-derived microparticles in a sample. Methods of identifying tumor-derived microparticles include providing a sample containing a bodily fluid from a subject, isolating microparticles from the sample, and identifying tumor-derived microparticles from the sample. In some preferred embodiments, identifying Tenascin-C positive microparticles in the sample results in identifying tumor-derived microparticles. Identification of tumor-derived microparticles need not involve an isolation step as described above. Accordingly, the methods disclosed herein further relate to the identification of tumor-derived microparticles in a sample.

Various methods may be used to identify tumor-derived microparticles and will be readily apparent to one skilled in the art in view of the present disclosure. For example, a flow cytometry technique involving the visual observation of Tenascin-C containing microparticles amongst a more general microparticle population may be accomplished with the aid of fluorescent tags such as, for example, GFP, YFP, RFP, or Quantum dots with monoclonal antibodies with associated fluorescent tags. Protein biomarkers such as, for example, EGFRvIII, that were differentially fluorescently tagged, may also be visualized and determine co-localization of different protein biomarkers with the Tenascin-C containing microparticles. Identifying a Tenascin-C containing microparticle population may thus be achieved without removing or isolating tumor-derived microparticles from the general microparticle population in a sample, as would occur during an isolation step such as an immunoaffinity purification of Tenascin-C containing microparticles.

Various methods and features described herein that are applicable to the isolation of tumor-derived microparticles may also be applicable to the identification of tumor-derived microparticles. For example, identical bodily fluids may be used as samples in either methods of isolating or identifying tumor-derived microparticles. The various methods and features described herein that are applicable to either the isolation or the identification methods described herein will be readily apparent to one of skill in the art.

Types of Tumors

The methods of the present disclosure are used to isolate or identify a microparticle derived from any type of tumor arising from any one of the following cancers including, for example, adult acute lymphoblastic leukemia, childhood acute lymphoblastic leukemia, adult acute myeloid leukemia, childhood acute myeloid leukemia, adrenocortical carcinoma, childhood adrenocortical carcinoma, aids-related cancers, aids-related lymphoma, anal cancer, appendix cancer, basal cell carcinoma, extrahepatic bile duct cancer, bladder cancer, childhood bladder cancer, bone cancer, osteosarcoma and malignant fibrous histiocytoma, childhood brain stem glioma, adult brain tumor, childhood central nervous system atypical teratoid/rhabdoid tumor, childhood central nervous system embryonal tumors, childhood astrocytomas, childhood pineal parenchymal tumors of intermediate differentiation, childhood supratentorial primitive neuroectodermal tumors and pineoblastoma, childhood brain and spinal cord tumors, breast cancer, childhood breast cancer, male breast cancer, childhood bronchial tumors, burkitt lymphoma, childhood carcinoid tumor, primary central nervous system lymphoma, cervical cancer, childhood cervical cancer, childhood chordoma, chronic lymphocytic leukemia, chronic myelogenous leukemia, chronic myeloproliferative disorders, colon cancer, childhood colorectal cancer, childhood craniopharyngioma, childhood central nervous system embryonal tumors, endometrial cancer, childhood ependymoblastoma, childhood ependymoma, esophageal cancer, childhood esophageal cancer, Ewing sarcoma family of tumors, childhood extracranial germ cell tumor, extragonadal germ cell tumor, gallbladder cancer, gastric (stomach) cancer, childhood gastric (stomach) cancer, gastrointestinal carcinoid tumor, gastrointestinal stromal tumor (gist), childhood gastrointestinal stromal cell tumor, extragonadal germ cell tumor, ovarian germ cell tumor, gestational trophoblastic tumor, adult glioma, hairy cell leukemia, head and neck cancer, adult (primary) hepatocellular (liver) cancer, childhood (primary) hepatocellular (liver) cancer, adult Hodgkin lymphoma, childhood Hodgkin lymphoma, hypopharyngeal cancer, intraocular melanoma, islet cell tumors (endocrine pancreas), Kaposi sarcoma, kidney (renal cell) cancer, childhood kidney cancer, Langerhans cell histiocytosis, laryngeal cancer, childhood laryngeal cancer, chronic lymphocytic leukemia, chronic myelogenous leukemia, hairy cell leukemia, lip and oral cavity cancer, adult (primary) liver cancer, childhood (primary) liver cancer, non-small cell lung cancer, small cell lung cancer, adult non-Hodgkin lymphoma, childhood non-Hodgkin lymphoma, primary central nervous system lymphoma, Waldenström macroglobulinemia, malignant fibrous histiocytoma of bone and osteosarcoma, childhood medulloblastoma, childhood medulloepithelioma, melanoma, Merkel cell carcinoma, adult malignant mesothelioma, childhood mesothelioma, metastatic squamous neck cancer with occult primary, mouth cancer, childhood multiple endocrine neoplasia syndrome, multiple myeloma/plasma cell neoplasm, mycosis fungoides, myelodysplastic syndromes, myelodysplastic/myeloproliferative neoplasms, chronic myelogenous leukemia, multiple myeloma, chronic myeloproliferative disorders, nasal cavity and paranasal sinus cancer, nasopharyngeal cancer, childhood nasopharyngeal cancer, neuroblastoma, childhood oral cancer, oropharyngeal cancer, childhood ovarian cancer, ovarian epithelial cancer, ovarian germ cell tumor, ovarian low malignant potential tumor, pancreatic cancer, childhood pancreatic cancer, childhood papillomatosis, parathyroid cancer, penile cancer, pharyngeal cancer, pituitary tumor, plasma cell neoplasm/multiple myeloma, pleuropulmonary blastoma, prostate cancer, rectal cancer, respiratory tract carcinoma involving the nut gene on chromosome 15, retinoblastoma, childhood rhabdomyosarcoma, salivary gland cancer, childhood salivary gland cancer, adult soft tissue sarcoma, childhood soft tissue sarcoma, uterine sarcoma, Sézary syndrome, skin cancer (nonmelanoma), childhood skin cancer, skin cancer (melanoma), Merkel cell skin carcinoma, small intestine cancer, adult soft tissue sarcoma, childhood soft tissue sarcoma, squamous cell carcinoma, cutaneous t-cell lymphoma, testicular cancer, throat cancer, thymoma and thymic carcinoma, childhood thymoma and thymic carcinoma, thyroid cancer, childhood thyroid cancer, gestational trophoblastic tumor, transitional cell cancer of ureter and renal pelvis, urethral cancer, endometrial uterine cancer, uterine sarcoma, vaginal cancer, childhood vaginal cancer, vulvar cancer, and Wilms' tumor.

In some preferred embodiments, the cancer is bladder cancer, brain cancer, breast cancer, colon and rectal cancer, endometrial cancer, kidney (renal cell) cancer, leukemia, lung cancer, ovarian cancer, melanoma, lymphoma, pancreatic cancer, prostate cancer, skin cancer (nonmelanoma), thyroid cancer, oral cancer, gastric cancer, gastrointestinal cancer, or nasopharyngeal cancer. In preferred embodiments, the cancer is brain cancer. The brain cancer may be, for example, astrocytoma, glioblastoma, ependymoma, oligodendroglioma, or mixed glioma. In particularly preferred embodiments, the cancer is glioblastoma or anaplastic astrocytoma.

Analysis of Tumor-Derived Microparticles

Tumor-derived microparticles that have been isolated according to the methods of the present disclosure may be analyzed for the content and/or quantity of tumor-derived microparticles to gain additional information about the tumor cell and status of such from which the tumor-derived microparticle originated. Isolation of tumor-derived microparticles according to the methods of the present disclosure thus presents a useful tool to aid in various aspects of cancer treatment and management. Accordingly, the present disclosure includes methods relating to the treatment and management of cancer such as methods of diagnosis, prognosis, determining cancer stage and tumor grade, predicting response to treatment, monitoring progression of disease, predicting recurrence of disease, determining cancer risk factors, developing treatment plans, and choosing test subjects for participation in clinical trials.

Analysis of Biomarkers

The present disclose provides methods of analyzing tumor-derived microparticles to determine the expression status of biomarkers in the tumor-derived microparticles. The biomarkers may be proteins present in the tumor-derived microparticle or on the surface of the tumor-derived microparticle (i.e. microparticle-associated proteins). Accordingly, such methods may include a step of detecting the expression level of a protein from a tumor-derived microparticle, either when associated with the microparticle or subsequent to dissociation from the microparticle.

The expression level of a protein may include a relative or absolute amount of a protein from a tumor-derived microparticle, or it may simply refer to the presence or absence of a protein in a sample. The expression level of the microparticle-associated protein may be detected by any methods known to one of skill in the art (see, for example: Coligan et al, Unit 9, *Current Protocols in Immunology*, Wiley Interscience, 1994), which include, for example: immunohistochemistry (*Microscopy, Immunohistochemistry and Antigen Retrieval Methods for Light and Electron Microscopy*, M. A. Hayat (Author), Kluwer Academic Publishers, 2002; Brown C.: "Antigen retrieval methods for immunohistochemistry," Toxicol Pathol 1998; 26 (6): 830-1), ELISA (Onorato et al., "Immunohistochemical and ELISA assays for biomarkers of oxidative stress in aging and disease," *Ann NY Acad Sci* 1998 20; 854:277-90), Western blotting (Laemmeli UK: "Cleavage of structural proteins during the assembly of the head of a bacteriophage T4," Nature 1970; 227:680-685; Egger & Bienz, "Protein (western) blotting", *Mol Biotechnol* 1994; 1 (3): 289-305), and antibody microarray hybridization (Huang, "Detection of multiple proteins in an antibody-based protein microarray system," *Immunol Methods* 2001 1; 255 (1-2): 1-13).

Various approaches may be used in preparation for detecting the expression levels of the microparticle-associated proteins. In one approach, the proteins are dissociated from microparticles. For example, the microparticles are lysed, and the proteins in the microparticles are extracted, precipitated, and reconstituted for analysis. In another approach, the microparticles are kept intact so that the protein remains associated, and the microparticles are attached to a column, resin, or bead. The reconstituted protein or the microparticles attached to a column, resin, or bead are used in the detection step. For example, the reconstituted protein or the microparticles attached to a column, resin, or bead are contacted with an antibody specific to the protein biomarker.

In preferred embodiments, detecting the expression level includes detecting binding of the protein to an antibody specific to the protein. Antibodies may be monoclonal or polyclonal, and they may be obtained from a commercial source or generated for use in the methods described herein. Methods for producing and evaluating antibodies are well known in the art, see, e.g., Coligan, (1997) *Current Protocols in Immunology*, John Wiley & Sons, Inc; and Harlow and Lane (1989) *Antibodies: A Laboratory Manual*, Cold Spring Harbor Press, NY ("Harlow and Lane").

The antibody may be covalently bound to a bead or fixed on a solid surface, such as glass, plastic, or silicon chip. Typically, microparticle-associated proteins are contacted with an antibody specific to at least one protein biomarker. Any protein biomarker present in the sample will bind to the specific antibody. The mixture is washed, and the antibody-protein biomarker complexes can be detected.

This detection can be achieved by contacting the washed antibody-protein biomarker complexes with a detection reagent. This detection reagent may be, for example, a secondary antibody which is labeled with a detectable label. Exemplary detectable labels include magnetic beads (e.g., DYNABEADS™), fluorescent dyes, radiolabels, enzymes (e.g., horseradish peroxide, alkaline phosphatase, and others commonly used in ELISA), and colorimetric labels such as colloidal gold, colored glass, or plastic beads.

Methods for measuring the amount or presence of antibody-biomarker complexes may include, for example, detection of fluorescence, luminescence, chemiluminescence, absorbance, reflectance, transmittance, birefringence, or refractive index (e.g., surface plasmon resonance, ellipsometry, a resonant mirror method, a grating coupler waveguide method, or interferometry). Optical methods include microscopy (both confocal and non-confocal), imaging methods, dynamic light scattering, fluorescent NanoSight Tracking Analysis (NanoSight Ltd., Wiltshire UK) and non-imaging methods. Electrochemical methods include voltametry and amperometry methods. Radio frequency methods include multipolar resonance spectroscopy. Methods for performing these assays are readily known in the art. Useful assays may include, for example, an enzyme immune assay (EIA) such as enzyme-linked immunosorbent assay (ELISA), a radioimmune assay (RIA), a Western blot assay, or a slot blot assay. These methods are also described in, e.g., *Methods in Cell Biology: Antibodies in Cell Biology*, volume 37 (Asai, ed. 1993); *Basic and Clinical Immunology* (Stites & Terr, eds., 7th ed. 1991); and Harlow & Lane, supra. In preferred embodiments, detecting binding of the protein biomarker to an antibody specific to the biomarker includes detecting fluorescence.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, the volume of solution, concentrations, and the like. Usually the assays will be carried out at ambient temperature, although they can be conducted over a range of temperatures, such as 10° C. to 40° C.

Immunoassays may also be used to determine the presence or absence of a microparticle-associated protein as well as the quantity of the microparticle-associated protein. The amount of an antibody-biomarker complex can be determined by comparing to a standard. A standard may be, for example, a known compound or another protein known to be present in a sample. As noted above, the test amount of marker need not be measured in absolute units, as long as the unit of measurement can be compared to a control.

In some embodiments, the methods involve detecting the expression level of clusters of microparticle-associated proteins. Detecting the expression level of multiple protein biomarkers can be achieved, for example, with a protein microarray such as an antibody microarray. The production of such microarrays can be carried out essentially as described in Schweitzer & Kingsmore, "Measuring proteins on microarrays," *Curr Opin Biotechnol* 2002; 13 (1): 14-9; Avseenko et al., "Immobilization of proteins in immunochemical microarrays fabricated by electrospray deposition," *Anal Chem* 2001 15; 73 (24): 6047-52; Huang, "Detection of multiple proteins in an antibody-based protein microarray system," *Immunol Methods* 2001 1; 255 (1-2): 1-13. In general, protein microarrays may be produced essentially as described in Schena et al., "Parallel human genome analysis: Microarray-based expression monitoring of 1000 genes," *Proc. Natl. Sci. USA* (1996) 93, 10614-10619; U.S. Pat. Nos. 6,291,170 and 5,807,522 (see above); U.S. Pat. No. 6,037,186 (Stimpson, inventor) "Parallel production of high density arrays," WO 99/13313 (Genovations Inc (US), applicant) "Method of making high density arrays," WO 02/05945 (Max Delbruck Center for Molecular Medicine (Germany), applicant) "Method for producing microarray chips with nucleic acids, proteins or other test substrates."

Protein or antibody microarray hybridization may be carried out essentially as described in Ekins et al. *J Pharm Biomed Anal* 1989. 7:155; Ekins and Chu, *Clin Chem* 1991. 37:1955; Ekins and Chu, *Trends in Biotechnology*, 1999, 17, 217-218; MacBeath and Schreiber, *Science* 2000; 289 (5485): p. 1760-1763.

In some embodiments, the expression levels of multiple microparticle-associated proteins are detected simultaneously. Simultaneous detection may be achieved with a multiplex system, such as the xMAP® assay system from Luminex (Austin, TX). In such a system, beads are internally dyed with different ratios of red and infrared fluorophores, which produces beads having unique spectral signatures. Each unique bead is covalently bound to an antibody specific to one protein biomarker from the cluster. A set of beads containing beads specific to unique biomarkers present in the particular cluster being used is then applied to a sample to allow for capture of multiple protein biomarkers within one sample. The set of beads may contain beads specific to as many as 173 unique protein biomarkers. Secondary antibodies labeled with phycoerythrin or a similar fluorophore are applied to detect binding of the biomarker. High-tech fluidics allows each bead to be measured discretely. Excitation of the red and infrared dyes allows each bead to be identified, and detection of orange fluorescence allows for measurement of the levels of each biomarker in the sample. The assays may be carried out in 96-well plate format.

The methods may further include determining whether the proteins are associated with microparticles derived from specific tissue or whether the proteins are associated with microparticles derived from specific organelles.

Exemplary microparticle-associated proteins that may be detected from tumor-derived microparticles may include, for example, Tenascin-C, IDH1, IDH2, PDGFRalpha, or $\alpha_\nu/\beta_{III}$ integrin, EGFRvIII, EGFR, HER-2, HER-3, HER-4, MET, cKit, PDGFR, Wnt, beta-catenin, K-ras, H-ras, N-ras, Raf, N-myc, c-myc, IGFR, PI3K, Akt, BRCA1, BRCA2, PTEN, FGFR3, EphB2, ROR1, EphA2, EphA4, VEGFR-2, VEGFR-1, Tie-2, TEM-1 and CD276, ErbB3, ErbB4, FGFR1, FGFR4, InsulinR, IGF-1R, Dtk, Mer, MSPR, c-Ret, ROR1, ROR2, Tie-1, Tie-2, TrkA, TrkB, VEGFR3, EphA1, EphA7, EphB2, and EphB4.

In some preferred embodiments, the biomarkers that are detected from tumor-derived microparticles include, for example, IDH1, IDH2, EGFRvIII, 14-3-3, H2AX, PPIX, glycoprotein NMB (GPNMB), and glycoporin A.

In some preferred embodiments, tumor-derived microparticles isolated by capturing Tenascin-C positive microparticles are analyzed to determine the expression status of EGFR, EGFRvIII, and other EGFR-variants.

Analysis of the expression levels of microparticle-associated proteins may allow for diagnosis of cancer, determination of prognosis of a test subject with cancer, etc. Certain protein biomarker clusters will be better for some methods than for others. Accordingly, the expression profiles of multiple biomarker clusters may be detected in order to make an accurate diagnosis, determination of prognosis, etc.

Such methods may include comparing the expression level of one or more microparticle-associated proteins from tumor-derived microparticles from the test subject (i.e. the subject from which the tumor-derived microparticles were isolated) with the expression level of the one or more proteins in samples from a plurality of control subjects. Controls for each specific method are discussed in the sections below. The expression levels from samples from the plurality of control subjects may be simultaneously obtained with the test subject expression levels or may constitute a set of numerical values stored on a computer or on computer readable medium. In preferred embodiments, the control subjects are of the same sex and of a similar age as the test subject. Control subjects may also be of a similar racial background as the test subject. Preferably, samples taken from the test subject and from the plurality of control subjects are of the same type, e.g., blood samples.

Comparison of the expression levels of the one or more microparticle-associated proteins in samples from the test subject and from a plurality of control subjects may be performed manually or automatically by a computer program. The expression level of the one or more microparticle-associated proteins in the sample from the test subject may be compared individually to the expression level of the one or more microparticle-associated proteins from samples in each control subject, or the expression level of the one or more microparticle-associated proteins in the sample from the test subject may be compared to an average of the expression levels from samples from the plurality of control subjects. In certain embodiments, the values for the expression levels of the one or more proteins in samples from both the test subject and the plurality of control subjects may be transformed. For example, the expression levels may be transformed by taking the logarithm of the value. Moreover, the expression levels may be normalized by, for example, dividing by the median expression level among all of the samples.

In certain embodiments, the expression level of the one or more microparticle-associated proteins in the sample from the test subject is increased relative to the expression level of the one or more microparticle-associated proteins in samples from a plurality of control subjects. In other embodiments, the expression level of the one or more microparticle-associated proteins in the sample from the test subject is decreased relative to the expression level of the one or more microparticle-associated proteins in samples from a plurality of control subjects. Typically, an expression level is said to be increased or decreased relative to a second expression level if the difference between the two expression levels is statistically significant. The difference between two levels is considered to be statistically significant if it was unlikely to have occurred by chance. Statistical significance may be measured by any means known in the art, such as, for example, Fisherian statistical hypothesis testing or the Neyman-Pearson lemma. In certain embodiments, the one or more proteins may not be expressed in samples from the plurality of controls but will be expressed in the sample from the test subject. In other embodiments, the one or more proteins may not be expressed in the sample from the test subject but will be expressed in samples from the plurality of controls.

The methods may include a step of deriving a score from the comparison of the expression level of the one or more microparticle-associated proteins in the sample from the test subject with the expression level of the one or more microparticle-associated proteins in samples from the plurality of control subjects, where the score indicates a level of similarity between the expression level of the one or more proteins in the sample from the test subject and the expression level of the one or more proteins in the samples from the plurality of control subjects. The score may be derived by any methods known to one of skill in the art. In certain embodiments, the score may simply be a measure of the difference in expression levels. In preferred embodiments, the score is a correlation coefficient. A correlation coefficient describes the similarity between two expression patterns. Expression levels may be considered similar if the correlation coefficient is greater than or equal to 0.5. In preferred embodiments, for expression levels to be considered significantly similar, the correlation coefficient should be greater than 0.6, 0.7, 0.8, 0.9, or 0.95. In other embodiments, the score is generated by other statistical methods which produce a measure of mutual information to describe the similarity between two expression patterns. Expression levels may be considered similar if the normalized mutual information value is greater than or equal to 0.7. In preferred embodiments, for the expression levels to be considered significantly similar, the normalized mutual information value should be greater than 0.8, 0.9, or 0.95. Patterns of expression levels among multiple biomarkers may also be considered similar if they cluster closely upon hierarchical clustering of expression data (Eisen et al. 1998). Similar patterns may be those biomarkers that are among the 1, 2, 5, 10, 20, 50, or 100 nearest neighbors in a hierarchical clustering or have a similarity score (Eisen et al. 1998) of greater than 0.5, 0.7, 0.8, 0.9, 0.95, or 0.99.

If the score indicates a significant level of similarity between the expression level of the one or more microparticle-associated proteins in the sample from the test subject and the expression level of the one or more microparticle-associated proteins in samples from the plurality of control subjects, then the test subject can be said to have or to be likely to have the same classification as that of the plurality of control subjects. For example, if the score indicates a significant level of similarity between the expression level of the one or more proteins in the sample from the test subject and the expression level of the one or more proteins in samples from the plurality of control subjects who are known to have brain cancer, then the test subject can be said to have or said likely to have a diagnosis of brain cancer.

Particular expression profiles of microparticle-associated proteins from tumor-derived microparticles may be used to infer information about the tumor cell from which the tumor-derived microparticle originated. In some preferred embodiments, the expression status of EGFRvIII, 14-3-3, H2AX, PPIX, and glycoporin A is determined. In some preferred embodiments, an expression profile where the presence of EGFRvIII, the presence of 14-3-3, the presence of H2AX, the presence of PPIX, and the absence of glycoporin A is observed is indicative that the tumor-derived microparticle analyzed for these biomarkers originated from a brain tumor.

In some preferred embodiments, the expression status of IDH-1, IDH-2, EGFRvIII, 14-3-3, H2AX, PPIX, glycoporin A, and NMB (GPNMB) are determined to provide information relating to whether or not the tumor-derived microparticles originated from a brain tumor.

Analysis of Characteristics

In addition to biomarker analysis, the present disclosure provides methods of analyzing tumor-derived microparticles to determine the status of one or more characteristics of the microparticles. Character analysis of the tumor-derived microparticles may provide information about the tumor from which the tumor-derived microparticles originated that could not be determined from biomarker analysis, such as the size of the tumor.

In some embodiments, isolated tumor-derived microparticles, such as those obtained by capturing Tenascin-C positive microparticles, may be analyzed for total number/quantity of tumor-derived microparticles number relative to a control, such as the total number of microparticles isolated from a sample.

Tumor-derived microparticle number in a sample may be determined using dynamic light scattering or Nanoparticle Tracking Analysis (NTA). In this method, microparticles may be analyzed using, for example, a Malvern 4700 autosizer (Malvern instruments Ltd., UK) with a 20 mW helium/neon laser (633 nm) or a Nanoparticle Tracking Analysis (NTA) method (NanoSight, LM 10 system, software: NanoSight NTA version 2.2, Nanosight Ltd., Wiltshire, UK). Light scattering from microparticle samples may be detected by a photomultiplier tube placed at 90 degrees to the incident laser beam. The translational diffusion coefficient of the microparticle material may be calculated from the time autocorrelation of the scattered light intensity and the translational diffusion coefficient may be extracted from the correlogram using the method of cumulants, as applied in the proprietary Malvern software. The diameter of the microparticles may be obtained from the application of Stokes-Einstein equations. Dynamic light scattering is a technique known in the art and may be used to evaluate various physical characteristics of the microparticles as disclosed herein.

Additional methods of evaluating characteristics of tumor-derived microparticles may include ELISA assays, flow cytometry, mass spectrometry analysis, nuclear magnetic resonance, and other methods known in the art.

Evaluation of physical characteristics of tumor-derived microparticles may provide information relating to the tumor or tumor cell from which the tumor-derived microparticles originated. For example, the concentration (number) of tumor-derived microparticles in a sample from a given subject may be evaluated over time. This type of temporal analysis may inform tumor status; for example, an increase in the concentration of tumor-derived microparticles in a sample over time may indicate an increase in tumor size and/or growth rate. Similarly, this analysis may be extrapolated to inform cancer treatment efficacy, tumor progression, etc. In some preferred embodiments, tumor-derived microparticles are analyzed to determine the status such as the quantity, for example, of tumor-derived microparticles.

Clinical Applications

The methods of the present disclosure may be used in clinical applications to inform various aspects related to tumors and/or tumor cells from which tumor-derived microparticles in a subject originated. Such clinical applications generally involve comparison of tumor-derived microparticles from a test subject with general microparticles and/or tumor-derived microparticles of one or more control subjects. As the microparticles from a sample from a control subject may or may not be derived from tumors, comparison to a test subject may involve general microparticles, tumor-derived microparticles, or both depending on the clinical application and goal of the application. One of skill in the art would readily recognize appropriate control microparticles from control subjects for various clinical applications.

Diagnosing Cancer

The present disclosure includes methods of diagnosing cancer in a test subject. Diagnosing cancer, as described herein, includes, for example, making a determination that a test subject has cancer and making a determination of the specific type of cancer in a test subject based, at least in part, on the results of the analysis of tumor-derived microparticles isolated according to the methods of the present disclosure. Diagnosing cancer may also include the consideration of other signs, symptoms, and test results of the test subject. Symptoms will vary with the type of cancer and may include, for example, weight loss, fatigue, muscle weakness, swollen lymph nodes, chronic cough, blood in stool, recurrent headaches, pain, internal bleeding, partial lung collapse, hoarse voice, shortness of breath, vision problems, loss of appetite, night sweats, fever, confusion, nausea, vomiting, or seizures. Test results may come from imaging studies, such as x-ray, ultrasonography, magnetic resonance imaging, positron emission technology (PET), or computer tomography (CT). Moreover, diagnosing may include the consideration of factors such as age, sex, family history, previous medical history, or lifestyle, which could indicate an increased likelihood of a diagnosis of cancer.

In certain embodiments, diagnosing cancer in the test subject includes comparing the expression level of one or more microparticle-associated proteins from tumor-derived microparticles in samples from the test subject with the expression level of one or more microparticle-associated proteins in samples from a plurality of control subjects. The plurality of control subjects may include subjects known to have a certain type of cancer or subjects known not to have a certain type of cancer. In preferred embodiments, the plurality of control subjects includes both subjects known to have a certain type of cancer and subjects known not to have that type of cancer. Cancer diagnosis may also be based on the results of analysis of one or more characteristics of tumor-derived microparticles in a subject.

In certain embodiments, the methods of diagnosing cancer in a test subject include a step of deriving a score from the comparison of the expression level of one or more microparticle-associated proteins from tumor-derived microparticles in the sample from the test subject with the expression level of one or more microparticle-associated proteins in the samples from the plurality of control subjects, where the score indicates a level of similarity between the expression level of the one or more proteins in the sample from the test subject and the expression level of the one or more proteins in the samples from the plurality of control subjects. The score may be, for example, a correlation coefficient.

In certain embodiments, a specific type of cancer may be diagnosed in the test subject if the score indicates a significant level of similarity between the expression level of the one or more microparticle-associated proteins from tumor-derived microparticles in the sample from the test subject and the expression level of the one or more microparticle-associated proteins in the samples from the plurality of control subjects known to have the type of cancer. In other embodiments, the test subject may be diagnosed as not having a certain type of cancer if the score indicates a high level of similarity between the expression level of the one or more proteins in the sample from the test subject and the expression level of the one or more microparticle-associated proteins in the samples from the plurality of control subjects known not to have the type of cancer.

In some preferred embodiments, tumor-derived microparticles from a subject are analyzed with respect to a diagnosis of brain cancer. For example, an expression analysis of microparticle-associated proteins isolated from the tumor-derived microparticles of the subject, where the presence of EGFRvIII, the presence of 14-3-3, the presence of H2AX, the presence of PPIX, and the absence of glycoporin A is observed, may be used to determine that the subject should be diagnosed with brain cancer.

In certain embodiments, diagnosing cancer in a test subject may also involve comparing the characteristics of any tumor-derived microparticles from a test subject with the microparticles from a control subject. For example, a comparison of the number/concentration of any tumor-derived microparticles from a test subject relative to the tumor-derived microparticles of a control subject may be used to inform whether a cancer diagnosis should be made in the test subject.

Determining Prognoses

In certain aspects, the present disclosure includes methods of determining the prognosis of a test subject with cancer. A prognosis refers to the likely outcome of cancer in a test subject. The prognosis may include, for example, the survival rate, 5-year survival rate, disease-free or recurrence-free survival rate, a projection of the course of the illness over time, and the likelihood of metastasis of a primary cancer. In addition to the determination of a prognosis based on the expression level of one or more microparticle-associated proteins from a tumor-derived microparticle, the prognosis may also be based on additional factors, such as, for example, the type, location, and stage of the cancer, the tumor grade, the presence of chromosomal abnormality or abnormal blood cell counts, and the age, general health, and predicted response to treatment of the test subject. Further, prognosis may also be based on the results of analysis of one or more characteristics of tumor-derived microparticles in a subject, such as changes in tumor-derived microparticle number, concentration, or size over time.

In certain embodiments, determining the prognosis of the test subject includes comparing the expression level of one or more microparticle-associated proteins from tumor-derived microparticles in the sample from the test subject with the expression level of one or more microparticle-associated proteins in samples from a plurality of control subjects. The plurality of control subjects may include subjects who have cancer and who are known to have a good prognosis or subjects who have cancer and are known to have a bad prognosis. In preferred embodiments, the plurality of control subjects includes both subjects known to have a good prognosis and subjects known to have a bad prognosis. Preferably, the control subjects have the same type of cancer as the test subject. A good prognosis may include, for example, a low likelihood of metastasis, a low likelihood of disease recurrence, a low grade of tumor, an early stage of cancer, a high likelihood of a positive response to treatment, and a high likelihood of survival or disease-free survival within a time period of 5 years. A bad prognosis may include, for example, a high likelihood of metastasis, a high likelihood of disease recurrence, a high grade of tumor, a late stage of cancer, a low likelihood of a positive response to treatment and a low likelihood of survival or disease-free survival within a time period of 5 years.

In certain embodiments, the methods of determining a prognosis for the test subject include a step of deriving a score from the comparison of the expression level of the one or more microparticle-associated proteins from tumor-derived microparticles in the sample from the test subject with the expression level of the one or more microparticle-associated proteins in the samples from the plurality of control subjects, where the score indicates a level of similarity between the expression level of the one or more microparticle-associated proteins from tumor-derived microparticles in the sample from the test subject and the expression level of the one or more proteins in the samples from the plurality of control subjects. The score may be, for example, a correlation coefficient.

In certain embodiments, a good prognosis may be determined for the test subject if the score indicates a significant level of similarity between the expression level of the one or more microparticle-associated proteins from tumor-derived microparticles in the sample from the test subject and the expression level of the one or more microparticle-associated proteins in the samples from the plurality of control subjects known to have a good prognosis. In other embodiments, a bad prognosis may be determined for the test subject if the score indicates a high level of similarity between the expression level of the one or more microparticle-associated proteins from tumor-derived microparticles in the ample from the test subject and the expression level of the one or more microparticle-associated proteins in the samples from the plurality of control subjects known to have a bad prognosis.

In certain embodiments, determining the prognosis of test subject with cancer may also involve comparing the characteristics of tumor-derived microparticles from a test subject with the microparticles from a control subject. For example, a comparison of the number/concentration of tumor-derived microparticles from a test subject relative to the tumor-derived microparticles of a control subject may be used to determine the prognosis of the test subject with cancer.

Determining the Stage of Cancer

In certain aspects, the present disclosure includes methods of determining the stage of cancer in a test subject. Cancer stage describes the extent or severity of the test subject's cancer according to the extent of growth of the primary tumor and the extent of spread in the body. Typically, the stage of cancer is based on the following main factors: location of the primary (original) tumor, tumor size and number of tumors, lymph node involvement (whether or not the cancer has spread to the nearby lymph nodes), and the presence or absence of metastasis. Cancers of the brain and spinal cord are classified according to cell type and grade. Different staging systems are used for many cancers of the blood or bone marrow, such as lymphoma.

Different types of cancer stage may be determined by the methods of the present disclosure. These include, for example, clinical staging, pathologic staging, and restaging. Typically, the TNM staging system is used to describe the stage of cancer as determined by the methods of the invention. The TNM Staging System is based on the extent of the tumor (T), the extent of spread to the lymph nodes (N), and the presence of metastasis (M). The T category describes the original (primary) tumor and includes the categories TX (primary tumor cannot be evaluated), T0 (no evidence of primary tumor), Tis (carcinoma in situ (early cancer that has not spread to neighboring tissue)), and T1-T4 (size and/or extent of the primary tumor). The N category describes whether or not the cancer has reached nearby lymph nodes and includes the categories NX (regional lymph nodes cannot be evaluated), N0 (no regional lymph node involvement (no cancer found in the lymph nodes)), N1-N3 (involvement of regional lymph nodes (number and/or extent of spread)). The M category tells whether there are distant metastases and includes the categories M0 (no distant metastasis) and MI (distant metastasis).

Each cancer type has its own classification system, so letters and numbers do not always mean the same thing for every kind of cancer. Once the T, N, and M are determined, they are combined, and an overall "Stage" of I, II, III, IV is assigned. Sometimes these stages are subdivided as well, using letters such as IIIA and IIIB.

In certain embodiments, determining the stage of cancer in the test subject includes comparing the expression level of one or more microparticle-associated proteins from tumor-derived microparticles in the sample from the test subject with the expression level of one or more microparticle-associated proteins in samples from a plurality of control subjects. The plurality of control subjects may include subjects known to have a certain stage of cancer. Preferably, the plurality of control subjects will include at least one control subject known to have each of the stages of cancer including Stage 0, Stage I, Stage II, Stage III, and Stage IV.

In certain embodiments, the methods of determining the stage of cancer in a test subject include a step of deriving a score from the comparison of the expression level of one or more microparticle-associated proteins from tumor-derived microparticles in the sample from the test subject with the expression level of one or more microparticle-associated proteins in samples from a plurality of control subjects, where the score indicates a level of similarity between the expression level of one or more microparticle-associated proteins from tumor-derived microparticles in the sample from the test subject and the expression level of one or more microparticle-associated proteins in samples from a plurality of control subjects. The score may be, for example, a correlation coefficient.

In certain embodiments, the stage of cancer in the test subject is determined to be the same as the stage of cancer in one or more control subjects known to have the same stage of cancer if the score indicates a significant level of similarity between the expression level of the one or more microparticle-associated proteins from tumor-derived microparticles in the sample from the test subject and the expression level of one or more microparticle-associated proteins in samples from a plurality of control subjects known to have the same stage of cancer.

In certain embodiments, determining the stage of cancer may also involve comparing the characteristics of tumor-derived microparticles from a test subject with the microparticles from a control subject. For example, a comparison of the number/concentration of tumor-derived microparticles from a test subject relative to the tumor-derived microparticles of a control subject may inform the stage of cancer in the test subject.

Determining Tumor Grade

In certain aspects, the present disclosure includes methods of determining the grade of tumor in a test subject with cancer. Tumor grade is a system used to classify cancer cells in terms of how abnormal they look under a microscope and how quickly the tumor is likely to grow and spread. The methods of the invention allow for a determination of tumor grade based on expression levels of protein biomarkers. Pathologists typically describe tumor grade by four degrees of severity, Grades 1, 2, 3, and 4. The cells of Grade 1 tumors resemble normal cells and tend to grow and multiply slowly. Grade 1 tumors are generally considered to be the least aggressive in behavior. The cells of Grade 3 or Grade 4 tumors do not look like normal cells of the same type. Grade 3 and 4 tumors tend to grow rapidly and spread faster than tumors with a lower grade.

The American Joint Commission on Cancer recommends the following guidelines for grading tumors: GX-grade cannot be assessed (undetermined grade), G1-well-differentiated (low grade), G2-moderately differentiated (intermediate grade), G3-poorly differentiated (high grade), and G4-undifferentiated (high grade). Grading systems are different for each type of cancer. For example, pathologists use the Gleason system to describe the degree of differentiation of prostate cancer cells. The Gleason system uses scores ranging from Grade 2 to Grade 10. Lower Gleason scores describe well-differentiated, less aggressive tumors. Higher scores describe poorly differentiated, more aggressive tumors. Other grading systems include the Bloom-Richardson system for breast cancer and the Fuhrman system for kidney cancer.

In certain embodiments, determining the grade of tumor in the test subject includes comparing the expression level of one or more microparticle-associated proteins from tumor-derived microparticles in the sample from the test subject with the expression level of one or more microparticle-associated proteins in samples from a plurality of control subjects. The plurality of control subjects may include subjects known to have a tumor of a known grade. Preferably, the plurality of control subjects will include at least one control subject known to have a tumor of each of the grades including GX, G1, G2, G3, and G4.

In certain embodiments, the methods of determining the grade of tumor in a test subject include a step of deriving a score from the comparison of the expression level of one or more microparticle-associated proteins from tumor-derived microparticles in the sample from the test subject with the expression level of one or more microparticle-associated proteins in samples from a plurality of control subjects, where the score indicates a level of similarity between the expression level of one or more microparticle-associated proteins from tumor-derived microparticles in the sample from the test subject and the expression level of one or more microparticle-associated proteins in samples from a plurality of control subjects. The score may be, for example, a correlation coefficient.

In certain embodiments, the grade of tumor in the test subject is determined to be the same as the grade of tumor in one or more control subjects known to have the same grade of tumor if the score indicates a significant level of similarity between the expression level of one or more microparticle-associated proteins from tumor-derived microparticles in the sample from the test subject and the expression level of one or more microparticle-associated proteins in samples from a plurality of control subjects known to have the same grade of tumor.

In certain embodiments, determining tumor grade may also involve comparing the characteristics of tumor-derived microparticles from a test subject with the microparticles from a control subject. For example, a comparison of the number/concentration of tumor-derived microparticles from a test subject relative to the tumor-derived microparticles of a control subject may inform the tumor grade in the test subject.

Predicting Response to Treatment

In certain aspects, the present disclosure includes methods of predicting the response of a test subject with cancer to a treatment. Treatments may include, for example, chemotherapy, hormone therapy, combination therapy, immunotherapy, radiation therapy, and surgery. Examples of specific drug treatments include, for example, cyclophosphamide, chlorambucil, melphalan, methotrexate, cytarabine, fludarabine, 6-mercaptopurine, 5-fluorouracil, vincristine, paclitaxel, vinorelbine, docetaxel, doxorubicin, irinotecan, cisplatin, carboplatin, oxaliplatin, tamoxifen, bicalutamide, anastrozole, exemestane, letrozole, imatinib, gefitinib, erlotinib, rituximab, trastuzumab, gemtuzumab ozogamicin, interferon-alpha, tretinoin, arsenic trioxide, bevacizumab, sorafinib, and sunitinib.

A subject is considered to have a complete response to a treatment if a cancer disappears for any length of time after the treatment. A subject is considered to have a partial response to a treatment if the size of a tumor (usually determined by x-rays) is reduced by more than half, although it remains visible on an x-ray. A subject is considered to not respond to a treatment if the tumor continues to increase in size or new sites of disease appear after the treatment.

In certain embodiments, predicting the response of the test subject to a treatment includes comparing the expression level of one or more microparticle-associated proteins from tumor-derived microparticles in the sample from the test subject with the expression level of one or more microparticle-associated proteins in samples from a plurality of control subjects. The plurality of control subjects may include subjects who had cancer and responded to the treatment or subjects who had cancer and did not respond to the treatment. In preferred embodiments, the plurality of control subjects includes both subjects who did and did not respond to the treatment. Preferably, the control subjects have or had the same type of cancer as the test subject. In certain embodiments, the samples from the control subjects were taken from the control subjects before administration of the treatment.

In certain embodiments, the methods of predicting the response of a test subject to a treatment include a step of deriving a score from the comparison of the expression level of one or more microparticle-associated proteins from tumor-derived microparticles in the sample from the test subject with the expression level of one or more microparticle-associated proteins in samples from a plurality of control subjects, where the score indicates a level of similarity between the expression level of the one or more microparticle-associated proteins from tumor-derived microparticles in the sample from the test subject and the expression level of the one or more miroparticle-associated proteins in the samples from the plurality of control subjects. The score may be, for example, a correlation coefficient.

In certain embodiments, the test subject is predicted to respond to the treatment if the score indicates a significant level of similarity between the expression level of the one or more microparticle-associated proteins from tumor-derived microparticles in the sample from the test subject and the expression level of the one or more microparticle-associated proteins in the samples from the plurality of control subjects who responded to the treatment. In other embodiments, the test subject is predicted to not respond to the treatment if the score indicates a high level of similarity between the expression level of the one or more microparticle-associated proteins from tumor-derived microparticles in the sample from the test subject and the expression level of the one or more microparticle-associated proteins in the samples from the plurality of control subjects who did not respond to the treatment.

In certain embodiments, predicting response to treatment may also involve comparing the characteristics of tumor-derived microparticles from a test subject with the microparticles from a control subject.

Monitoring Progression of Cancer

In certain aspects, the invention includes methods of monitoring the progression of cancer in a test subject. "Monitoring progression" as used herein may refer to the use of expression levels of protein biomarkers to provide useful information about a test subject or a test subject's health or disease status. The methods of monitoring the progression of cancer as described herein may be used once or multiple times, at irregular or regular intervals, in the treatment and management of cancer in a test subject.

Monitoring progression may include, for example, determination of prognosis, risk-stratification, selection of drug therapy or other treatment, assessment of ongoing drug therapy, determination of effectiveness of treatment, prediction of outcomes, determination of response to therapy, diagnosis of a disease or disease complication, following of progression of a disease or providing any information relating to a test subject's health status over time, selecting test subjects most likely to benefit from experimental therapies with known molecular mechanisms of action, selecting test subjects most likely to benefit from approved drugs with known molecular mechanisms where that mechanism may be important in a small subset of a disease for which the medication may not have a label, screening a population of test subjects to help decide on a more invasive/expensive test, for example, a cascade of tests from a non-invasive blood test to a more invasive option such as biopsy, or testing to assess side effects of drugs used to treat another indication. In certain embodiments, monitoring the progression of cancer can refer to distinguishing between necrotic tissue and cancerous growth after the administration of radiation therapy to a test subject. In particular, monitoring progression may refer to making a determination that cancer in a test subject has progressed from a less advanced to a more advanced stage of cancer between two time points or making a determination that cancer in a test subject has not progressed from a less advanced to a more advanced stage of cancer between two time points.

Monitoring the progression of cancer may include the use of one or more standard clinical techniques such as ultrasound, magnetic resonance imaging, computed tomography scan, single-photon emission computerized tomography, biopsy, or positron emission tomography scan. Results from these tests may be used to supplement or confirm the information gleaned from the expression levels of the microparticle-associated protein biomarkers from tumor-derived microparticles in the test subject for monitoring the progression of cancer.

In certain embodiments, determining the stage monitoring the progression of cancer in the test subject includes comparing the expression level of one or more microparticle-associated proteins from tumor-derived microparticles in the sample from the test subject with the expression level of one or more microparticle-associated proteins in samples from a plurality of control subjects. The plurality of control subjects may include subjects known to have cancer at different levels of progression. In certain embodiments, the different levels of progression are different stages of cancer, including Stage 0, Stage I, Stage II, Stage III, and Stage IV. In other embodiments, the different levels of progression may be different grades of tumor or different levels of other pathological classifications known in the art.

In certain embodiments, the methods of monitoring the progression of cancer in a test subject include a step of deriving a score from the comparison of the expression level of one or more microparticle-associated proteins from tumor-derived microparticles in the sample from the test subject with the expression level of one or more microparticle-associated proteins in samples from a plurality of control subjects, where the score indicates a level of similarity between the expression level of one or more microparticle-associated proteins from tumor-derived microparticles in the sample from the test subject and the expression level of one or more microparticle-associated proteins in samples from a plurality of control subjects. The score may be, for example, a correlation coefficient.

The cancer in the test subject is determined to have progressed if the score from the most recent time point indicates a significant level of similarity to a first control subject and a score from an earlier time point indicates a significant level of similarity to a second control subject, where the first control subject has a more advanced level of progression of cancer than the level of progression of cancer of the second control subject. Alternatively, cancer in the test subject is determined to have not progressed if the score from the most recent time point indicates a significant level of similarity to a first control subject and a score from an earlier time point indicates a significant level of similarity to a second control subject, where the first control subject has the same or a less advanced level of progression of cancer than the level of progression of cancer of the second control subject.

In certain embodiments, monitoring cancer progression may also involve comparing the characteristics of tumor-derived microparticles from a test subject with the microparticles from a control subject. For example, a comparison of the number/concentration of tumor-derived microparticles from a test subject relative to the tumor-derived microparticles of a control subject may inform the progression of cancer in the test subject. An increase in the number of tumor-derived microparticles from a test subject over time may indicate that the cancer is progressing. A decrease in the number of tumor-derived microparticles from a test subject over time may indicate that the cancer is receding.

Predicting Recurrence of Cancer

In certain aspects, the present disclosure includes methods of predicting the recurrence of cancer in a test subject. "Recurrence of cancer," as used herein, may refer to a return of cancer in a test subject after treatment and after a period of time during which the cancer cannot be detected. In embodiments involving brain cancer, recurrence of brain cancer may include a detection of a tumor mass of at least 25% the size of the original tumor by MRI, a return of brain cancer symptoms, or the appearance of a new tumor of comparable pathology to the original tumor in a different part of the brain. Brain cancer symptoms may include, for example, new onset or change in pattern of headaches, headaches that gradually become more frequent and more severe, unexplained nausea or vomiting, vision problems, such as blurred vision, double vision or loss of peripheral vision, gradual loss of sensation or movement in an arm or a leg, difficulty with balance, speech difficulties, confusion in everyday matters, personality or behavior changes, seizures, especially in someone who doesn't have a history of seizures, hearing problems, or hormonal (endocrine) disorders.

Samples may be taken from the test subject before treatment or at any time after treatment. Typically, the period of time during which the cancer cannot be detected is at least a year and may be a period of several years. The cancer may return to the same place in the body as the original cancer, or it may return to a different place in the body (e.g., metastasis). Cancer may return to the same place in the body as the original cancer even if that part of the body was altered during treatment (e.g., prostate cancer may return in the area of the prostate gland even if the gland has been removed). "Local recurrence" means that the cancer has come back at the same place where it first started. "Regional recurrence" means that the cancer has come back in the lymph nodes near the place where it started. "Distant recurrence" means the cancer has come back in another part of the body, some distance from where it started (often the lungs, liver, bone marrow, or brain). The risk of recurrence of cancer in a test subject will depend on the type of cancer, the type of treatment, and the period of time elapsed since the treatment. Predicting the recurrence of cancer typically involves making a determination of the risk of recurrence in the test subject.

In certain embodiments, predicting the recurrence of cancer in the test subject includes comparing the expression level of one or more microparticle-associated proteins from tumor-derived microparticles in the sample from the test subject with the expression level of one or more microparticle-associated proteins in samples from a plurality of control subjects. The plurality of control subjects may include subjects known to have cancer or subjects known not to have cancer. In preferred embodiments, the plurality of control subjects includes both subjects known to have cancer and subjects known not to have cancer.

In certain embodiments, the methods of predicting the recurrence of cancer in a test subject include a step of deriving a score from the comparison of the expression level of one or more microparticle-associated proteins from tumor-derived microparticles in the sample from the test subject with the expression level of one or more microparticle-associated proteins in samples from a plurality of control subjects, where the score indicates a level of similarity between the expression level of one or more microparticle-associated proteins from tumor-derived microparticles in the sample from the test subject and the expression level of one or more microparticle-associated proteins in samples from a plurality of control subjects. The score may be, for example, a correlation coefficient.

In certain embodiment, a high likelihood of recurrence of cancer in the test subject is predicted if the score indicates a significant level of similarity between the expression level of one or more microparticle-associated proteins from tumor-derived microparticles in the sample from the test subject and the expression level of one or more microparticle-associated proteins in samples from a plurality of control subjects. In other embodiments, a low likelihood of recurrence of cancer in the test subject is predicted if the score indicates a high level of similarity between the expression level of one or more microparticle-associated proteins from tumor-derived microparticles in the sample from the test subject and the expression level of one or more microparticle-associated proteins in samples from a plurality of control subjects known not to have cancer.

In certain embodiments, assessing the recurrence of cancer may also involve comparing the characteristics of tumor-derived microparticles from a test subject with the microparticles from a control subject. For example, a comparison of the number/concentration of tumor-derived microparticles from a test subject relative to the tumor-derived microparticles of a control subject may inform the likelihood of cancer recurrence in the test subject.

Developing Treatment Plans

In certain aspects, the present disclosure includes methods of developing a treatment plan for a test subject with cancer. Developing a treatment plan may include choosing one or more treatments for a test subject, determining the length of time for each treatment, and determining the order of administration of the treatments. More than one treatment may be given at a time. Typically, the treatment plan begins with a primary therapy. The primary therapy may be chemotherapy, radiation, surgery, or a combination of any of these. Developing a treatment plan may include choosing a treatment to be administered after the primary treatment. This secondary treatment is typically referred to as an adjuvant therapy. Adjuvant therapies may include, for example, chemotherapy, hormone therapy, radiation therapy, immunotherapy, or targeted therapy. Typical drug treatments chosen in developing a treatment plan include those listed in the section above entitled, "Predicting Response to Treatment." Developing a treatment plan for a test subject with cancer may include a consideration of the age, health status, family history, diagnosis, and prognosis of the test subject.

Developing a treatment plan for a test subject with cancer may include choosing alternative treatments for cancer such as diet modification, exercise, acupuncture, aromatherapy, biofeedback, hypnosis, massage therapy, meditation, music therapy, relaxation techniques, tai chi, yoga, or medicinal herbs.

In certain embodiments, developing a treatment plan for a test subject with cancer includes comparing the expression level of one or more microparticle-associated proteins from tumor-derived microparticles in the sample from the test subject with the expression level of one or more microparticle-associated proteins in samples from a plurality of control subjects. The plurality of control subjects may include subjects who had cancer and responded to a treatment or subjects who had cancer and did not respond to a treatment. In preferred embodiments, the plurality of control subjects includes both subjects who did and did not respond to a treatment. Preferably, the control subjects have or had the same type of cancer as the test subject. In certain embodiments, the samples from the control subjects were taken from the control subjects before administration of the treatment.

In certain embodiments, the methods of developing a treatment plan for a test subject with cancer include a step of deriving a score from the comparison of the expression level of one or more microparticle-associated proteins from tumor-derived microparticles in the sample from the test subject with the expression level of one or more microparticle-associated proteins in samples from a plurality of control subjects, where the score indicates a level of similarity between the expression level of one or more microparticle-associated proteins from tumor-derived microparticles in the sample from the test subject and the expression level of one or more microparticle-associated proteins in samples from a plurality of control subjects. The score may be, for example, a correlation coefficient.

In certain embodiments, a treatment may be included in the treatment plan if the score indicates a significant level of similarity between the expression level of one or more microparticle-associated proteins from tumor-derived microparticles in the sample from the test subject and the expression level of one or more microparticle-associated proteins in samples from a plurality of control subjects who responded to the treatment. In other embodiments, a treatment may not be included in the treatment plan if the score indicates a high level of similarity between the expression level of one or more microparticle-associated proteins from tumor-derived microparticles in the sample from the test subject and the expression level of one or more microparticle-associated proteins in samples from a plurality of control subjects who did not respond to the treatment.

In certain embodiments, developing a treatment plan for a test subject with cancer may also involve comparing the characteristics of tumor-derived microparticles from a test subject with the microparticles from a control subject. For example, a comparison of the number/concentration of tumor-derived microparticles from a test subject relative to the tumor-derived microparticles of a control subject may be used to develop a treatment plan for the test subject with cancer.

Choosing Subjects to Participate in Clinical Trials

In certain aspects, the present disclosure includes methods of choosing a test subject to participate in a clinical trial. Clinical trials are used to find better ways to prevent, diagnose, and treat cancer. In addition to detection of the expression level of the one or more proteins in a sample from the test subject, choosing a test subject to participate in a clinical trial may be based on the test subject's age, health status, stage of cancer, diagnosis, prognosis, or likelihood of responding to a treatment administered in the clinical trial. Preferably, test subjects are chosen to participate in a clinical trial if participation of those subjects in the trial will enhance the information gained from the clinical trial. Typically, participation of subjects in a clinical trial will enhance the information gained from the trial if those subjects are expected to respond to a treatment or regimen being administered in the trial. The methods described herein may be applied to treatment trials, prevention trials, screening trials, or quality of life trials. Moreover, the methods may be applied to any phase of clinical trial, such as a phase I, phase II, phase III, or phase IV trial. The treatments administered in treatment trials may include, for example, chemotherapy, immunotherapy, hormone therapy, targeted therapies, or alternative therapies.

In certain embodiments, choosing a test subject to participate in a clinical trial includes comparing the expression level of one or more microparticle-associated proteins from tumor-derived microparticles in the sample from the test subject with the expression level of one or more microparticle-associated proteins in samples from a plurality of control subjects. The plurality of control subjects may include subjects who had cancer and responded to a treatment or subjects who had cancer and did not respond to a treatment. In preferred embodiments, the plurality of control subjects includes both subjects who did and did not respond to a treatment. Preferably, the control subjects have or had the same type of cancer as the test subject. In certain embodiments, the samples from the control subjects were taken from the control subjects before administration of the treatment.

In certain embodiments, the methods of developing a treatment plan for a test subject with cancer include a step of deriving a score from the comparison of the expression level of one or more microparticle-associated proteins from tumor-derived microparticles in the sample from the test subject with the expression level of one or more microparticle-associated proteins in samples from a plurality of control subjects, where the score indicates a level of similarity between the expression level of one or more microparticle-associated proteins from tumor-derived microparticles in the sample from the test subject and the expression level of one or more microparticle-associated proteins in samples from a plurality of control subjects The score may be, for example, a correlation coefficient.

In certain embodiments, a test subject may be chosen to participate in the clinical trial if the score indicates a significant level of similarity between the expression level of one or more microparticle-associated proteins from tumor-derived microparticles in the sample from the test subject and the expression level of one or more microparticle-associated proteins in samples from a plurality of control subjects who responded to the treatment being administered in the clinical trial. In other embodiments, a test subject may not be chosen to participate in the clinical trial if the score indicates a high level of similarity between the expression level of one or more microparticle-associated proteins from tumor-derived microparticles in the sample from the test subject and the expression level of one or more microparticle-associated proteins in samples from a plurality of control subjects who did not respond to the treatment being administered in the clinical trial.

In certain embodiments, choosing a test subject to participate in a clinical trial may also involve comparing the characteristics of tumor-derived microparticles from a test subject with the microparticles from a control subject. For example, a comparison of the number/concentration of tumor-derived microparticles from a test subject relative to the tumor-derived microparticles of a control subject may be used to choose a test subject to participate in a clinical trial.

EXAMPLES

The following examples are offered for illustrative purposes and to aid one of skill in better understanding the various embodiments of the disclosure. The following examples are not intended to limit the scope of the present disclosure in any way.

Example 1: Tenascin-C as an Extracellular Marker for Tumor-Derived Microparticles The following example demonstrates that Tenascin-C is a marker for tumor-derived microparticles. Isolation and analysis of microparticles shed from U87 brain cancer cells under normal conditions, serum-deprived conditions, or treated with the DNA alkylating agent temozolomide (TMZ) revealed robust abundance of Tenascin-C in these tumor-derived microparticles. Robust abundance of Tenascin-C persisted even in the presence of a genotoxic agent (TMZ) and growth of the U87 cells in a nutrient-deprived media.
Materials and Methods
Overview of Microparticles Harvested from Tumor Cell Lines-Experimental Outline U87 MG (ATCCR HTB 14™) cell cultures represent glioblastoma multiforme (GBM). Two Integra CELLine Bioreactors (Hudson, NH) were seeded from T-75 cultures of U87 into the 15 ml lower chamber, separated by a 10 kDa MWCO filter from a 500 ml upper reservoir chamber. After growth was established in the lower chamber containing exosome free fetal bovine serum (Exo-FBS Systems Biosciences, Mountain View CA), supernatant samples were recovered on a weekly basis. Upper chambers of the bioreactors were replenished with normal fetal serum-containing medium. The two cultures used were between 4 and 5 months old and were monitored for continued robust health.

On day 1 of the study, one Integra Bioreactor (Flask A) was provided with normal Eagles minimal essential medium (EMEM) supplemented with exosome-free foetal bovine serum FBS, while the other Integra Bioreactor (Flask B) was provided with EMEM alone. Additionally, fresh media was added to the upper chambers. Supernatant samples were taken at 2, 4, 6, and 24 hours after addition of fresh medium, mixed with protease inhibitor and Venceremin peptide reagent (New England Peptide, Gardner, MA) for incubation at 4° C.

Culture supernatants were collected at 24 hours. Fresh medium was added to both the lower and upper chambers adjusted to 100 µm TMZ was added (day 2) and supernatant samples taken as indicated above. The process was repeated at 48 hours with the exception that fresh media had been adjusted to 300 µm TMZ (day 3). The final collection of lower chamber supernatant occurred at 72 h.

Microparticles in the conditioned media were recovered from culture supernatants using one of the Venceremin peptides (New England Peptide, Gardner MA). Venceremins were originally identified as ligands with strong avidity for heat shock proteins, particularly HSP90 and of variable affinity to isoforms of HSP70, HSP60 and other chaperone proteins. To recover microparticles, the Venceremin peptide Vn96reverse, referred to as Heladonin (Hdn: H2N-LKLFEGLTLAGWSFRSLSLGRGKGQSP-OH; SEQ ID NO: 1), was used. The Integra Bioreactor lower chamber supernatant samples (2 mls) were mixed with 10 µl of protease inhibitor and 50 µg of Hdn peptide stock solution. Microparticles were prepared from Bioreactor supernatant samples taken at 2, 4, 6 and 24 hours after addition of fresh medium and placed at 4° C.

All samples were incubated for at least 18 h. The samples were processed by centrifugation (4500 g) washing in 1 ml of PBS and repeat centrifugation. The presence of U87 microparticles in material pelleted from the lower chamber of the cell cultures was determined by Western blotting.
Cell Culture Media Exosome-free fetal bovine serum (FBS) supplement was purchased from Exo-FBS Systems Biosciences, Mountain View CA. Eagles minimal essential medium (EMEM) supplied by ATCC Cat #30-2003.

For Flask A (SBI-EFM, nutrient-rich), prior to introduction of U87 cells into the bioreactor, the bioreactor was provided with Eagle's minimum essential medium+100 U/ml penicillin+100 µg/ml streptomycin (EMEM)+10% exosome-free fetal bovine serum FBS. After U87 cell introduction into the bioreactor, the bioreactor was cultured at 37° C. in a 5% carbon dioxide atmosphere. Upper chamber contains EMEM (90%) supplemented with regular fetal bovine serum (10%). A control bioreactor containing 15 mls of EMEM+Exo-free Medium placed at 37° C. was used. 2 mls were taken from the controls each day and replaced with fresh medium.

For Flask B (EMEM, nutrient-deprived), prior to introduction of U87 cells into the bioreactor, the bioreactor was provided with Eagle's minimum essential medium+100 U/ml penicillin+100 µg/ml streptomycin (EMEM). After U87 cell introduction into the bioreactor, the bioreactor was cultured at 37° C. in a 5% carbon dioxide atmosphere. Upper chamber contains EMEM only. A control bioreactor containing 15 mls of EMEM placed at 37° C. was used. 2 mls were taken from the controls each day and replaced with fresh medium.

Temozolomide (TMZ) Preparation

The MW of TMZ is 194.151 g/mol. 100 mg TMZ was dissolved in 5 ml of DMSO (20 mg/ml TMZ), which is equivalent to 20 µg/µl TMZ (257 mM). The stock solution of TMZ was used to provide TMZ at designated concentrations in the culture media of the bioreactor.

Day 1 Protocol—Introduction of Fresh Media to Bioreactor Culture (No TMZ)

For Flask A, the culture received fresh SBI Exosome-free serum supplemented media in lower chamber and regular FBS-supplemented media in the upper chamber. For Flask B, the Bioreactor cells were washed with two rinses of EMEM to remove prior serum supplemented media. Fresh EMEM was provided in both top and bottom chambers of the bioreactor. Both cultures were placed in a 37° C. incubator.

At 2, 4 and 6 h, the bioreactors were retrieved from the incubator and rocked gently for 1 min. 2 mls of media were removed from the lower cell chambers and transferred to 2.0 ml HANDEE microcentrifuge tube (PIERCE Rockland II) containing 5 µl of protease inhibitor (Cocktail III, EMD Merck Millipore). 2 mls of fresh media was added to upper chamber to compensate for removal. The retrieved volumes of supernatant (SN) were centrifuged at 17000 g for 5 m at 4° C. to pellet microparticulates and cell debris. 1.8 ml supernatant was transferred to a new tube taking care to avoid any pelleted material. The SN from each flask was mixed with 10 µl of Hdn peptide stock solution and incubated at 4° C. overnight for microparticle recovery. The cell and microparticle pellet (17000 g) was stored at −80° C.

Day 2 Protocol—Recovery of Microparticle Population and Introduction of New Media Containing 100 µM TMZ After 24 h the bioreactor flasks were retrieved from incubators and rocked gently for 5 m. All of the culture medium was retrieved from the lower cell chambers and immediately replaced with fresh EMEM+Exo-FBS (Flask A) containing 100 µM TMZ stock solution, or with fresh EMEM (Flask B) containing 100 µM TMZ stock solution. 100 µM TMZ was also added to the upper chambers.

For the 24 hour microparticle sample, 2 ml samples of SN were transferred to HANDEE tubes containing 5 µl of protease inhibitor as for the 2, 4 and 6 h samples and placed at 4° C. All remaining culture SN was frozen at −80° C. The cell free solutions serving as negative controls were also processed in an identical manner.

Day 3 Protocol—Recovery of Microparticle Population and Introduction of New Media Containing 300 µM TMZ Replacement of media and processing of samples for the collection of microparticles was conducted in the same manner for each Flask as day 2 with the exception that serum-supplemented EMEM (Flask A) and serum-free EMEM (Flask B) was adjusted to 300 µM TMZ in both the upper and lower chambers of the respective CELLine Bioreactor.

Day 4 Protocol—Final Collection of Culture Supernatant

Replacement of media and processing of samples for the collection of microparticles was conducted in the same manner as day 2 for each Flask with the exception that no further addition of TMZ was given to the cultures and the collection of lower chamber supernatant was considered the end of the experiment. The accumulated microparticle samples were stored at 4° C. for a minimum of 18 h for processing together on day 5 in preparation for gel electrophoresis.

Preparation of Microparticles

All SN samples stored at 4° C. with Hdn peptide and protease inhibitor were centrifuged at 4500 g for 5 m at 4° C. The SNs were utilized to isolate the microparticle pellets. Protein pellets were resuspended in 1 ml of PBS by vortexing and returned to the microcentrifuge for 5 m at 4500 g at 4° C. Protein pellets were prepared for electrophoresis by resuspension in a variant of Laemmli SDS buffer as previously described (Wubbolts R et al. *J Biol Chem.* 2003 Mar. 28; 278 (13): 10963-72).

The premixed 4× XT loading buffer (Bio-Rad) was adjusted to 4M urea, 25 mM TCEP (reducing agent; PIERCE) and 5 µl/ml of protease inhibitor (Cocktail III EMD Millipore). The electrophoresis sample/loading buffer was referred to as "USB" for urea sample buffer. Samples were incubated at 95° C. in a dry-heating block for 5 minutes, vortexed vigorously and given a 30 s spin in a microcentrifuge to bring down droplets and condensation.

Electrophoresis and Blotting Conditions

Frozen samples in SDS/Urea electrophoresis buffer were incubated at 95° C. for 30 seconds, vortexed and microfuged briefly. 25 µl volumes were applied to 10% XT Bis-Tris Criterion precast midi gels in XT-MES running buffer (all products Bio-Rad Hercules CA). Gels were run in Criterion modules (Bio-Rad) for approximately 55 minutes at 150 V. After electrophoresis was complete, the gels were rinsed in Towbin transfer buffer and layered onto supported nitrocellulose, blotting pads and paper (BioRad), all assembled into a blotting cartridge for insertion in the Criterion blotting module. The blotting module contained pre-chilled Towbin transfer buffer and an ice pack. Blotting was considered complete by running at 90V for 30 m. The blot was rinsed in distilled deionised water and processed with the Pierce reversible protein stain kit. The images were captured using a Bio-Rad Chemi-Doc using white light mode and allowed to dry.

Antibody Reactivity and Image Generation

The blots were destained to clear background by rehydration in ddH2O and use of destaining reagent (PIERCE). The blots were blocked for 30 minutes in 5% low-fat skim milk powder dissolved in phosphate buffered saline adjusted to 0.075% Tween™ 20 (TPBS).

The blots were cut longitudinally at the 37 kDa marker (i.e. perpendicular to the direction of electrophoresis) to allow for the same samples to be probed for low molecular weight (bottom) and high molecular weight proteins (top). Tenascin-C protein (~250 kDa) was detected using primary antibody 81C6, a Tenascin-C monoclonal antibody (Reardon D A, *Neuro Oncol.* 2008 April; 10 (2): 182-9).

Primary antibody was mixed with 3% milk dissolved in TPBS at a 1:2000 dilution and the blot incubated for 60 minutes, washed 4 times with an equal volume of TPBS, incubated by a 1:2000 dilution of horse-radish peroxidase (HRP) secondary antibody, washed 4 times for 10 minutes with TPBS. All incubations rocking and washes were conducted automatically with a Freedom Rocker device (Next Advance, Averil Park NY). The antibody-probed and TPBS washed blot halves were covered with 1 ml of Super Signal West Dura HRP substrate (PIERCE), covered with cling film and imaged using the Chemi-Doc at exposures between 2 s and 60 s depending on the signal intensity.

Results

Tenascin-C is a Marker of Tumor-Derived Microparticles

Table 1-1 illustrates the microparticle samples analyzed in the blot analyses from Flask A (SBI-EFM) and the corresponding lanes for the respective samples, the results of which are depicted in FIG. 1.

TABLE 1-1

Identification of Microparticle Samples
from Flask A in the Specified Blot Lanes

| Lane # | U87 Media and Microparticles Harvested from Flask A (SBI-EFM) |
|---|---|
| 1 | 5X dilution of MW standard |
| 2 | Controls + (SBI) 2 hours |
| 3 | Controls + (SBI) 4 hours |
| 4 | Controls + (SBI) 6 hours |
| 5 | Controls + (SBI) 24 hours |
| 6 | (SBI + 100 µm TMZ) 2 hours |
| 7 | (SBI + 100 µm TMZ) 4 hours |
| 8 | (SBI + 100 µm TMZ) 6 hours |
| 9 | (SBI + 100 µm TMZ) 24 hours |
| 10 | (SBI + 300 µm TMZ) 2 hours |
| 11 | (SBI + 300 µm TMZ) 4 hours |
| 12 | (SBI + 300 µm TMZ) 6 hours |
| 13 | (SBI + 300 µm TMZ) 24 hours |
| 14 | Blank |
| 15 | Control SBI Media 0 |
| 16 | Control SBI Media 1 |
| 17 | Control SBI Media 2 |
| 18 | Blank |

All samples appeared closely matched in overall intensity of total protein profile, with subtle variation in protein intensity at higher (e.g ~250 kDa) and lower (10-25 kDa) molecular weight (FIG. 1A, lanes 2-13). Protein was also recovered from the exosome-free serum product in the absence of cell material (FIG. 1A, lanes 15-17; SBI-EFM).

The Tenascin-C (Ten-C) protein analysis of samples from the nutrient-rich Flask A, (FIG. 1B), revealed a major 250 kDa band with minor bands migrating near the 150 kDa MW marker were observed. This study therefore presents the first recorded observation of Tenascin-C associated with shed tumor-derived microparticles. The Ten-C minor bands increased in intensity over the 2-6 hour sampling period, with the maximal increase seen at 24 hours. This Ten-C signal thus appears to follow the overall protein intensity seen at a comparable migration range. In addition, Ten-C abundance appears to have been minimally impacted by exposure to TMZ, with similar intensity of the minor band at 24 h post 0, 100 and 300 µM TMZ exposure (FIG. 1A, lanes 5, 9 and 13), and similar intensity of the major band throughout all time points and treatments (FIG. 1A, lanes 2-13). This data indicates that Ten-C may be used as an indicator of tumor-derived microparticles, as its abundance in U87-derived microparticles remains stable despite changing variables (e.g. time point, TMZ application).

Figure 2A:
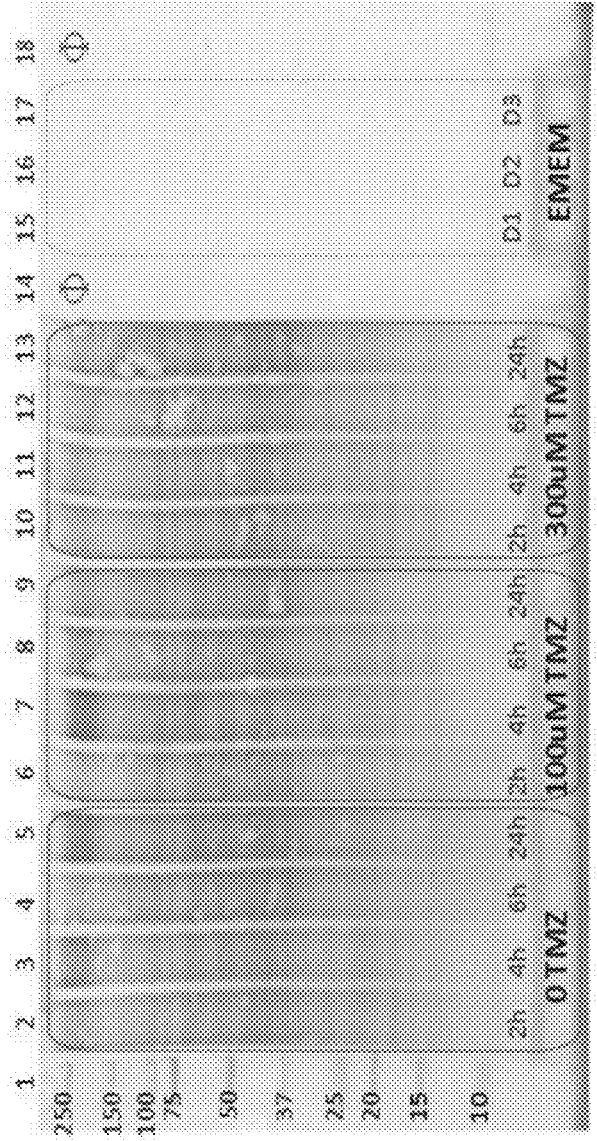
FIG. 2A illustrates a gel blot analysis of total protein content isolated from microparticles derived from U87 brain tumor cells that were grown in a nutrient-deprived media (EMEM) (Flask B). The total protein content from the various microparticle samples is shown as a function of time or exposure to the chemotherapeutic agent temozolomide (TMZ).

With regard to Flask B, Table 1-2 below illustrates the microparticle samples analyzed in the blot analyses from Flask B (EMEM) and the corresponding lanes for the respective samples, the results of which are depicted in FIG. 2.

TABLE 1-2

Identification of Microparticle Samples
from Flask B in the Specified Blot Lanes

| Lane # | U87 Media and Microparticles Harvested from Flask B (EMEM) |
|---|---|
| 1 | 5X dilution of MW standard |
| 2 | Controls + (EMEM) 2 hours |
| 3 | Controls + (EMEM) 4 hours |
| 4 | Controls + (EMEM) 6 hours |
| 5 | Controls + (EMEM) 24 hours |
| 6 | (EMEM + 100 µm TMZ) 2 hours |
| 7 | (EMEM + 100 µm TMZ) 4 hours |
| 8 | (EMEM + 100 µm TMZ) 6 hours |
| 9 | (EMEM + 100 µm TMZ) 24 hours |
| 10 | (EMEM + 300 µm TMZ) 2 hours |
| 11 | (EMEM + 300 µm TMZ) 4 hours |
| 12 | (EMEM + 300 µm TMZ) 6 hours |
| 13 | (EMEM + 300 µm TMZ) 24 hours |
| 14 | Blank |
| 15 | Control EMEM Media 0 |
| 16 | Control EMEM Media 1 |
| 17 | Control EMEM Media 2 |
| 18 | Blank |

In contrast to what was observed in Flask A (FIG. 1A), total protein of microparticles from U87 cells supplemented with EMEM and without serum (Flask B) exhibited differences in protein band presence most pronounced in the 37-75 kDa range. Protein was also recovered from the EMEM media in the absence of cell material (FIG. 2A, lanes 15-17; SBI-EFM).

Figure 2B:
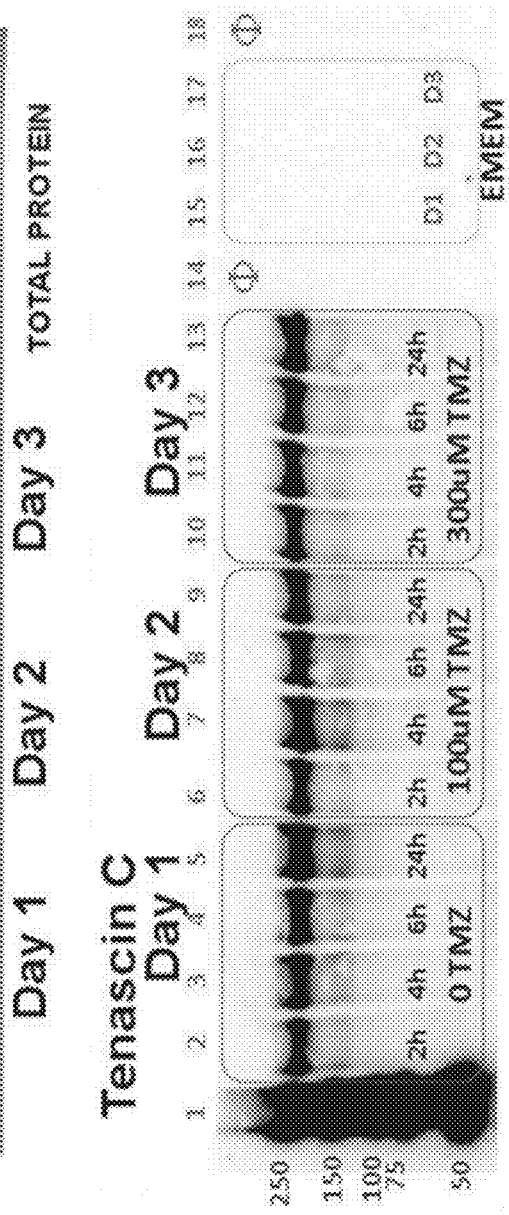
FIG. 2B illustrates a Western blot analysis of Tenascin-C protein present in the various microparticle samples as described in FIG. 2A.
Figures 3A, 3B, 3C, 3D, 3E, 3F:
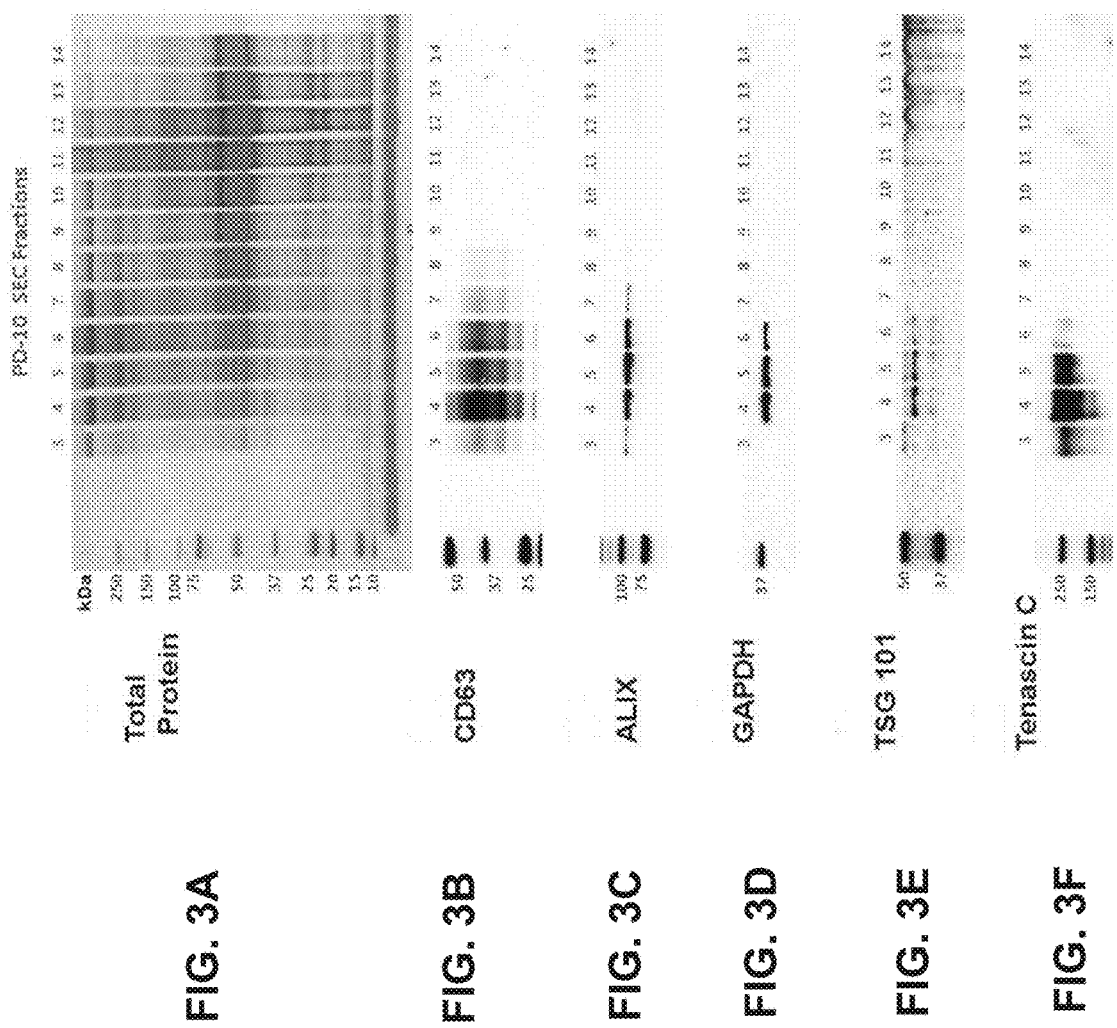
FIG. 3A illustrates a gel blot analysis of culture medium-derived total protein isolated from sequential 500 μl fraction eluates (labeled 3-14) from an SEC column using water as the mobile phase.
FIG. 3B illustrates a Western blot analysis of CD63 protein present in the sequential fractions from the same numbered fractions shown in FIG. 3A.
FIG. 3C illustrates a Western blot analysis of ALIX protein present in the sequential fractions from the same numbered fractions shown in FIG. 3A.
FIG. 3D illustrates a Western blot analysis of GAPDH protein present in the sequential fractions from the same numbered fractions shown in FIG. 3A.
FIG. 3E illustrates a Western blot analysis of TSG 101 protein present in the sequential fractions from the same numbered fractions shown in FIG. 3A.
FIG. 3F illustrates a Western blot analysis of Tenascin-C protein present in the sequential fractions from the same numbered fractions shown in FIG. 3A.

Similar to what was observed in Flask A, Tenascin-C protein was robustly present in microparticles shed from U87 cells in the nutritionally-deprived Flask B and its abundance was not impacted by TMZ application or time point (FIG. 2B). Indeed, even in the nutritionally challenged cultures, Ten-C-containing microparticles were continuously released from the glioblastoma bioreactor culture and robustly express Ten-C. It is noted that Tenascin-C protein signal from Flask B was somewhat lower than the Ten-C levels observed in Flask A. Without wishing to be bound by theory, it is believed that this decrease in Ten-C abundance in Flask B relative to Flask A is reflective of decreased microparticle release imposed by the switch to the lower nutrient medium of Flask B. Despite this, the overall similarity of Ten-C signal between Flasks A and B, in terms of robust abundance, bears testament to the seemingly mild impact of the U87 bioreactor culture on Ten-C protein abundance in shed tumor-derived microparticles, with similar protein intensities observed in both flasks at 2, 4, 6 and 24 hours and further in the presence of genotoxic TMZ (FIG. 2B, lanes 2-13).

Figure 1B:
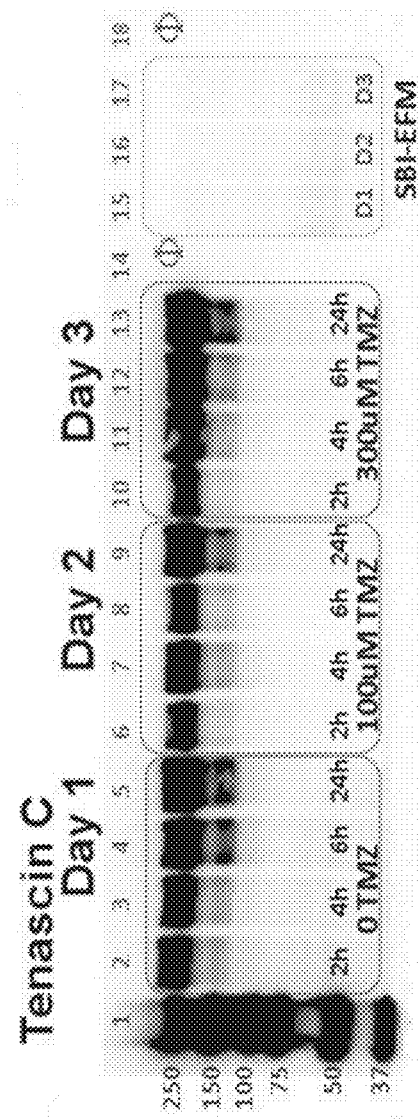
FIG. 1B illustrates a Western blot analysis of Tenascin-C protein present in the various microparticle samples as described in FIG. 1A.

Overall, the Ten-C protein abundance data from Flasks A and B support that Ten-C may be used as an indicator of tumor-derived microparticles. Ten-C abundance remained robust regardless of the nutrient conditions of the U87 cell culture (FIG. 1B and FIG. 2B). Further, in both Flasks A and B, Ten-C abundance is shed tumor-derived microparticles remained stable over time and was not altered by application of the genotoxin TMZ.

Example 2: Two-Step Recovery of Microparticles Bound to Size Exclusion Chromatography (SEC) Columns and Identification of Tenascin-C The following example demonstrates that microparticles may be effectively recovered from a serum-containing sample using a two-step purification method in a size exclusion chromatography (SEC) column. The use of water as a first mobile phase, followed by an arginine-containing solution as a second mobile phase, resulted in controlled elution and separation of microparticles from other sample components. Further, Tenascin-C was identified in the U87-derived microparticle-containing fractions eluted from the column.

Materials and Methods
PD-10 Fractionation of Serum

Microparticles to be peptide recovered were prepared by retrieving two separate, 1 ml volumes of glioblastoma U87 bioreactor culture medium from refrigerated storage (containing 0.04% sodium azide and 5 µl/ml of Protease Inhibitor Cocktail III, EMD Millipore). 10 µl of Hdn peptide stock solution (5 µg/µl in Extraction Buffer 1 from the sub-cellular proteome extraction kit, EMD Millipore) was added to the microparticle-containing culture medium and incubated overnight at 4° C. to recover the microparticles.

Peptide-recovered microparticle preparations were centrifuged at 4° C. for 5 minutes at 4500 g. The culture medium supernatant was completely removed (i.e. Quick spin to remove residual supernatant by P-20). One tube containing pelleted and washed microparticles received 1 ml of AB Serum, while the other tube had microparticles resuspended in 1×PBS. Next, 5 µl of protease inhibitor was added to both tubes and mixed. Separately, 1 ml of control serum was mixed with 5 µl of protease inhibitor (Cocktail Set III, EMD Millipore). The microparticle resuspensions were suspended as vigorously as possible first by vortexing and then pipetting up and down with a P-1000 set at 500 µl.

Following microparticle resuspension, both serum samples were placed at 37° C. for 15 minutes, mixed by vortexing and incubated without agitation for 10 mins at room temperature and mixed again by vortexing. Both AB serum samples were introduced to water-equilibrated agarose PD-10 columns. 500 µl volumes of water were added to the column to permit collection of 16 separate 500 µl fractions.

Immediately following the collection of 16 water fractions, 16 separate 500 µl volumes of arginine solution were added and the eluates collected. The arginine solution contained 1M arginine that had been adjusted to pH 7.2 with 1M hydrochloric acid at a reduced volume with ddH$_2$O and then made 5% ethanol (v/v).

The eluted fractions were precipitated by the addition of ⅑ volume of 100% trichloroacetic acid (TCA) incubation on ice for 15 minutes and pelleting by microcentrifuge. The supernatant was discarded and the pellet washed with 80% acetone 10 mM Tris HCl, microcentrifuged, and the pellet drained of supernatant for addition of electrophoresis sample buffer. Microparticle pellets were prepared for electrophoresis by resuspension in a variant of Laemmli SDS buffer as described by Wubbolts et al., 2003. The premixed 4× XT loading buffer (Bio-Rad) was adjusted to 4M urea and 5 µl/ml of protease inhibitor (Cocktail III EMD Millipore) was added to generate urea sample buffer, or "USB."

250 µl of non-reducing USB with was added immediately after the last acetone wash of the water eluates. 80 µl was used to resolubilise the pellets from the arginine eluates to account for smaller volume of precipitated material observed. Samples were incubated at 95° C. in a dry-heating block for 5 minutes, vortexed vigorously and given a 30 s spin in a microcentrifuge to bring down droplets and condensation. Standards consisted of 5 fold dilution of molecular weight standards (Precision Plus, BioRad, Hercules, CA) for lane 1 and U87 microparticles (U87 Prex) as a standard control for lane 18.

Solubilised material was applied to Criterion Gel 10% XT-Bis Tris with XT-MOPS buffer (Bio-Rad). Completed gels were transferred to supported nitrocellulose and total protein transfer Pierce reversible protein stain kit (PIERCE ThermoFisher). Blots were destained and blocked in 5% skimmed milk powder dissolved in phosphate buffered saline containing 0.075% Tween™ 20 (TPBS). Blots were cut longitudinally at the 50 kDa standard and probed with antibodies for CD63 and Tenascin-C.

Results
Elution of Microparticles from Culture Medium Using an SEC Column

Experiments were performed using a PD-10 column (GE Healthcare) containing 10 mls of 2% agarose (ABT beads, Tampa, FL) for use in size exclusion chromatography (SEC) of glioblastoma cell line U87 culture medium. Specifically, the objective was to enrich microparticles, which were shed by U87 into the lower chamber of Integra CELLine bioreactor (Hudson, NH) in the agarose column. The microparticle-enrichment approach was based on a previously published method (Gercel-Taylor C et al., Anal Biochem. 2012 Sep. 1; 428 (1): 44-53) with the exception that a 1:10 culture medium sample to agarose bed volume ratio was used and distilled deionized water (ddH$_2$O) was used as the mobile phase.

U87 microparticles were identified by Western blot following trichloracetic acid (TCA) precipitation of 500 µl volume fractions collected as serial eluates (FIG. 3A-FIG. 3F). Signals from microparticle proteins including CD63, ALIX, GAPDH, TSG 101, and Tenascin-C (FIG. 3B-FIG. 3F) were observed in fractions 4-6 of a 16 fraction series. Reproducibility was addressed by conducting the experiment a further four times and identifying the consistent presence of microparticle marker CD63. The experiment demonstrated that miniaturized (PD-10 based) water SEC can enrich microparticles away from a large proportion of serum proteins in the culture medium (FIG. 3). However, bioreactor medium is far more concentrated in microparticles than tissue fluid (Clayton and Webber, 2013, Journal of Extracellular Vesicles, 2:19861). Accordingly, experiments were designed to determine not only whether the PD-10 column approach could enrich microparticles from undiluted serum (as opposed to culture medium), but also to investigate whether microparticles bind to the column when isolated from undiluted serum.

Elution of Microparticles from Serum Using an SEC Column with Arginine Washes

Experiments were performed to investigate microparticle elution from undiluted serum using an SEC column with arginine washes. Peptide-recovered microparticles were centrifuged out of the culture supernatant, washed by resuspension in PBS, centrifuged back into a pellet and resuspended in 1 ml of a commercial source of human male plasma (Serum AB Sigma Aldrich), and samples loaded onto a PD-10 column. The collection of sequential fractions having water was the mobile phase was followed by the collection of sequential fractions having an arginine-containing solution as the mobile phase. The objective was to reveal the potential for microparticles to bind to the column under these conditions, as well as whether serum proteins could be eluted away from microparticles under these conditions using the PD-10 column. The protocol was a direct addition of an arginine-containing solution immediately following the application of ddH$_2$O. Briefly, immediately following the collection of 16 separate, 500 µl fractions, the same volume of 1 M arginine solution was added to the column for the collection of the 16 separate, 500 µl fractions. The arginine fractions were similarly precipitated in 500 µl fractions by TCA and analyzed by blot for total protein and the presence of CD63 and Tenascin-C.

Figure 5A:
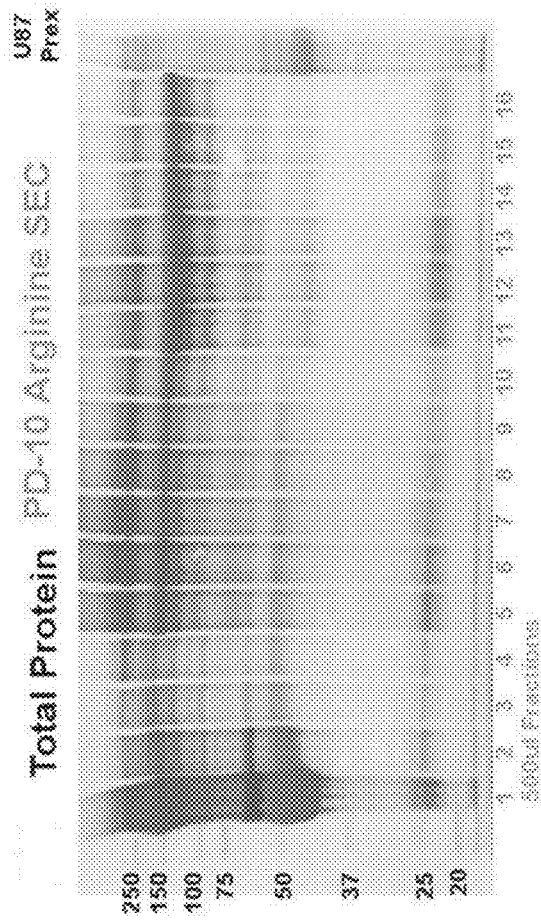
FIG. 5A illustrates a gel blot analysis of serum-derived total protein isolated from sequential 500 μl fraction eluates (labeled 1-14). Following fraction elution from the column using water as the mobile phase, an arginine-containing solution was added to the column, and sequential 500 μl fraction eluates from an SEC column were collected and total protein stained from each fraction as shown.

The resulting total protein profiles representing fractions eluted from the PD-10 column are shown in FIG. 4A for water and FIG. 5A for the arginine-containing solution. It was observed that addition of the arginine-containing solution to the PD-10 column liberates protein from the column (FIG. 5A). The first evidence of material eluted from the agarose by the arginine-containing solution is reflected by a difference in the protein profile in fraction 5 of FIG. 5A and the preceding fractions (e.g. fractions 2-4), where more total protein is present in fraction 5 than in preceding fractions 2-4. Application of the arginine-containing solution thus provides evidence of controlled column binding and elution of material on agarose media. The arginine-mediated release of the material bound by the column present in fraction 5 of FIG. 5A would thus have been absent from fractions referred to as peak 1 and peak 2, where peak 1 was considered the void volume of 2% agarose water size exclusion chromatography (SEC) and considered a likely point of egress for microparticles.

The total protein profile of the water SEC fractions illustrates the presence of a limited number of highly abundant serum proteins as observed in FIG. 4A. Without wishing to be bound by theory, it is believed that these predominant serum proteins are likely to include immunoglobulins that may be permutations of the complete monomer (2 heavy chains and 2 light chains, 150 kDa, FIG. 4A, lane 16 band 1) and individual chains (FIG. 4A, lane 16 bands 2, 4 and 5). Further, and without wishing to be bound by theory, it is believed that albumin is the identity of band 3 (FIG. 4A). With the exception of 150 kDa protein bands, the highly abundant proteins observed in FIG. 4A are generally relegated to minor or contributing status upon elution with arginine-containing solution, as can be seen in FIG. 5A.

Figure 5B:
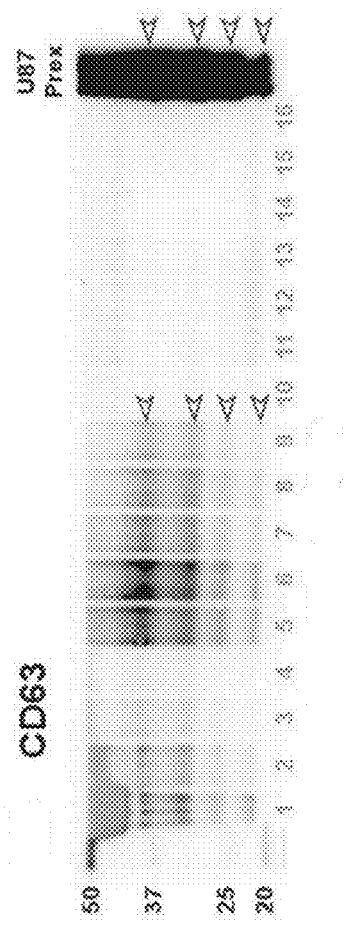
FIG. 5B illustrates a Western blot analysis of CD63 protein present in the sequential fractions from the same numbered fractions shown in FIG. 5A.

Of particular significance, CD63 protein was detected in the eluate of fraction 5 of FIG. 5A. CD63 is an unambiguous microparticle-associated protein observed to be strongly expressed in U87 derived microparticles (FIG. 5B, lane U87 Prex). Without wishing to be bound by theory, it is believed that the multiple bands observed in FIG. 4B are typical of CD63 due to post translational glycosylation (Latysheva N et al., Mol Cell Biol. 2006 October; 26 (20): 7707-18). Four discrete CD63 bands were observed from U87 microparticles as indicated by open arrow heads. Importantly, the observation of an increase in the abundance of CD63 in the arginine-containing solution fractions indicates that microparticles are bound to the agarose media during chromatography of undiluted serum with water (FIG. 4B).

The CD63 signal is so strong in the control lanes consisting of U87 Prex (U87 peptide-recovered microparticles collected directly from bioreactor culture medium) that individual bands merge into one another (FIG. 4B and FIG. 5B, U87 Prex). It was thought that a similar amount of peptide-recovered microparticles would have been resuspended in the AB serum samples that were loaded onto the SEC column and that CD63 would be of greater intensity in material liberated from agarose by arginine. Without wishing to be bound by theory, it is believed that the reason the arginine-eluted fractions do not have similar CD63 intensity as the control lane (containing isolated microparticles) is that proteins eluted from the column by the arginine-containing solution may have included many serum proteases, given that protease inhibitor was not added to the arginine-containing solution and given the large number of proteases expected to be present in serum.

Tenascin-C Identified in Column Elution of U87-Derived Microparticles

Figure 5C:
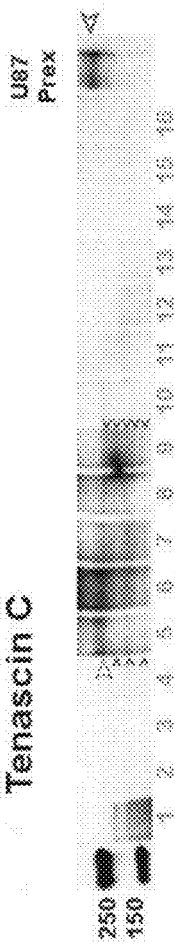
FIG. 5C illustrates a Western blot analysis of Tenascin-C protein present in the sequential fractions from the same numbered fractions shown in FIG. 5A.

To assess what impact a potentially proteolytically active environment may have had on Tenascin-C abundance in the arginine fractions, blots were probed for the presence of Tenascin-C. It was determined in a parallel study of U87 cell sensitivity to temozolomide that Tenascin-C is highly abundant and insoluble with the majority, requiring a strong detergent to remove this protein from the cell during differential detergent solubilisation. The results of Tenascin-C antibody probing of the arginine fractions shown in FIG. 5C confirm the abundance of Tenascin-C in microparticles, partial protection from proteases, and the generation of fragments. Importantly, the appearance of Tenascin-C in the same fractions as CD63 corroborates that U87-derived microparticles were bound to the agarose and eluted with an arginine wash. Overall, the data support that Tenascin-C is abundant in tumor-derived microparticles and can survive proteolytically challenging environments.

Importantly, it was found that the addition of arginine-containing solution released serum proteins from the PD-10 column that would have otherwise gone undetected; without the addition of arginine, these proteins may have remained bound to the column. Further, the unbound fractions included the majority of the signal for U87 microparticle-associated proteins CD63 and Tenascin-C. Overall, the experiment indicates that extracellular microparticles are bound to agarose matrix during chromatography with water as the mobile phase (FIG. 4) and that the addition of an arginine-containing solution following the water phase improved protein release from the column and enrichment of microparticles (FIG. 5). As such, the removal of the vast majority of serum proteins using water and the retention of extracellular microparticles using arginine may represent a novel and robust means of bench-top preparation of microparticles from a sample.

Example 3: Direct Affinity Pulldown of Tenascin-C Positive Microparticles from U87 Culture Medium Incubated with Protein Solubilizing Buffer "LaurA"

The following Example demonstrates the influence of increasing concentrations of a protein solubilizing buffer ("LaurA") on the protein profile of Tenascin-C and other antigens from affinity captured microparticles from U87 cell culture medium by either the peptide recovered microparticle (PREX) reagent Vn96, or an anti-Tenascin C monoclonal antibody (81C6).

Introduction

It was seen from Examples 1 and 2 that Tenascin-C protein was robustly associated with U87-derived microparticles, suggesting that Tenascin-C may be used as a robust extracellular marker of tumor-derived microparticles. Without wishing to be bound by theory, it is thought that exposure of Tenascin-C (TNC) on microparticles may be able to be improved by removing background protein contamination. To this end, Applicants explored the use of a protein solubilizing buffer, called "LaurA," to assist in removing background proteins. U87-derived microparticles present in U87 cell culture media were incubated with different concentrations of LaurA. Microparticles present in the culture media were then subjected to direct affinity pulldown via incubation with either the peptide recovered microparticle (PREX) reagent Vn96, or with a monoclonal antibody to Tenascin-C (81C6), followed by centrifugation and protein analysis.

Materials and Methods
Cell Culture

A cell culture of the gliobastoma U87 cell line was established in an Integra CELLiNE bioreactor as described in Examples 1 and 2. After cell growth in the culture, culture media was harvested as described above.

LaurA, Affinity Pulldown, and Microparticle Preparation 1 mL volume replicates of 10%, 20%, 30%, 40%, 50% and 60% LaurA solutions were prepared. The LaurA solution is composed of 1% vol/vol Lauroyl glutamate (BOC Sciences Creative Dynamics Inc. Shirley, NY) and 0.8M arginine (Sigma Aldrich St Louis MO) adjusted in ddH$_2$O mixed with protease and RNAse inhibitors and adjusted to 0.04% sodium azide. Each of the 1 mL LaurA aliquots were incubated with 1 mL of the recovered cell-free glioblastoma U87 culture medium (described above). Replicates of the LaurA/U87 cell culture medium solutions were mixed and incubated with either 50 µg of the Vn96 peptide (peptide recovered microparticle reagent, or "PREX"), or were incubated with 20 µL of the anti-TNC antibody 81C6.

Electrophoresis, Blotting, and Image Generation

The mixtures were incubated for 96 hours at 4° C. Following incubation, in order to pellet material cross linked by the microparticle-recovery peptide (PREX) or the anti-TNC antibody, the mixtures were centrifuged at 4500 g for 10 min. at 4° C. The supernatants were removed and placed at 4° C. Pelleted material was washed by vortex resuspension in 1 mL of 50 mM arginine glutamic acid solution containing protease and RNase inhibitors. 500 µL of material was removed and placed at 4° C., while the remaining 500 µL of the suspension was centrifuged at 4500 g for 10 m at 4° C. The supernatant was discarded and the pellet was resuspended in 100 µL of urea/SDS electrophoresis sample buffer (USB). Individual samples were split to prepare 50 µL reduced and non-reduced aliquots. Reduced samples received 3 µL of TCEP reducing agent (PIERCE, Rockland Il); non-reduced samples received 3 µL of ddH$_2$O. Both reduced and non-reduced samples were denatured and prepared for electrophoresis by heating to 95° C. for 5 min and vortexing. If USB-containing samples were not being used on the same day as preparation, they were frozen. On the day of blotting, samples were removed from the freezer and heated at 95° C. for 5 min. For controls, or for repeat runs, samples were heated for 1 minute before loading.

20 µL volumes of USB solubilized affinity pellet material were loaded onto Criterion 18-well 4-12% XT Bis-Tris gels (Bio-Rad, Hercules, CA) with Precision molecular weight standards (Bio-Rad), electrophoresed and transferred to PVDF membrane (Western blot). Electrophoretically resolved protein bands transferred to the membrane were observed using the Pierce Reversible Protein Stain Kit for Membranes (PIERCE Rockland Il). Blots were cut longitudinally to allow for independent incubation of discrete antibodies within relevant molecular weight size range of target proteins. The blots were then destained, blocked with Pierce Protein-Free Blocking Buffer (PFBB), and incubated overnight at 4° C. with solutions of antibody diluted in PFBB. Antibodies directed to the proteins are indicated in FIG. 6A-FIG. 6H. The blots were washed 3 times for 10 minutes in phosphate buffered saline containing 0.075% Tween™-20 (TPBS) and probed with appropriate secondary species-specific antibody labelled with horse radish peroxidase (HRP) diluted in PFBB, washed 3 times in TPBS, and incubated in Supersignal West Dura Chemiluminescent Substrate (PIERCE). Imaging was conducted with a ChemiDoc MP System (Bio-Rad).

Figure 6G:
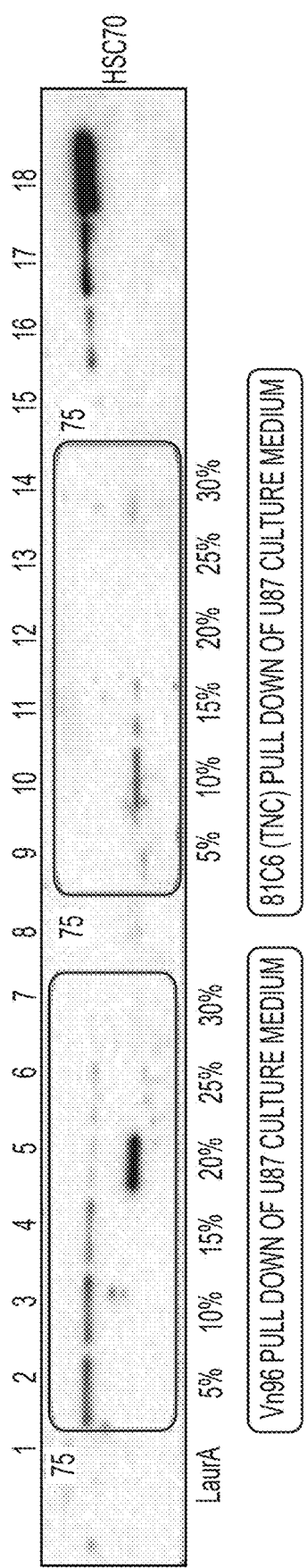
FIG. 6G illustrates a blot analysis of heat shock protein 70 (HSP70) protein isolated from Vn96 or 81C6 pulled down microparticle samples.
Figure 6H:
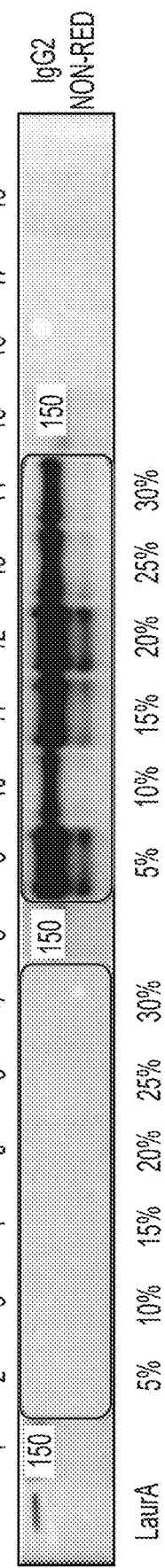
FIG. 6H illustrates a blot analysis of IgG2 protein isolated from Vn96 or 81C6 pulled down microparticle samples.

Results from the above described protein analysis are presented in FIG. 6A-FIG. 6H. The lane order of FIG. 6A-FIG. 6H is identical; Lanes 1, 8 and 15 consist of 5 µL Precision molecular weight standards (Bio-Rad). Lanes 2-7 represent material pulled down by centrifugation after incubation in the final dilution of LaurA buffer indicated and with the PREX agent Vn96. LaurA dilutions are: lane 2, 5%; lane 3, 10%; lane 4, 15%; lane 5, 20%; lane 6, 25% and lane 7, 30%. Lanes 9 through 14 are identical to lanes 2 to 7 with the exception that the mixtures were incubated with the anti-Tenascin C monoclonal antibody, 81C6. For example in the instance of FIG. 6A, the blot contains material pulled down by PREX reagent Vn96 (lanes in far-left square) and anti-TNC 81C6 (lanes in far-right square) from the dilutions of LaurA indicated below each figure. Sections of the blot of appropriate molecular weight range were probed with the primary antibody to proteins as indicated, abbreviations as follows: FIG. 6A, TNC, tenascin C (81C6, the same antibody used as the affinity reagent in lanes 9-14); FIG. 6B, FN IST1, total fibronectin (non-reducing conditions); FIG. 6C, CD63, tetraspanin lamp 3 (non-reducing conditions; FIG. 6D, cFN cellular or oncofetal fibronectin (antibody IST-9); FIG. 6E, GAPDH, glyceraldehyde phosphate dehydrogenase; FIG. 6F shows total protein profile obtained by Pierce Reversible Protein Stain Kit for Membranes; FIG. 6G, HSC70, heat shock protein 70; FIG. 6H, IgG2, immunoglobulin G clonotype 2. Controls include in lane 16, PREX prepared by incubation of 50 µg peptide Vn96 with 1.8 mLs of U87 bioreactor medium followed by pelleting, washing and resuspension in urea/SDS buffer as previously described. Lanes 17 and 18 were loaded with 5 µg of commercially obtained cell lysates of U87 and T98 (Santa Cruz Biotech).

Results

Table 3-1 illustrates the microparticle samples analyzed in the blot analyses following affinity pulldown of microparticles from the LaurA/culture medium mixtures, and the corresponding lanes for the respective samples, the results of which are depicted in FIG. 6A-FIG. 6H. The lane order of FIG. 6A through FIG. 6H is identical.

TABLE 3-1

Identification of Microparticle Samples or Condition in the Specified Blot Lanes

| Lane # | Microparticle Sample or Condition |
| --- | --- |
| 1 | MW standard |
| 2 | 5% LaurA + Vn96 |
| 3 | 10% LaurA + Vn96 |
| 4 | 15% LaurA + Vn96 |
| 5 | 20% LaurA + Vn96 |
| 6 | 25% LaurA + Vn96 |
| 7 | 30% LaurA + Vn96 |
| 8 | MW Standard |
| 9 | 5% LaurA + 81C6 |
| 10 | 10% LaurA + 81C6 |
| 11 | 15% LaurA + 81C6 |
| 12 | 20% LaurA + 81C6 |
| 13 | 25% LaurA + 81C6 |
| 14 | 30% LaurA + 81C6 |
| 15 | MW Standard |
| 16 | U87 PREX (Vn96) |
| 17 | U87 cell lysate |
| 18 | T98 cell lysate |

FIG. 6A-FIG. 6H present the results of proteins analyzed from microparticles that were incubated with various concentrations of the protein solubilizing agent, LaurA, followed by direct affinity pulldown. Direct affinity pulldown in this instance refers to pelleting by centrifugation, rather than by the use of beads or other support reagents. Affinity pulldown reagents used were either the peptide recovered microparticle (PREX) reagent Vn96, or a monoclonal antibody to Tenascin-C (81C6).

FIG. 6A demonstrates the analysis of Tenascin-C following the procedures described above. With regard to the Vn96-pulled down samples (Lanes 2-7 of FIG. 6A), the major Tenascin-C band remains relatively stable up to a LaurA concentration of 15% to 20%, at which point the pellet contains two thinner bands of slightly higher molecular weight. The concentration of the LaurA solution thus appears to affect the integrity of the major 240 kDa TNC band at higher concentrations. This data suggests that a LaurA concentration of between 15% and 20% is promoting removal of Tenascin-C from microparticles. Turning to the anti-Tenascin C mAb 81C6-pulled down samples (Lanes 9-14 of FIG. 6A), the major Tenascin-C remains relatively stable only up to a LaurA concentration of 5%, at which point the high molecular weight Tenascin-C takes the form of two higher molecular weight isoforms or aggregates between concentrations of 5% and 10% LaurA. These observations suggest that the Tenascin-C antibody pulldown is not as effective as the Vn96 PREX pulldown when LaurA is present in the sample, at least at higher concentrations of LaurA.

Turning to extracellular matrix (ECM) proteins total fibronetic (FN IST1-both high molecular weight and primary isoform detected) and oncofetal fibronectin (cFN), both of these proteins are considerably reduced in intensity between 5% and 10% LaurA (FIG. 6B and FIG. 6D). Indeed, in the Vn96-pulled down samples, the cFN band has been completely removed from the pelleted material between 5 and 10% LaurA. In the microparticles pulled down with the 81C6 antibody, fragments of FN are detected at concentrations of LaurA between 10% and 15% (FIG. 6D). The decrease in protein pulldown by the antibody after 10%-15% suggests an avidity threshold where the solubilization power is greater than that of the mAb affinity. These observations suggest that loosely associated extracellular matrix proteins may be removed by LaurA incubation, even at concentrations of LaurA between 5% and 10%.

The reduction in PREX pulldown of TNC is matched by the intensity of the microparticle membrane protein CD63 at similar concentrations of LaurA (FIG. 6C). The four discrete bands present in the CD63 blot are familiar isoforms of CD63, which is a membrane spanning protein. However, it is clear that this protein can be removed from microparticles starting at LaurA concentrations of between 5% and 10%. The most intense representation of the four CD63 isoform bands become gradually reduced as LaurA concentration increases in both the Vn96 and 81C6 pulldowns, suggesting that as the concentration of LaurA increases, external proteins are released from microparticles.

The concentrations of glyceraldehyde-3-phosphate dehydrogenase (GAPDH) were also probed. Unlike some of the external proteins described above, GAPDH is an internal (lumenal) protein and is not thought to exist on the outer surface of microparticles. As can be seen in FIG. 6E, the levels of GAPDH in Vn96 pulldown samples remain relatively stable up to at least 15% LaurA, at which point concentrations of LaurA above 15% appear to reduce (although never completely eliminate) GAPDH levels. The steady presence of GAPDH at 15% LaurA indicates that the internal contents of U87 microparticles are protected from escape, at least at concentrations of LaurA below 15%, which illustrates remarkable recovery of this protein. Regarding GAPDH levels in the 81C6 pulldowns, the lack of GAPDH detection at even the lowest concentration of LaurA suggests that this protein may have been below detection limits, or possibly that the 81C6 antibody is pulling down anything strongly associated with Tenascin-C and at solubilizing conditions, which may not include the entire contents of microparticles.

The protein levels of HSP70 (heat shock protein 70, H-300: multiple isoforms) were also examined (FIG. 6G). In the Vn96 pulldowns, HSP70 shows no change in intensity at 5% and 10% LaurA. Interestingly, full-length HSP disappears as the predominant form at LaurA concentrations of 20% and a smaller 54 kDa form of HSP70 appears, similar to what was observed for Tenascin-C. Further, the smaller 54 kDa form of HSP70 was the only form observed in the 81C6 pulldowns.

The protein levels of immunoglobulin G2 (heavy and light chains), or Ig2H2L, were also examined (FIG. 6H). Ig2H2L could only be detected in the samples pulled down using the anti Tenascin-C antibody 81C6, which is an IgG2a monoclonal antibody. These results that the Vn96 (PREX) peptide, when used for microparticle pulldowns, produces a remarkably clean IgG-free protein population.

FIG. 6F shows the total protein stains from the samples that were probed for specific proteins using the specific antibodies as described above. Interestingly, despite the earlier removal of cellular Fibronetic and Tenascin-C, the Vn96 peptide continues to pellet material with a comparable protein profile intensity (compare lanes 2 and 7 of FIG. 6F). Without wishing to be bound by theory, it is thought that these may be extremely clean microparticle preparations. This observation is supported by the fact that it is still possible to detect GAPDH at LaurA concentrations of 30% (what is considered to be an internal, or lumenal, protein). Also, between LaurA concentrations of 15% and 20%, some protein liberation appears to be occurring. Note also that total protein continues to be pelleted by PREX at 30% LaurA concentrations, whereas pelleted material becomes weaker in abundance between 15% and 25% LaurA concentrations, suggesting less pulldown by mAb 81C6 between 15 and 25% LaurA. With regard to the protein profiles of 81C6-pulled down samples, while the Vn96 peptide continues to bind tenaciously to membrane particles at higher concentrations of LaurA, with the 81C6 anti-TNC antibody, protein concentrations reduce to negligible levels by 30% LaurA. This reduction suggests an avidity threshold: effective affinity pelleting of Tenascin-C positive microparticles at concentrations of LaurA between 5% and 10%, but prohibitive to such pelleting at higher levels of LaurA.

Overall, the data suggests that Vn96 (PREX) pulldown may be used to produce a remarkably clean, IgG-free, Tenascin-C positive microparticle pellet from U87 culture medium using LaurA at lower concentrations of 5-10%, although optimization of LaurA concentrations may also be attempted. Pulldowns using anti-Tenascin C antibody 81C6 may also be used, although with reduced effectiveness relative to PREX pulldowns.

Further, gradients of LaurA concentration as shown in FIG. 6A-FIG. 6H appear useful for removing loosely associated protein from TNC- and ECM-coated microparticles using affinity reagents and ligands, such as monoclonal antibodies, lectins and peptides, and for determining the strength of association of proteins with microparticles. LaurA may also be a useful dispersing agent and dissembler of microparticle surface proteins including TNC and ECM proteins like FN, while interior proteins remain relatively stable. The concentration of LaurA is likely adjustable given specific needs to give a suitable background protein removal profile. Tenascin-C positive microparticles removed using the methods described in this Example may be useful for analyzing the protein and nucleic acid contents of such microparticles.

Example 4: Mass Spectrometry Identification of Tenascin-C in Tumor-Derived Microparticles This Example demonstrates that Tenascin-C is represented by a large number of peptides (Pep) in the peptide recovered microparticles (Vn96, or PREX) of both U87 and HEK293T cell cultures. Tenascin-C was identified among the top 15 proteins identified by discrete peptides found in microparticles from U87 and 293T cell cultures as determined by Orbitrap mass spectrometry conducted at Dalhousie University, Halifax, Nova Scotia. Results are shown below in Table 4-1 (for microparticles from U87 cells) and Table 4-2 (for microparticles from HEK293T cells).

TABLE 4-1

Tenascin-C identifed among U87 microparticle proteins by individual peptide number (PEP) from PREX by mass spectrometry

| Hit Number | Gene | Description | Pep |
|---|---|---|---|
| 3 | TNC | Tenascin C | 35 |

TABLE 4-2

Tenascin-C identified among HEK 293T microparticle proteins by individual peptide number (PEP) from PREX by mass spectrometry

| Hit Number | Gene | Description | Pep |
|---|---|---|---|
| 4 | TNC | Tenascin | 34 |

From Table 4-1 and Table 4-2, Tenascin-C is identified in the top 15 most abundant proteins present in microparticles in two different tumor or tumor-like cell lines. U87 is a model glioma cell line, and HEK293T is a model highly proliferative renal cell line. This Example further suggests that Tenascin-C may be used as an extracellular marker of tumor-derived microparticles.

Example 5: Reactivity of Tenascin-C Antibody in RIPA Lysates and Peptide Recovered Microparticles from 293T, HELA, and U87 Cell Lines The following Example demonstrates that when RIPA buffer cell lysates and peptide recovered microparticles (using Vn96, or PREX) from 293T, HELA, and U87 cell lines are probed with an anti-Tenascin-C antibody by Western blot, recovered microparticles from 293T and U87 show strong signals of Tenascin-C at the expected molecular weight of approximately 240 kDa. The strength of the immunoreactive signal of TNC in 293T and U87 has likely subdued the weaker signals in HELA cells, as the protein has been seen before in other HELA fractions at higher exposure.

Materials and Methods

The cell lines used are from different tumor or tumor-like cell lines, including a cervical cancer model cell line (HELA), a glioma model cell line (U87), and a model highly proliferative renal cell line (HEK293T). Western blots of 293T, HELA or U87 cellular lysates were prepared using radioimmunoprecipitation assay buffer (RIPA buffer, containing protease inhibitor) or prepared from bioreactor culture medium by microparticle recovery peptide reagent Vn96 (see previous Examples).

Radioimmunoprecipitation assay buffer (RIPA buffer; containing protease inhibitor) lysates were prepared from cell monolayers in T75 flask cultures of 293T, HELA and U87 cells. The culture medium was removed from the cell monolayers and the remaining monolayer was rinsed in PBS. Cells were loosened from flasks by a cell scraper, removed by pipette, and vortexed thoroughly. The RIPA resuspended cells were passed through a pipette tip and incubated on ice for 30 minutes, mixed by vortex and centrifuged for 10 minutes at 14,000 g at 4° C. Supernatants were removed and measured by BCA assay such that 20 µg could be loaded onto gels for Western blotting. For the preparation of peptide recovered microparticles (PREX), 1.8 mLs of bioreactor culture media from each cell line was incubated overnight at 4° C. with 50 µg of Vn96 peptide. Following incubation, the mixtures were centrifuged at 4500 g for 10 min. at 4° C. The pellets were washed and resuspended in 1 mL of 50 mM ArgGlu buffer and repelleted under the same centrifugation conditions. The pellets were solubilized in 200 µL of 1× urea SDS electrophoresis sample buffer (USB). 20 µL volumes of both the RIPA lysates and resuspended peptide recovered microparticles were applied to an 18 well Criterion XT-Bis Tris gel and electrophoresed using XT-MOPS as the running buffer and Western blotted to nitrocellulose membrane. Primary antibodies were directed to: A, valosin containing protein (VCP); B glyceraldehyde phosphate dehydrogenase (GAPDH); C, Tenascin-C (TNC) and D, heat shock protein (HSP60). Antibody incubation conditions and image development were as previously described. Cell origins and treatments are as indicated on FIG. 7A through FIG. 7D. Molecular weight standards (Pierce MW maker) were marked by pencil on the blot as indicated. A commercially available lysate of the cell line K562 was included on each blot (Novus Biologicals Littleton, CO).

Results

Figures 7A, 7B, 7C, 7D:
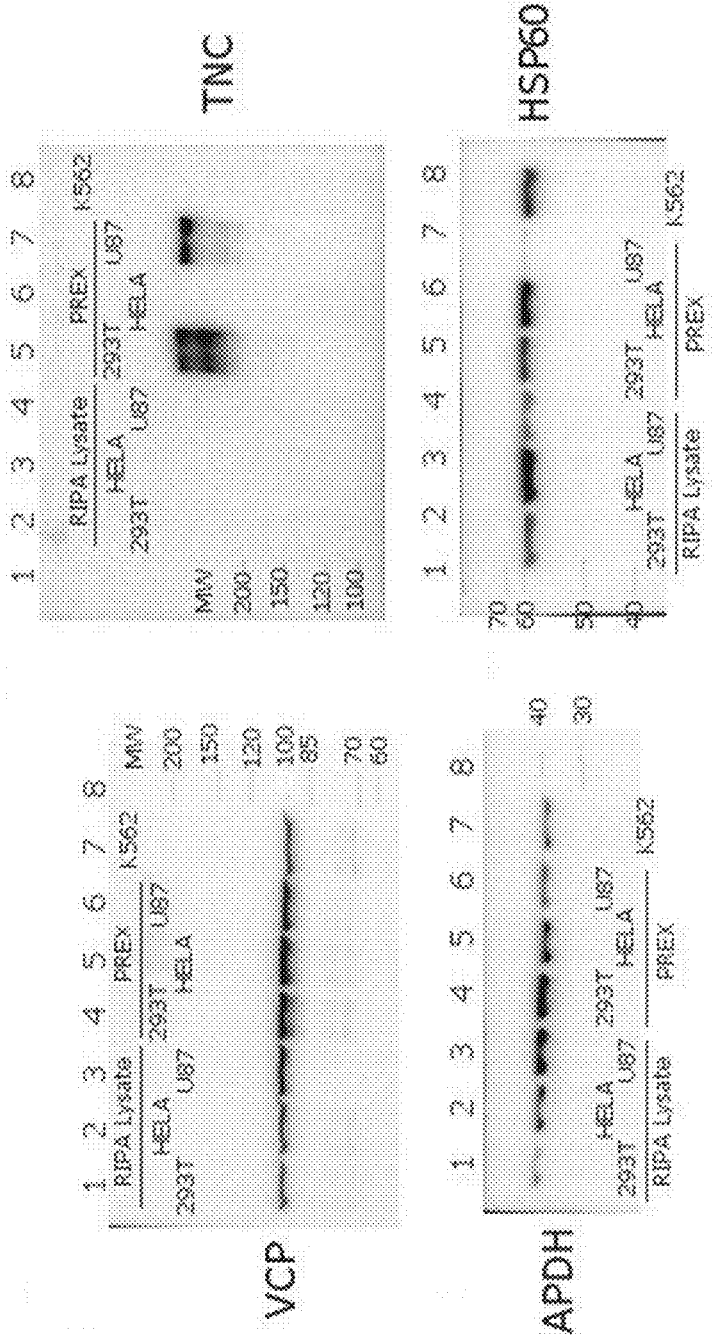
FIG. 7A illustrates VCP protein analysis from RIPA buffer cell lysates or from peptide recovered microparticles using Vn96 peptides (PREX).
FIG. 7B illustrates Tenascin-C protein analysis from RIPA buffer cell lysates or from peptide recovered microparticles (PREX).
FIG. 7C illustrates GAPDH protein analysis from RIPA buffer cell lysates or from peptide recovered microparticles (PREX).
FIG. 7D illustrates HSP60 protein analysis from RIPA buffer cell lysates or from peptide recovered microparticles (PREX).

The results of the assays described above are presented in FIG. 7A-FIG. 7D. As described previously, Tenascin-C levels were robustly present in samples containing microparticles from the tumor or tumor-like cell lines (FIG. 7B). This further demonstrates that Tenascin-C is an extracellular marker of tumor-derived microparticles. VCP, GAPDH, and HSP60 could be detected in both RIPA cell lysate samples and microparticle samples. Further, although Tenascin-C could be detected in association with the microparticles analyzed, this protein could not be detected in the RIPA buffer cell lysates at the same exposure used to detect this protein in association with the microparticles analyzed.

Example 6: Sequential Detergent Extraction of Peptide Recovered Microparticles with Subcellular Proteome Extraction Kit Buffers This Example demonstrates that various subcellular extraction buffers may remove tumor or tumor-derived microparticle proteins from the microparticles. The results depict the relative strength of association between the analyzed proteins and the associated microparticles. This was investigated so that Applicants could determine the strength of subcellular extraction buffer required to release Tenascin-C and two other microparticle proteins from peptide recovered microparticles, namely the glycolytic enzyme glyceraldehyde phosphate dehydrogenase (GAPDH) and the tetraspanin CD63.

Materials and Methods

RIPA lysates of U87, HELA and 293T were prepared for Western blotting as previously described. Sequential detergent extracts of U87, HELA and 293T peptide recovered microparticles (PREX) were prepared using the sub-cellular proteome extraction kit (S-PEK; EMD Milipore, Billerica, MA). Although the purpose of the kit is to produce cell fractions enriched in cytoplasmic, membrane-associated, nuclear and cytoskeletal proteins (with extraction buffers I, II, III and IV respectively).

Peptide recovered microparticle pellets were prepared as previously described from Integra CELLiNE bioreactor media using the Vn96 peptide. The washed peptide recovered microparticle pellets were then sequentially resuspended and repelleted in Extraction Buffer I through to Extraction Buffer IV according to the manufacturer's instructions. The final pellet in the extraction buffer series (IV) was resuspended in 100 µL of urea/SDS buffer, thus representing the most stringent extraction conditions on the remaining material. Supernatants from each of the extraction buffer steps were precipitated by adding 4 volumes of acetone kept at −20° C. and stored overnight at −20° C. Acetone pellets were formed by centrifugation at 14000 g for 5 min. at 4° C. The pellets were washed with 80% acetone Tris-HCl pH 6.8 at 4° C. and pelleted by centrifugation at 14000 g. Pellets were resuspended in 100 μL of urea SDS buffer. 20 μL volumes were loaded onto 4-12% Criterion XT Bis-Tris gels (Bio-Rad), electrophoresed, and subject to Western blot as previously described.

Blots were incubated with antibodies to Tenascin-C (TNC; monoclonal antibody 81C6), glyceraldehyde phosphate dehydrogenase (GAPDH), or CD63 as indicated in FIG. 8A-FIG. 8D. Also indicated are the identities of the individual supernatants from sequential extraction buffers I through IV (roman numerals) beneath each source of peptide recovered microparticles.

Figures 8A, 8B, 8C, 8D:
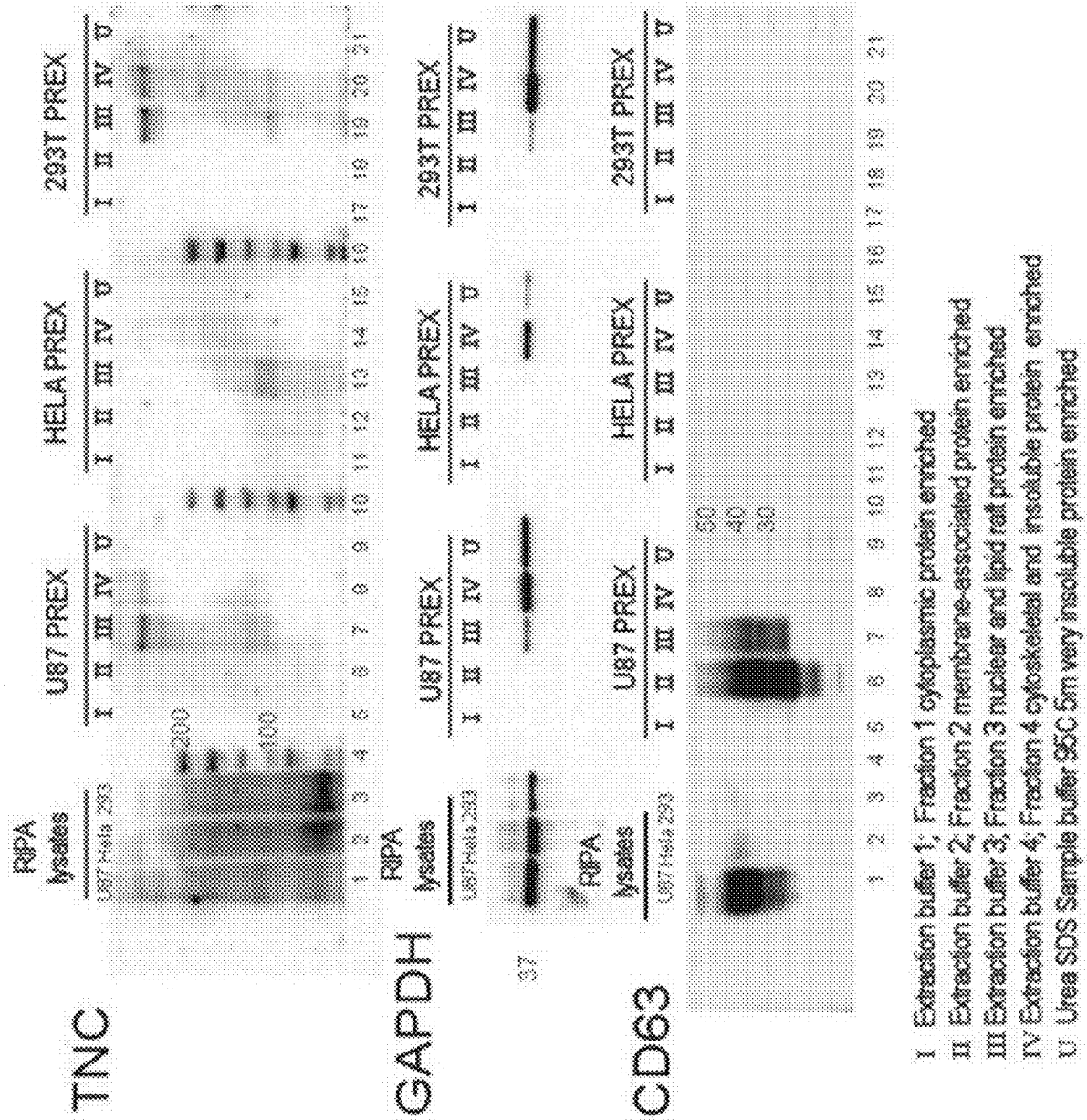
FIG. 8A illustrates Tenascin-C protein analysis from RIPA buffer cell lysates or from peptide recovered microparticles (PREX).
FIG. 8B illustrates GAPDH protein analysis from RIPA buffer cell lysates or from peptide recovered microparticles (PREX).
FIG. 8C illustrates CD63 protein analysis from RIPA buffer cell lysates or from peptide recovered microparticles (PREX).
FIG. 8D illustrates a legend of the identification of the subcellular extraction buffer used in the peptide recovered microparticle protein analysis in FIG. 8A-FIG. 8C.

In FIG. 8A-FIG. 8C, all lanes contain the same samples, but were probed with different antibodies as labeled. RIPA cell lysates from, lane 1, U87; lane 2, HELA; lane 3 293T cells. Lanes 4, 10 and 16 were loaded with molecular weight standards (Pierce Page ruler MW maker).

Results

Analysis of RIPA Cell Lysate and Microparticle Samples Following Exposure to Subcellular Extraction Buffers Table 6-1 illustrates the RIPA buffer cell lysate sample or microparticle sample analyzed in the blot analyses, and the corresponding lanes for the respective samples, the results of which are depicted in FIG. 8A-FIG. 8C. The lane order of FIG. 8A through FIG. 8C is identical.

TABLE 6-1

Identification of Samples or Condition in the Specified Blot Lanes

| Lane # | Sample or Condition |
|---|---|
| 1 | RIPA Lysate-U87 |
| 2 | RIPA Lysate-HELA |
| 3 | RIPA Lysate-HEK293T |
| 4 | MW Standard |
| 5 | U87 PREX-Buffer I |
| 6 | U87 PREX-Buffer II |
| 7 | U87 PREX-Buffer III |
| 8 | U87 PREX-Buffer IV |
| 9 | U87 PREX-Buffer U |
| 10 | MW Standard |
| 11 | HELA PREX-Buffer I |
| 12 | HELA PREX-Buffer II |
| 13 | HELA PREX-Buffer III |
| 14 | HELA PREX-Buffer IV |
| 15 | HELA PREX-Buffer U |
| 16 | MW Standard |
| 17 | HEK293T PREX-Buffer I |
| 18 | HEK293T PREX-Buffer II |
| 19 | HEK293T PREX-Buffer III |
| 20 | HEK293T PREX-Buffer IV |
| 21 | HEK293T PREX-Buffer U |

As can be seen in FIG. 8A, it was observed that TNC could be released from U87 and 293T peptide recovered microparticles in buffers III and IV. Further, FIG. 8A-FIG. 8C also show proteins from RIPA cell lysates being compared to proteins from peptide recovered microparticles that have been subjected to differential detergent fractionation (sequential extraction of proteins by increasingly stronger detergents). The blot in FIG. 8A was allowed longer exposure than FIG. 7B from Example 5, and a series of lower molecular weight bands in the TNC blot may be seen in the RIPA lysates.

Further, in FIG. 8A, smaller molecular weight Tenascin-C bands could be observed in microparticles from the HELA cell line in buffers III and IV, whereas Tenascin-C could not be observed in this cell line in the similar experiment in FIG. 7B, but where no detergent buffers were added.

Further Analysis of Tenascin-C Using ELISA

To further explore the association of Tenascin-C with microparticles derived from tumor or tumor-like cell lines, an ELISA assay was performed to detect Tenascin-C. Peptide recovered microparticles (PREX) were prepared from U87, HELA, and HEK293T cell lines as described above. Briefly, for the preparation of peptide recovered microparticles (PREX), 1.8 mLs of bioreactor culture media from each cell line was incubated overnight at 4° C. with 50 μg of Vn96 peptide. Following incubation, the mixtures were centrifuged at 4500 g for 10 min. at 4° C. The pellets were washed and resuspended in 1 mL of 50 mM ArgGlu (AG) buffer and repelleted under the same centrifugation conditions. The pellets were solubilized in 200 μL of 1× urea SDS electrophoresis sample buffer (USB). The results of the ELISA assay are presented in Table 6-2.

TABLE 6-2

PGXL Measurement of TNC Associated with U87, 293T, and HELA PREX by ELISA

| Sample | Condition | Readout (μg/mL) |
|---|---|---|
| 1-1 | Suspension of PREX (50 μg) U87 (+VE) from 1.8 mls of culture in 50 mM AG | 834.09 |
| 1-2 | Suspension of PREX (50 μg) HEK293T (+VE) from 1.8 mls culture in 50 mM AG | 787.04 |
| 1-3 | Suspension of PREX (50 μg) HELA (−VE) prepared from 1.8 mls culture in 50 mM AG | 67.1 |

As can be seen in Table 6-2, the results suggest that Tenascin-C is present in peptide recovered microparticles from U87, HEK293T, and HELA cell lines, although is possibly less abundant in microparticles from HELA cell lines.

Example 7: Tenascin-C and CD63 can Co-Elute from Microparticle Samples Using Water and Arginine Washes in Column Chromatography This Example illustrates that Tenascin-C and CD63 can co-elute in the same fractions if microparticle samples are subjected to spin filtration at 30 kDa MWCO.

Results

In Example 2, it was observed that extracellular microparticles are bound to agarose matrix during chromatography with water as the mobile phase, and that the addition of an arginine-containing solution following the water phase improved protein release from the column and enrichment of microparticles. Tenascin-C and CD63 were both identified in the microparticle enriched samples.

To further analyze elution techniques to obtain Tenascin-C-positive microparticles, a similar experiment was conducted as described in Example 2, except that peptide-recovered microparticle preparations were subjected to spin filtration at 30 kDa MWCO. Results of this experiment are presented in FIG. 9A-FIG. 9B. When AB Serum is spiked with the culture medium of U87 glioblastoma cells and subject to SEC PD-10 fractionation in water, Tenascin-C may be found in the same fractions as CD63. TNC and CD63 fraction are observed in the second half of the Peak 3, 1 M Arg 5% EtOH, fraction IIIB (fractions 7-12) after spin filtration at 30 kDa MWCO, but not at 1 mDa MWCO.

Figures 9A, 9B:
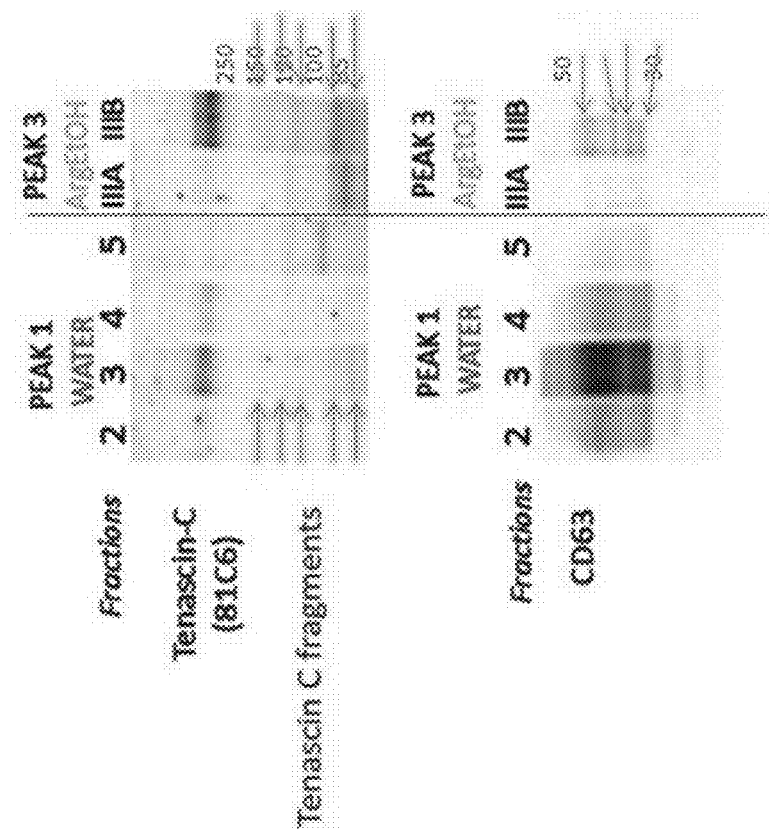
FIG. 9A illustrates Tenascin-C (TNC) protein levels following water PD-10 fractionation of AB Serum spiked with U87 cell culture concentrate.
FIG. 9B illustrates CD63 protein levels following water PD-10 fractionation of AB Serum spiked with U87 cell culture concentrate. Arrows point to protein fragments.

Further, in FIG. 9A and FIG. 9B, the major TNC band and fragments are preserved in both water and in 1M Arginine+ 5% ethanol. Similarly, CD63 isoforms with different degrees of glycosylation are preserved in both water and in 1M Arginine+5% ethanol.

What is claimed is:

1. A method of isolating brain tumor-derived microparticles from a human subject for analysis, the method comprising:
   (1) providing a sample comprising bodily fluid from the human subject;
   (2) subjecting the sample to treatment with a LaurA solution, wherein the solution comprises between 5% and 10% LaurA;
   (3) isolating bodily fluid-derived microparticles from the sample, wherein the bodily-fluid derived microparticles comprise endosome-derived exosomes, plasma membrane-derived shedding vesicles, apoptotic bodies, outer membrane vesicles (OMVs), or a combination thereof, released from cells in the human subject, and wherein the isolating of the bodily fluid-derived microparticles comprises:
      (a) subjecting the sample to ultracentrifugation or size exclusion chromatography (SEC); or
      (b) performing an affinity pulldown with the sample using a Vn96 peptide or a Heladonin peptide as an affinity reagent;
   (4) isolating antibody-purified microparticles from the bodily fluid-derived microparticles using an anti-Tenascin-C antibody; and
   (5) analyzing the antibody-purified microparticles to determine the expression status of at least two biomarkers selected from EGFRvIII, 14-3-3, PPIX, and glycoporin A, wherein the at least two biomarkers selected from a presence of EGFRvIII, a presence of 14-3-3, a presence of PPIX, and an absence of glycoporin A are indicative of the antibody-purified microparticles being brain-tumor derived microparticles.

2. The method of claim 1, wherein the SEC is performed with a solid support and a mobile phase added to the solid support.

3. The method of claim 2, wherein the solid support comprises a column.

4. The method of claim 2, wherein the mobile phase is water.

5. The method of claim 1, wherein the expression status of the at least two biomarkers are determined by an immune-based assay or mass spectrometry.

6. The method of claim 5, wherein the immune-based assay is an immunosorbent assay (ELISA), a radioimmune assay (RIA), a Western blot assay, or a slot blot assay.

7. The method of claim 1, wherein the anti-Tenascin-C antibody is 81C6.

* * * * *

SEQUENCE LISTING

```
Sequence total quantity: 1
SEQ ID NO: 1            moltype = AA  length = 27
FEATURE                 Location/Qualifiers
source                  1..27
                        mol_type = protein
                        organism = synthetic construct
SEQUENCE: 1
LKLFEGLTLA GWSFRSLSLG RGKGQSP                                       27
```